United States Patent
Sato et al.

(10) Patent No.: US 10,851,392 B2
(45) Date of Patent: *Dec. 1, 2020

(54) METHOD FOR PRODUCING METHACRYLIC ACID ESTER

(71) Applicant: Mitsubishi Chemical Corporation, Tokyo (JP)

(72) Inventors: Eiji Sato, Kanagawa (JP); Fujio Yu, Kanagawa (JP); Wataru Mizunashi, Kanagawa (JP); Eiji Nakajima, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/405,593

(22) PCT Filed: Sep. 10, 2013

(86) PCT No.: PCT/JP2013/005354
§ 371 (c)(1),
(2) Date: Dec. 4, 2014

(87) PCT Pub. No.: WO2014/038214
PCT Pub. Date: Mar. 13, 2014

(65) Prior Publication Data
US 2015/0184207 A1    Jul. 2, 2015

(30) Foreign Application Priority Data

Sep. 10, 2012 (JP) ................. 2012-198840
Aug. 1, 2013 (JP) ................. 2013-160300
Aug. 20, 2013 (JP) ................. 2013-170404

(51) Int. Cl.
*C12P 7/62* (2006.01)
*C12N 9/10* (2006.01)
*C12N 1/20* (2006.01)

(52) U.S. Cl.
CPC ............. *C12P 7/62* (2013.01); *C12N 1/20* (2013.01); *C12N 9/1025* (2013.01); *C12Y 203/01084* (2013.01)

(58) Field of Classification Search
None
See application file for complete search history.

(56) References Cited

U.S. PATENT DOCUMENTS

| | | |
|---|---|---|
| 2003/0148480 A1 | 8/2003 | Dicosimo et al. |
| 2008/0076167 A1 | 3/2008 | Gokarn et al. |
| 2009/0130729 A1 | 5/2009 | Symes et al. |
| 2009/0275096 A1 | 11/2009 | Burgard et al. |
| 2010/0291644 A1 | 11/2010 | Marx et al. |
| 2011/0165640 A1 | 7/2011 | Mueller et al. |
| 2013/0065279 A1 | 3/2013 | Burk et al. |

FOREIGN PATENT DOCUMENTS

| | | |
|---|---|---|
| CA | 2 688 292 A1 | 12/2008 |
| EP | 0 187 680 A2 | 7/1986 |
| EP | 3 029 145 | 6/2016 |
| JP | 54-46887 A | 4/1979 |
| JP | 61-162191 A | 7/1986 |
| JP | 62-14788 A | 1/1987 |
| JP | 1-132392 A | 5/1989 |
| JP | 05-064589 A | 3/1993 |
| JP | 10-248578 A | 9/1998 |
| JP | 10-337185 A | 12/1998 |
| JP | 2004-514431 A | 5/2004 |
| JP | 2005-516622 A | 6/2005 |
| JP | 2009-538118 A | 11/2009 |
| JP | 2010-528597 A | 8/2010 |
| JP | 2011-519561 A | 7/2011 |
| JP | 2011-200133 A | 10/2011 |
| JP | 2012-198840 | 9/2012 |
| JP | 2013-160300 | 8/2013 |
| JP | 2013-160302 | 8/2013 |
| WO | 00/32789 A1 | 6/2000 |
| WO | WO 2000/032789 * | 6/2000 |
| WO | WO 2005/090586 A1 | 9/2005 |
| WO | 2007/039415 A1 | 4/2007 |
| WO | 2007/110394 A2 | 10/2007 |
| WO | 2008/145737 A1 | 12/2008 |
| WO | 2009/135074 A2 | 11/2009 |
| WO | 2011/031897 A1 | 3/2011 |
| WO | 2012/135789 A2 | 10/2012 |
| WO | WO 2015/015784 | 2/2015 |

OTHER PUBLICATIONS

Beekwilder et al., "Functional Characterization of Enzymes Forming Volatile Esters from Strawberry and Banana", Plant Physiology, Aug. 2004, vol. 135, pp. 1865-1878.*
Baltoni'n et al., "VpAAT1, a Gene Encoding an Alcohol Acyltransferase, Is Involved in Ester Biosynthesis during Ripening of Mountain Papaya Fruit", J. Agric. Food Chem. 2010, 58, 5114-5121. DOI:10.1021/jf904296c.*
Quintana et al., "Molecular docking simulation analysis of alcohol acyltransferases from two related fruit species explains their different substrate selectivities", Molecular Simulation, 38(11):912-921.*
Souleyre et al., "An alcohol acyl transferase from apple (cv. Royal Gala), MpAAT1, produces esters involved in apple fruit flavor", FEBS Journal 272 (2005) 3132-3144.*
Extended European Search Report dated Jul. 6, 2015 in Patent Application No. 13834617.6.
Edwige J. F. Souleyre, et al., "An alcohol acyl transferase from apple (cv. Royal Gala), MpAAT1, produces esters involved in apple fruit flavor" FEBS Journal, vol. 272, No. 12, XP055197639, 2005, pp. 3132-3144.

(Continued)

*Primary Examiner* — Suzanne M Noakes
(74) *Attorney, Agent, or Firm* — Oblon, McClelland, Maier & Neustadt, L.L.P.

(57) ABSTRACT

Provided is a method for producing a methacrylic acid ester using a biocatalyst, said method comprising a step for treating methacrylyl-CoA with an alcohol or phenol in the presence of an alcohol acyltransferase to synthesize the methacrylic acid ester. According to this production method, a methacrylic acid ester can be efficiently produced while largely reducing energy, resource and environmental load, compared with the conventional chemical production processes.

10 Claims, 5 Drawing Sheets

Specification includes a Sequence Listing.

(56) References Cited

OTHER PUBLICATIONS

Catherine Emily Horton, et al., "Ester production in *E. coli* and *C. acetobutylicum*" Enzyme and Microbial Technology, vol. 38, No. 7, XP027948848, 2006, pp. 937-943.

John C. D'Auria, "Acyltransferases in plants: a good time to be BAHD" Current Opinion in Plant Biology, vol. 9, No. 3, XP028014883, 2006, pp. 331-340.

International Search Report dated Nov. 19, 2013 in PCT/JP2013/005354 filed Sep. 10, 2013.

Sang-Hyun Pyo, et al., "A new route for the synthesis of methacrylic acid from 2-methyl-1,3-propanediol by integrating biotransofmration and catalytic dehydration" Green Chemistry, vol. 14, 2012, pp. 1942-1948.

John W. Hawes, "[8] Synthesis of Methacrylyl-CoA and (R)- and (S)-3-Hydroxyisobutyryl-CoA" Methods in Enzymology, vol. 324, 2000, pp. 73-79.

Birgitta Bremer, et al., "An update of the Angiosperm Phylogeny Group classification for the orders and families of flowering plants APG III" Botanical Journal of the Linnean Society, vol. 161, 2009, pp. 105-121.

Ying-Xin Zhang, et al., "Genes encoding acyl-CoA dehydrogenase (AcdH) homologues from *Streptomyces coelicolor* and *Streptomyces avermitilis* provide insights into the metabolism of small branched-chain fatty acids and macrolide antibiotic production" Microbiology, vol. 145, 1999, pp. 2323-2334.

Mark R. Smith, et al., "The Utilization of 3-Mercapto-2-Methylpropionate as Sulphur Source by a Phototrophic Bacterium" Bioorganic & Medicinal Chemistry, vol. 2, No. 7, 1994, pp. 589-593.

Office Action dated Aug. 27, 2018 in India Patent Application No. 595/CHENP/2015.

Extended European Search Report dated Oct. 8, 2018 in Patent Application No. 18175984.6.

Office Action dated Oct. 11, 2018 in European Patent Application No. 13 835 104.4.

Natalia Korotkova, et al., "Glyoxylate Regeneration Pathway in the Methylotroph *Methylobacterium extorquens* AM1", Journal of Bacteriology, vol. 184, No. 6, Mar. 2002, pp. 1750-1758.

Toru Nagasawa, et al., "Production of acrylic acid and methacrylic acid using *Rhodococcus rhodochrous* J1 nitrilase", Applied Microbiology and Biotechnology, vol. 34, 1990, pp. 322-324.

Office Action dated May 15, 2018 in Chinese Patent Application No. 201380047196.3 with English translation.

Ozcan, G., "Effect of Enzymes of Strawberry Volatiles During Storage, at Different Ripeness Level, in Different Cultivars and During Eating", 2010, The Ohio State University.

Yamashita, I., "Formation of Volatile Esters in Strawberries", Agr. Biol. Chem., vol. 39, No. 12, 1975, pp. 2303-2307.

Aharoni, A., "Identification of the SAAT Gene Involved in Strawberry Flavor Biogenesis by Use of DNA Microarrays", The Plant Cell, vol. 12, May 2000, pp. 647-661.

Wu, W., "Stereospecificity of the Reaction Catalyzed by Enoyl-CoA Hydratase", Journal of the American Chemical Society, vol. 122, No. 17, May 3, 2000, pp. 3987-3994.

Wanders, R., "Enzymology of the Branched-Chain Amino Acid Oxidation Disorders: The Valine Pathway", J. Inherit Metab. Dis., vol. 35, 2012, pp. 5-12.

Notice of Opposition in European Application No. EP13834617.6, issued Apr. 26, 2019.

Summons to attend oral proceedings pursuant to Rule 115(1) EPC issued on Feb. 20, 2020 in European Patent Application No. 13834617.6, 12 pages.

European Office Action dated Mar. 23, 2020 in Patent Application No. 18175984.6, 10 pages.

Sompoch Noichinda, et al. "Subcellular Localization of Alcohol Acetyltransferase in Strawberry Fruit" Food Sci. Technol., vol. 5, No. 3, 1999, pp. 239-242.

"Making Esters" Extract from Chemguide, https://www.chemguide.co.uk/organicprops/esters/preparation.html, 2004, pp. 1-5.

Office Action in corresponding European Application No. 18175984.6, dated Jun. 10, 2020.

G. Ozcan, et al., "Effect of Enzymes on Strawberry Volatiles during Storage, at Different Ripeness Level, in Different Cultivars, and during Eating", Journal of Food Science, vol. 75, No. 2, 2011, pp. C324-C333.

Office Action in corresponding Chinese Application No. 2013800471963 dated Jul. 20, 2020. (w/English Translation).

\* cited by examiner 2-oxoisovaleric acid    isobutyryl-CoA    methacrylyl-CoA    methacrylic acid ester

SEQUENCE LISTING

```
<160> NUMBER OF SEQ ID NOS: 37

<210> SEQ ID NO 1
<211> LENGTH: 455
<212> TYPE: PRT
<213> ORGANISM: Malus x domestica(MpAAT1)

<400> SEQUENCE: 1

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Cys
        35                  40                  45

Tyr Lys Asp Asn Pro Ser Leu Asn Lys Asn Arg Asn Pro Val Lys Ala
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Lys Ile Leu Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Cys Leu Thr Cys Gly Phe Ile Leu Ala Leu
145                 150                 155                 160

Arg Leu Asn His Thr Met Cys Asp Ala Ala Gly Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300
```

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
            325                 330                 335

Val Lys Lys Ala Lys Ala Thr Met Asn Glu Glu Tyr Leu Arg Ser Val
        340                 345                 350

Ala Asp Leu Leu Val Leu Arg Gly Arg Pro Gln Tyr Ser Ser Thr Gly
    355                 360                 365

Ser Tyr Leu Ile Val Ser Asp Asn Thr Arg Val Gly Phe Gly Asp Val
370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
            405                 410                 415

Ile Leu Val Pro Met Cys Leu Pro Ser Ser Ala Met Glu Arg Phe Gln
        420                 425                 430

Gln Glu Leu Glu Arg Ile Thr Gln Glu Pro Lys Glu Asp Ile Cys Asn
    435                 440                 445

Asn Leu Arg Ser Thr Ser Gln
    450                 455

<210> SEQ ID NO 2
<211> LENGTH: 1368
<212> TYPE: DNA
<213> ORGANISM: Malus x domestica(MpAAT1)

<400> SEQUENCE: 2
atgaaatcat tctcagtact tcaggtgaaa cgattgcaac cggaacttat aactccggca      60
aagtcaacgc ctcaagaaac aaagtttctc tcagatattg acgaccaaga aagcttgaga     120
gttcagattc caatcataat gtgttacaaa gacaaccctt cacttaataa aaatcgtaat     180
cccgttaagg caattaggga agccttaagt agagcattag tgtattacta cccttagct     240 ggaaggctta gggaagggcc taatagaaag ctcgtggtcg attgcaatgg tgaaggtatc     300
ttgttcgttg aggcttctgc tgatgtcaca cttgagcaac taggagacaa aattctaccc     360
ccttgtccac ttttagagga gttcttatat aattttccag ctctgatgg aattattgat     420 tgtcctttgc tgctgattca ggtgacctgt cttacatgtg gaggtttcat acttgcattg     480
cgcctaaacc acacaatgtg tgatgcagct ggattgctct tgttcctgac cgccatcgcg     540
gagatggcaa gaggcgcaca tgcaccatct attctaccag tgtgggagag agagctcttg     600
ttcgctcgag atccaccaag aattacatgt gctcatcacg aatatgaaga cgtgattggt     660
cattctgatg gctcatacgc atccagtaac cagtcaaaca tggttcaacg atctttctac     720
tttggtgcca aggagatgag agtccttcga aaacagattc caccccacct aatttccact     780
tgctccacat ttgacttgat cacagcttgt tgtggaaat gtcgcactct tgcacttaac     840
attaatccaa agaggctgt tcgagtttca tgcattgtca atgcacgagg aaagcacaac     900
aatgtacgtc ttccccttggg atactatggc aatgcatttg catttccagc tgcaatttcg     960
aaggctgaac tctatgcaa aaatccactg ggatatgctt tggagttggt gaagaaggct    1020
aaagctacca tgaatgaaga atacttaaga tcagtggcag atcttttggt actaagaggg    1080
cgacctcaat attcatcgac aggaagttat ttaatagttt ctgataatac gcgtgtaggt    1140
tttggagatg tcaattttgg atggggacag ccggtatttg ctggaccgt caaggccttg    1200 gatttgatta gcttctacgt tcaacacaaa aacaacacag aggatggaat attggtacca 1260
atgtgtttgc catcctcggc catggagaga tttcagcagg aactagagag gattactcag 1320
gaacctaagg aggatatatg taacaacctt agatcaacta gtcaatga 1368

<210> SEQ ID NO 3
<211> LENGTH: 452
<212> TYPE: PRT
<213> ORGANISM: Fragaria x ananassa(SAAT)

<400> SEQUENCE: 3

```
Met Asn Lys Ile Glu Val Ser Ile Asn Ser Lys His Thr Ile Lys Pro
1               5                   10                  15

Ser Thr Ser Thr Pro Leu Gln Pro Tyr Lys Leu Thr Leu Leu Asp
            20                  25                  30

Gln Leu Thr Pro Pro Ala Tyr Val Pro Ile Val Phe Phe Tyr Pro Ile
        35                  40                  45

Thr Asp His Asp Phe Asn Leu Pro Gln Thr Leu Ala Asp Leu Arg Gln
50                  55                  60

Ala Leu Ser Glu Thr Leu Thr Leu Tyr Tyr Pro Leu Ser Gly Arg Val
65                  70                  75                  80

Lys Asn Asn Leu Tyr Ile Asp Asp Phe Glu Glu Gly Val Pro Tyr Leu
                85                  90                  95

Glu Ala Arg Val Asn Cys Asp Met Thr Asp Phe Leu Arg Leu Arg Lys
            100                 105                 110

Ile Glu Cys Leu Asn Glu Phe Val Pro Ile Lys Pro Phe Ser Met Glu
        115                 120                 125

Ala Ile Ser Asp Glu Arg Tyr Pro Leu Leu Gly Val Gln Val Asn Val
130                 135                 140

Phe Asp Ser Gly Ile Ala Ile Gly Val Ser Val Ser His Lys Leu Ile
145                 150                 155                 160

Asp Gly Gly Thr Ala Asp Cys Phe Leu Lys Ser Trp Gly Ala Val Phe
                165                 170                 175

Arg Gly Cys Arg Glu Asn Ile Ile His Pro Ser Leu Ser Glu Ala Ala
            180                 185                 190

Leu Leu Phe Pro Pro Arg Asp Asp Leu Pro Glu Lys Tyr Val Asp Gln
        195                 200                 205

Met Glu Ala Leu Trp Phe Ala Gly Lys Lys Val Ala Thr Arg Arg Phe
210                 215                 220

Val Phe Gly Val Lys Ala Ile Ser Ser Ile Gln Asp Glu Ala Lys Ser
225                 230                 235                 240

Glu Ser Val Pro Lys Pro Ser Arg Val His Ala Val Thr Gly Phe Leu
                245                 250                 255

Trp Lys His Leu Ile Ala Ala Ser Arg Ala Leu Thr Ser Gly Thr Thr
            260                 265                 270

Ser Thr Arg Leu Ser Ile Ala Ala Gln Ala Val Asn Leu Arg Thr Arg
        275                 280                 285

Met Asn Met Glu Thr Val Leu Asp Asn Ala Thr Gly Asn Leu Phe Trp
290                 295                 300

Trp Ala Gln Ala Ile Leu Glu Leu Ser His Thr Thr Pro Glu Ile Ser
305                 310                 315                 320

Asp Leu Lys Leu Cys Asp Leu Val Asn Leu Leu Asn Gly Ser Val Lys
                325                 330                 335

Gln Cys Asn Gly Asp Tyr Phe Glu Thr Phe Lys Gly Lys Glu Gly Tyr
            340                 345                 350
```

```
Gly Arg Met Cys Glu Tyr Leu Asp Phe Gln Arg Thr Met Ser Ser Met
            355                 360                 365

Glu Pro Ala Pro Asp Ile Tyr Leu Phe Ser Ser Trp Thr Asn Phe Phe
370                 375                 380

Asn Pro Leu Asp Phe Gly Trp Gly Arg Thr Ser Trp Ile Gly Val Ala
385                 390                 395                 400

Gly Lys Ile Glu Ser Ala Ser Cys Lys Phe Ile Ile Leu Val Pro Thr
            405                 410                 415

Gln Cys Gly Ser Gly Ile Glu Ala Trp Val Asn Leu Glu Glu Glu Lys
                420                 425                 430

Met Ala Met Leu Glu Gln Asp Pro His Phe Leu Ala Leu Ala Ser Pro
            435                 440                 445

Lys Thr Leu Ile
    450
```

<210> SEQ ID NO 4
<211> LENGTH: 1359
<212> TYPE: DNA
<213> ORGANISM: Fragaria x ananassa(SAAT)

<400> SEQUENCE: 4

```
atgaacaaaa ttgaggtcag tataaattcc aaacacacca tcaaaccatc aacttcctct      60
acaccacttc agccttacaa gcttacccctc ctggaccagc tcactcctcc ggcgtatgtc    120
cccatcgtgt tcttctaccc cattactgac catgacttca atcttcctca aaccctagct    180
gacttaagac aagcccttc ggagactctc actttgtact atccactctc tggaagggtc    240
aaaaacaacc tatacatcga tgattttgaa aaggtgtcc cataccttga ggctcgagtg    300
aattgtgaca tgactgattt tctaaggctt cggaaaatcg agtgccttaa tgagtttgtt    360
ccaataaaac catttagtat ggaagcaata tctgatgagc gttacccctt gcttggagtt    420
caagtcaacg ttttcgattc tggaatagca atcggtgtct ccgtctctca aagctcatc     480
gatggaggaa cggcagactg ttttctcaag tcctggggtg ctgtttttcg agggtgtcgt    540
gaaaatatca tacatcctag tctctctgaa gcagcattgc ttttcccacc gagagatgac    600
ttgcctgaaa agtatgtcga tcagatggaa gcgttatggt ttgccggaaa aaagttgct    660
acaaggagat ttgtatttgg tgtgaaagcc atatcttcaa ttcaagatga gcgaagagc    720
gagtccgtgc ccaagccatc acgagttcat gccgtcactg ttttctctg aaacatcta    780
atcgctgctt ctcgggcact aacatcaggt actacttcaa caagactttc tatagcggcc    840
caggcagtga acttaagaac acggatgaac atggagacag tgttggataa tgccactgga    900
aacttgttct ggtgggcaca ggccatacta gagctaagtc atacaacacc agagatcagt    960
gatcttaagc tgtgtgactt ggttaacttg ctcaatggat ctgtcaaaca atgtaacggt   1020
gattactttg agactttcaa gggtaaagag ggatatggaa gaatgtgcga gtatctagat   1080
tttcagagga ctatgagttc tatggaacca gcaccggata tttatttatt ctcgagctgg   1140
actaattttt tcaacccact tgattttgga tggggagga catcatggat tggagttgca   1200
ggaaaaattg aatctgcaag ttgcaagttc ataatattag ttccaacaca atgcggttct   1260
ggaattgaag cgtgggtgaa tctagaagaa gagaaaatgg ctatgctaga caagatccc    1320
catttctag cgttagcatc tccaaagacc ttaatttaa                            1359
```

<210> SEQ ID NO 5
<211> LENGTH: 455

<212> TYPE: PRT
<213> ORGANISM: Fragaria vesca(VAAT)

<400> SEQUENCE: 5

```
Met Asn Lys Ile Glu Val Ser Ile Ile Ser Lys His Thr Ile Lys Pro
 1               5                  10                  15

Ser Thr Ser Ser Ser Pro Leu Gln Pro Tyr Lys Leu Thr Leu Leu Asp
            20                  25                  30

Gln Leu Thr Pro Pro Ser Tyr Val Pro Met Val Phe Phe Tyr Pro Ile
        35                  40                  45

Thr Gly Pro Ala Val Phe Asn Leu Gln Thr Leu Ala Asp Leu Arg His
50                  55                  60

Ala Leu Ser Glu Thr Leu Thr Leu Tyr Tyr Pro Leu Ser Gly Arg Val
65                  70                  75                  80

Lys Asn Asn Leu Tyr Ile Asp Asp Phe Glu Glu Gly Val Pro Tyr Leu
                85                  90                  95

Glu Ala Arg Val Asn Cys Asp Met Asn Asp Phe Leu Arg Leu Pro Lys
            100                 105                 110

Ile Glu Cys Leu Asn Glu Phe Val Pro Ile Lys Pro Phe Ser Met Glu
        115                 120                 125

Ala Ile Ser Asp Glu Arg Tyr Pro Leu Leu Gly Val Gln Val Asn Ile
130                 135                 140

Phe Asn Ser Gly Ile Ala Ile Gly Val Ser Val Ser His Lys Leu Ile
145                 150                 155                 160

Asp Gly Arg Thr Ser Asp Cys Phe Leu Lys Ser Trp Cys Ala Val Phe
                165                 170                 175

Arg Gly Ser Arg Asp Lys Ile Ile His Pro Asn Leu Ser Gln Ala Ala
            180                 185                 190

Leu Leu Phe Pro Pro Arg Asp Asp Leu Pro Glu Lys Tyr Ala Arg Gln
        195                 200                 205

Met Glu Gly Leu Trp Phe Val Gly Lys Lys Val Ala Thr Arg Arg Phe
210                 215                 220

Val Phe Gly Ala Lys Ala Ile Ser Val Ile Gln Asp Glu Ala Lys Ser
225                 230                 235                 240

Glu Ser Val Pro Lys Pro Ser Arg Val Gln Ala Val Thr Ser Phe Leu
                245                 250                 255

Trp Lys His Leu Ile Ala Thr Ser Arg Ala Leu Thr Ser Gly Thr Thr
            260                 265                 270

Ser Thr Arg Leu Ser Ile Ala Thr Gln Val Val Asn Ile Arg Ser Arg
        275                 280                 285

Arg Asn Met Glu Thr Val Trp Asp Asn Ala Ile Gly Asn Leu Ile Trp
290                 295                 300

Phe Ala Pro Ala Ile Leu Glu Leu Ser His Thr Thr Leu Glu Ile Ser
305                 310                 315                 320

Asp Leu Lys Leu Cys Asp Leu Val Asn Leu Leu Asn Gly Ser Val Lys
                325                 330                 335

Gln Cys Asn Gly Asp Tyr Phe Glu Thr Phe Met Gly Lys Glu Gly Tyr
            340                 345                 350

Gly Ser Met Cys Glu Tyr Leu Asp Phe Gln Arg Thr Met Ser Ser Met
        355                 360                 365

Glu Pro Ala Pro Glu Ile Tyr Leu Phe Thr Ser Trp Thr Asn Phe Phe
370                 375                 380

Asn Gln Leu Asp Phe Gly Trp Gly Arg Thr Ser Trp Ile Gly Val Ala
385                 390                 395                 400
```

```
Gly Lys Ile Glu Ser Ala Phe Cys Asn Leu Thr Thr Leu Val Pro Thr
            405                 410                 415

Pro Cys Asp Thr Gly Ile Glu Ala Trp Val Asn Leu Glu Glu Glu Lys
            420                 425                 430

Met Ala Met Leu Glu Gln Asp Pro Gln Phe Leu Ala Leu Ala Ser Pro
            435                 440                 445

Lys Thr Leu Ile Ser Arg Tyr
    450                 455

<210> SEQ ID NO 6
<211> LENGTH: 1368
<212> TYPE: DNA
<213> ORGANISM: Fragaria vesca(VAAT)

<400> SEQUENCE: 6
atgaacaaaa ttgaggtcag tataatttcc aaacacacca tcaaaccatc aacttcctct      60
tcaccacttc agccttacaa gcttaccctg ctcgaccagc tcactcctcc atcgtatgtc     120
cccatggtat tcttctaccc cattactggc cctgcagtct tcaatcttca aaccctagct     180
gacttaagac atgcccttcc cgagactctc actttgtact atccactctc tggaagggtc     240
aaaaacaacc tatacatcga tgattttgaa gagggtgtcc cataccttga ggctcgagtg     300
aactgtgaca tgaatgattt tctaaggctt ccgaaaatcg agtgcctaaa tgagtttgtt     360
ccaataaaac catttagtat ggaagcaata tctgatgagc gttaccctt gctcggagtt      420 caagttaaca ttttcaactc cggaatagca atcgggtct ccgtctctca caagctcatc      480
gatggaagaa cttcagactg ttttctcaag tcgtggtgtg ctgttttcg tggttctcgt     540 gacaaaatca tacatcctaa tctctctcaa gcagcattgc ttttcccacc aagagatgac     600
ttgcctgaaa gtatgcccg tcagatggaa gggttatggt ttgtcggaaa aaagttgct       660 acaaggagat ttgtatttgg tgcgaaagcc atatctgtaa ttcaagatga agcaaagagc     720
gagtccgtgc ccaagccatc acgagttcag gctgtcacta gttttctctg gaaacatcta    780
atcgctactt ctcgggcact aacatcaggt actacttcaa caagactttc tatagcaacc    840
caggtagtga acataagatc acggaggaac atggagacag tgtgggataa tgccattgga    900
aacttgatat ggttcgctcc ggccatacta gagctaagtc atacaacact agagatcagt    960
gatcttaagc tgtgtgactt ggttaacttg ctcaatggat ctgtcaaaca atgtaacggt   1020
gattactttg agactttcat gggtaaagag ggatatggaa gcatgtgcga gtatctagat   1080
tttcagagga ctatgagttc tatggaacca gcaccagaga tttatttatt cacgagctgg   1140
actaattttt tcaaccaact tgatttggga tggggagga catcatggat tggagttgca   1200
ggaaaaattg aatctgcatt ttgcaatctc acaacattag ttccaacacc atgcgatact   1260
ggaattgaag cgtgggtgaa tctagaagaa gaaaaaatgg ctatgctaga caagatccc    1320 cagtttctag cactagcatc tccaaagacg ctaatttcaa gatattga                1368

<210> SEQ ID NO 7
<211> LENGTH: 387
<212> TYPE: PRT
<213> ORGANISM: Pseudomonas aeruginosa PA01(acd1)

<400> SEQUENCE: 7

Met Asp Phe Asp Leu Thr Glu Glu Gln Arg Leu Leu Val Glu Ser Ala
1               5                   10                  15

Arg Ala Phe Ala Arg His Glu Leu Ala Pro Lys Ala Ala Asp Trp Asp
```

```
                    20                  25                  30
Arg Asp His His Phe Pro Val Glu Val Ile Arg Ala Ala Glu Gln
                35                  40                  45

Gly Tyr Leu Gly Leu Tyr Ile Ala Glu Glu Asp Gly Gly Leu Gly Leu
 50                  55                  60

Ser Arg Leu Ser Thr Ser Leu Ile Phe Glu Gln Leu Ala Ala Gly Cys
 65                  70                  75                  80

Val Ala Thr Thr Ala Tyr Ile Ser Ile His Asn Met Ala Ala Trp Met
                 85                  90                  95

Leu Ala Ser Phe Gly Asp Ala Ala Leu Lys Glu Ala Trp Leu Pro Gly
                100                 105                 110

Leu Ile Gly Gly Glu Ser Leu Ala Ser Tyr Cys Leu Thr Glu Pro Asp
                115                 120                 125

Ala Gly Ser Asp Ala Ala Arg Leu Arg Thr Arg Ala Arg Arg Glu Gly
                130                 135                 140

Asp Glu Tyr Val Leu Asp Gly Ser Lys Cys Phe Ile Ser Gly Ala Gly
145                 150                 155                 160

Ser Thr Gln Val Leu Ile Val Met Ala Arg Thr Gly Glu Asp Gly Ala
                165                 170                 175

Arg Gly Ile Ser Cys Phe Leu Val Pro Ala Asp Ala Pro Gly Ile Arg
                180                 185                 190

Tyr Gly Arg Asn Glu Asp Lys Met Gly Trp Arg Ala Gln Pro Thr Arg
                195                 200                 205

Thr Ile Thr Phe Glu Gly Val Arg Ile Pro Ala Gly Asn Arg Ile Gly
                210                 215                 220

Pro Glu Gly Gln Gly Phe Val Tyr Ala Met Lys Gly Leu Asp Gly Gly
225                 230                 235                 240

Arg Leu Asn Ile Ala Ser Cys Ser Leu Gly Ala Ala Gln Ala Ala Leu
                245                 250                 255

Glu Gln Ser Met Arg Tyr Val Glu Glu Arg Glu Gln Phe Gly Lys Pro
                260                 265                 270

Leu Ala Thr Phe Gln Ala Leu Gln Phe Lys Leu Ala Asp Met Leu Thr
                275                 280                 285

Glu Leu Thr Ala Ser Arg Gln Met Val Arg Leu Gly Ala His Arg Leu
                290                 295                 300

Asp Arg Gly Asp Ala Glu Ala Thr Leu Tyr Cys Ala Met Ala Lys Arg
305                 310                 315                 320

Phe Ala Thr Asp Arg Cys Phe Asp Val Cys Asn Glu Ala Leu Gln Leu
                325                 330                 335

His Gly Gly Tyr Gly Tyr Leu Asn Asp Tyr Pro Leu Glu Arg Trp Val
                340                 345                 350

Arg Asp Thr Arg Val His Gln Ile Leu Glu Gly Thr Asn Glu Ile Met
                355                 360                 365

Arg Val Ile Val Ala Arg Arg Leu Leu Glu Gln Gly Gly Met Leu Asp
                370                 375                 380

Arg Leu Leu
385

<210> SEQ ID NO 8
<211> LENGTH: 1164
<212> TYPE: DNA
<213> ORGANISM: Pseudomonas aeruginosa PAO1(acd1)

<400> SEQUENCE: 8
```

```
atggatttcg acctcaccga agaacaacgc ctgctggtgg agagcgcccg cgccttcgcc        60
cgccacgaac tggcgccgaa ggcggccgac tgggaccgcg accatcactt cccggtggaa       120
gtcatccgcg ccgccgccga acagggctac ctcggcctgt acatcgccga ggaagacggc       180
ggcctgggcc tgtcgcggct gtccacttcg ctgatcttcg agcaactggc cgccggctgc       240
gtggccacta ccgcctacat cagcatccac aacatggccg cctggatgct cgcctcgttc       300
ggcgacgcgg cgctgaagga ggcctggctg cccggcctga tcggcggcga gtcgctcgcc       360
tcctattgcc tgaccgagcc cgatgccggc tccgacgccg cgcgcctgcg cacccgcgcc       420
cgccgcgagg cgacgaaata cgtgctggac ggcagcaagt gcttcatttc cggcgccggc       480
agcacccagg tgctgatcgt catggcgcgc accggcgagg acggcgccag gggcatctcc       540
tgcttcctgg taccggccga cgcgcccggc atccgctacg ccgcaacga ggacaagatg        600
ggctggcgcg cgcagccgac ccgcaccatc accttcgaag gcgtgcgcat cccgccggc        660
aaccgcatcg gccgggaggg ccaaggcttc gtctatgcca tgaaaggcct cgacggcggc       720
cgcctgaaca tcgccagttg ttccctgggc gccgcccagg cggcgctgga gcagtcgatg       780
cgctacgtcg aggagcgcga gcagttcggc aagccgctgg cgaccttcca ggccttgcag       840
ttcaagctcg ccgacatgct caccgaactc accgccagcc gccagatggt ccgcctcggc       900
gcccatcggc tggaccgcgg cgacgccgag gcgaccctgt actgcgcaat ggccaagcgc       960
ttcgccaccg accgctgctt cgatgtctgc aacgaggcct gcaactgca cggcggctac      1020
ggctatctca cgattatcc gctggagcgc tgggtacgcg acacccgcgt gcaccagatc       1080
ctcgaaggca ccaacgaaat catgcgggtg atcgtcgccc ccgcctgct ggagcagggc       1140
ggcatgctcg atcgcctgct gtga                                             1164
```

<210> SEQ ID NO 9
<211> LENGTH: 258
<212> TYPE: PRT
<213> ORGANISM: Rhodococcus erythropolis PR4(RE_echA)

<400> SEQUENCE: 9

Met Thr Asp Phe Asn Thr Ile Ile Leu Glu Arg Lys Gly Arg Val Gly
1               5                   10                  15

Val Ile Thr Leu Asn Arg Pro Lys Ala Leu Asn Ala Leu Asn Ser Glu
            20                  25                  30

Leu Met Asn Glu Val Val Ala Val Ala Asp Leu Glu Ala Asp Asn
        35                  40                  45

Gly Ile Gly Ala Ile Leu Ile Thr Gly Ser Glu Arg Ala Phe Ala Ala
    50                  55                  60

Gly Ala Asp Ile Lys Glu Met Gln Ser Lys Thr Tyr Met Asp Ala Tyr
65                  70                  75                  80

Val Glu Asp Phe Phe Thr Pro Trp Asp Arg Val Ala Ala Ala Arg Lys
                85                  90                  95

Pro Leu Ile Ala Ala Val Ser Gly Tyr Ala Leu Gly Gly Gly Cys Glu
            100                 105                 110

Leu Ala Met Leu Cys Asp Phe Ile Ile Ala Ser Asp Thr Ala Lys Phe
        115                 120                 125

Gly Gln Pro Glu Ile Lys Leu Gly Val Ile Pro Gly Ile Gly Gly Ser
    130                 135                 140

Gln Arg Leu Thr Arg Ala Val Gly Lys Ala Lys Ala Met Glu Leu Cys
145                 150                 155                 160

Leu Thr Gly Arg Asn Met Asp Ala Glu Glu Ala Glu Arg Ala Gly Leu

```
                165                 170                 175
Val Ala Arg Ile Val Pro Ala Ala Asp Leu Leu Asp Asp Ala Leu Lys
            180                 185                 190

Thr Ala Thr Thr Ile Ala Glu Met Ser Leu Pro Ile Ala Met Met Ala
        195                 200                 205

Lys Glu Ala Val Asn Arg Ser Phe Glu Thr Thr Leu Ala Glu Gly Val
    210                 215                 220

Arg Phe Glu Arg Arg Val Phe His Ser Thr Phe Ala Thr Glu Asp Gln
225                 230                 235                 240

Lys Glu Gly Met Thr Ala Phe Val Glu Lys Arg Ser Ala Glu Phe Lys
                245                 250                 255

His Arg

<210> SEQ ID NO 10
<211> LENGTH: 777
<212> TYPE: DNA
<213> ORGANISM: Rhodococcus erythropolis PR4(RE_echA)

<400> SEQUENCE: 10
gtgaccgact tcaacaccat catcctcgag cgtaagggtc gcgtcggcgt catcacgctc         60
aaccgcccga aggctctcaa cgccctgaac tccgagctga tgaacgaggt cgtcgccgcg        120
gttgccgacc tcgaagcgga caacggcatc ggagccatcc tgatcaccgg ttccgagcgc        180
gccttcgccg ccggcgccga catcaaggaa atgcagtcca agacgtacat ggacgcatac        240
gtcgaagatt tcttcacccc gtgggaccgc gtcgcagccg ctcgtaagcc gctgatcgcc        300
gccgtctccg gtacgcgct cggtggtggc tgcgaactgg cgatgctctg cgatttcatc         360
atcgcttcgg ataccgcgaa gttcggccag cccgagatca agctcggtgt cattccgggt        420
atcggtggct cacagcgcct acgcgcgcc gtgggtaagg ccaaggccat ggagctgtgc         480
ctgaccggcc gcaacatgga cgcagaagag gccgagcgcg caggcctggt tgcccggatc        540
gttccggccg ccgatctgct cgacgacgca ttgaagaccg caaccaccat cgccgagatg        600
tcgctgccca tcgcgatgat ggccaaggaa gcggtcaacc gttccttcga gaccacactc        660
gccgagggcg tccgcttcga gcgtcgggtg ttccactcga ccttcgcgac ggaggatcag        720
aaggaaggca tgaccgcgtt cgtggagaag cggtccgccg agttcaagca ccgctga         777

<210> SEQ ID NO 11
<211> LENGTH: 23
<212> TYPE: DNA
<213> ORGANISM: Artificial Sequence
<220> FEATURE:
<223> OTHER INFORMATION: MMA-044

<400> SEQUENCE: 11
gtttgcacgc ctgccgttcg acg                                                 23

<210> SEQ ID NO 12
<211> LENGTH: 23
<212> TYPE: DNA
<213> ORGANISM: Artificial Sequence
<220> FEATURE:
<223> OTHER INFORMATION: MMA-0045

<400> SEQUENCE: 12
cggtacgcgc ggatcttcca gag                                                 23

<210> SEQ ID NO 13
```

```
<211> LENGTH: 30
<212> TYPE: DNA
<213> ORGANISM: Artificial Sequence
<220> FEATURE:
<223> OTHER INFORMATION: MMA-003

<400> SEQUENCE: 13
gacccatgga tttcgacctc accgaagaac                                       30

<210> SEQ ID NO 14
<211> LENGTH: 31
<212> TYPE: DNA
<213> ORGANISM: Artificial Sequence
<220> FEATURE:
<223> OTHER INFORMATION: MMA-004

<400> SEQUENCE: 14
gccctgcagg atgcgatggt tcgcggcgtt c                                     31

<210> SEQ ID NO 15
<211> LENGTH: 31
<212> TYPE: DNA
<213> ORGANISM: Artificial Sequence
<220> FEATURE:
<223> OTHER INFORMATION: MMA-031

<400> SEQUENCE: 15
ggtcatgacc gacttcaaca ccatcatcct c                                     31

<210> SEQ ID NO 16
<211> LENGTH: 34
<212> TYPE: DNA
<213> ORGANISM: Artificial Sequence
<220> FEATURE:
<223> OTHER INFORMATION: MMA-032

<400> SEQUENCE: 16
ggcctgcagg ttcagctgtt cgaaagttca gcgc                                  34

<210> SEQ ID NO 17
<211> LENGTH: 26
<212> TYPE: DNA
<213> ORGANISM: Artificial Sequence
<220> FEATURE:
<223> OTHER INFORMATION: MAA-15

<400> SEQUENCE: 17
ggcctgtcat gagtgattac gagccg                                           26

<210> SEQ ID NO 18
<211> LENGTH: 32
<212> TYPE: DNA
<213> ORGANISM: Artificial Sequence
<220> FEATURE:
<223> OTHER INFORMATION: MAA-16

<400> SEQUENCE: 18
cggccctgca ggttcgcggg aatcagatgt gc                                    32

<210> SEQ ID NO 19
<211> LENGTH: 33
<212> TYPE: DNA
<213> ORGANISM: Artificial Sequence
<220> FEATURE:
<223> OTHER INFORMATION: GB-138

<400> SEQUENCE: 19
```
ggcctgcagg taccgatcat caccatcggt gtc                                    33

<210> SEQ ID NO 20
<211> LENGTH: 28
<212> TYPE: DNA
<213> ORGANISM: Artificial Sequence
<220> FEATURE:
<223> OTHER INFORMATION: GB-139

<400> SEQUENCE: 20
ggtctagact gagcagtgtt ccaatgcg                                          28

<210> SEQ ID NO 21
<211> LENGTH: 31
<212> TYPE: DNA
<213> ORGANISM: Artificial Sequence
<220> FEATURE:
<223> OTHER INFORMATION: GB-140

<400> SEQUENCE: 21
gaggaaatgg tcacagggcg agaataggtt g                                      31

<210> SEQ ID NO 22
<211> LENGTH: 29
<212> TYPE: DNA
<213> ORGANISM: Artificial Sequence
<220> FEATURE:
<223> OTHER INFORMATION: GB-141

<400> SEQUENCE: 22
gccctgtgac catttcctca ttgtgctgg                                         29

<210> SEQ ID NO 23
<211> LENGTH: 35
<212> TYPE: DNA
<213> ORGANISM: Artificial Sequence
<220> FEATURE:
<223> OTHER INFORMATION: MMA-061

<400> SEQUENCE: 23
cgactctaga ggatcgctca gtacatctac gagac                                  35

<210> SEQ ID NO 24
<211> LENGTH: 30
<212> TYPE: DNA
<213> ORGANISM: Artificial Sequence
<220> FEATURE:
<223> OTHER INFORMATION: MMA-062

<400> SEQUENCE: 24
agtgtgagga aagtgttccg atcagttcat                                        30

<210> SEQ ID NO 25
<211> LENGTH: 30
<212> TYPE: DNA
<213> ORGANISM: Artificial Sequence
<220> FEATURE:
<223> OTHER INFORMATION: MMA-063

<400> SEQUENCE: 25
cactttcctc acactcgtcg agagtatgag                                        30

<210> SEQ ID NO 26
<211> LENGTH: 35
<212> TYPE: DNA

<213> ORGANISM: Artificial Sequence
<220> FEATURE:
<223> OTHER INFORMATION: MMA-064

<400> SEQUENCE: 26
cggtacccgg ggatcagcgc gacgaacaac gagac                                35

<210> SEQ ID NO 27
<211> LENGTH: 22
<212> TYPE: DNA
<213> ORGANISM: Artificial Sequence
<220> FEATURE:
<223> OTHER INFORMATION: MMA-069

<400> SEQUENCE: 27
gcgcatctac aaggaagaga tc                                              22

<210> SEQ ID NO 28
<211> LENGTH: 20
<212> TYPE: DNA
<213> ORGANISM: Artificial Sequence
<220> FEATURE:
<223> OTHER INFORMATION: MMA-070

<400> SEQUENCE: 28
gcgacgctca tcgagatctc                                                 20

<210> SEQ ID NO 29
<211> LENGTH: 36
<212> TYPE: DNA
<213> ORGANISM: Artificial Sequence
<220> FEATURE:
<223> OTHER INFORMATION: MMA-133

<400> SEQUENCE: 29
tgacctgcag gtgcactccg ctgcgacatg tatcga                               36

<210> SEQ ID NO 30
<211> LENGTH: 45
<212> TYPE: DNA
<213> ORGANISM: Artificial Sequence
<220> FEATURE:
<223> OTHER INFORMATION: MMA-131

<400> SEQUENCE: 30
actctagcct gcaggtcatt gactagttga tctaaggttg ttaca                     45

<210> SEQ ID NO 31
<211> LENGTH: 1520
<212> TYPE: DNA
<213> ORGANISM: Rhodococcus erythropolis PR4

<400> SEQUENCE: 31
tcaacggaga gtttgatcct ggctcaggac gaacgctggc ggcgtgctta acacatgcaa     60
gtcgagcggt aaggcctttc ggggtacacg agcggcgaac gggtgagtaa cacgtgggtg    120
atctgccctg cacttcggga taagcctggg aaactgggtc taataccgga tatgacctca    180
ggttgcatga cttggggtgg aaagatttat cggtgcagga tgggcccgcg gcctatcagc    240
ttgttggtgg ggtaatggcc taccaaggcg acgacgggta gccgacctga gagggtgacc    300
ggccacactg gactgagaca cggcccaga ctcctacggg aggcagcagt ggggaatatt    360
gcacaatggg cgaaagcctg atgcagcgac gccgcgtgag ggatgacggc cttcgggttg    420
taaacctctt tcagcaggga cgaagcgcaa gtgacggtac ctgcagaaga agcaccggct    480

-continued

```
aactacgtgc cagcagccgc ggtaatacgt agggtgcaag cgttgtccgg aattactggg    540
cgtaaagagt tcgtaggcgg tttgtcgcgt cgtttgtgaa aaccagcagc tcaactgctg    600
gcttgcaggc gatacgggca gacttgagta ctgcagggga gactggaatt cctggtgtag    660
cggtgaaatg cgcagatatc aggaggaaca ccggtggcga aggcgggtct ctgggcagta    720
actgacgctg aggaacgaaa gcgtgggtag cgaacaggat tagatacccct ggtagtccac    780
gccgtaaacg gtgggcgcta ggtgtgggtt ccttccacgg aatccgtgcc gtagctaacg    840
cattaagcgc cccgcctggg gagtacggcc gcaaggctaa aactcaaagg aattgacggg    900
ggcccgcaca gcggcggag catgtggatt aattcgatgc aacgcgaaga accttacctg    960
ggtttgacat ataccggaaa gctgcagaga tgtggcccccc cttgtggtcg gtatacaggt   1020
ggtgcatggc tgtcgtcagc tcgtgtcgtg agatgttggg ttaagtcccg caacgagcgc   1080
aaccccctatc ttatgttgcc agcacgttat ggtggggact cgtaagagac tgccggggtc   1140
aactcggagg aaggtgggga cgacgtcaag tcatcatgcc ccttatgtcc agggcttcac   1200
acatgctaca atggccagta cagagggctg cgagaccgtg aggtggagcg aatcccttaa   1260
agctggtctc agttcggatc ggggtctgca actcgacccc gtgaagtcgg agtcgctagt   1320
aatcgcagat cagcaacgct gcggtgaata cgttcccggg ccttgtacac accgcccgtc   1380
acgtcatgaa agtcggtaac acccgaagcc ggtggcttaa ccccttgtgg gagggagccg   1440
tcgaaggtgg gatcggcgat tgggacgaag tcgtaacaag gtagccgtac cggaaggtgc   1500
ggctggatca cctcctttct                                               1520
```

<210> SEQ ID NO 32
<211> LENGTH: 386
<212> TYPE: PRT
<213> ORGANISM: Rhodococcus erythropolis PR4 RE_Acd1

<400> SEQUENCE: 32

```
Met Phe Thr Leu Thr Asp Asp Glu Arg Ala Ile Arg Asp Thr Ala Arg
1               5                   10                  15

Asp Phe Ala Ala Glu His Leu Ala Pro Asn Ala Val Glu Trp Asp Gln
            20                  25                  30

Thr Lys His Phe Pro Val Asp Val Leu Arg Lys Ala Ala Ser Leu Gly
        35                  40                  45

Met Gly Gly Ile Tyr Ile Arg Glu Asp Val Gly Ser Glu Leu Ser
    50                  55                  60

Arg Val Asp Ala Ala Arg Ile Phe Glu Glu Leu Ala Lys Gly Asp Pro
65                  70                  75                  80

Ser Ile Ala Ala Tyr Ile Ser Ile His Asn Met Val Thr Trp Met Ile
                85                  90                  95

Asp Gln Phe Gly Asn Asp Glu Gln Arg His Lys Trp Val Pro Gly Leu
            100                 105                 110

Cys Ser Met Asp Gln Leu Gly Ser Tyr Cys Leu Thr Glu Pro Gly Ala
        115                 120                 125

Gly Ser Asp Ala Ala Gly Leu Ser Thr Lys Ala Val Arg Asp Gly Asp
    130                 135                 140

Asp Tyr Ile Leu Asn Gly Val Lys Gln Phe Ile Ser Gly Ala Gly Thr
145                 150                 155                 160

Ser Asp Val Tyr Val Val Met Ala Arg Thr Gly Ser Ala Gly Ala Lys
                165                 170                 175

Gly Ile Ser Ala Phe Ile Val Pro Lys Asp Ser Pro Gly Leu Ser Phe
```

|  | 180 |  |  | 185 |  |  |  | 190 |  |  |
|---|---|---|---|---|---|---|---|---|---|---|

Gly Ala Asn Glu Val Lys Met Gly Trp Asn Ala Gln Pro Thr Arg Gln
        195                200                205

Val Ile Phe Glu Asp Val Arg Val Pro Ala Ala Asn Met Leu Gly Glu
210                  215                220

Glu Gly Ser Gly Phe Arg Ile Ala Met Lys Gly Leu Asn Gly Gly Arg
225                230                235               240

Leu Asn Ile Ala Ala Cys Ser Val Gly Gly Ala Gln Ala Ala Leu Glu
        245                250                255

Lys Ala Val Ala Tyr Leu Val Asp Arg Lys Ala Phe Gly Ser Ala Leu
            260                265               270

Ile Glu Ser Gln Ala Leu Gln Phe Gln Leu Ala Asp Met Arg Thr Glu
        275                280               285

Leu Glu Ala Ala Arg Thr Leu Leu Trp Arg Ala Ala Ala Ala Leu Glu
           290                295               300

Asp Gly Ala Ser Asp Val Val Glu Leu Cys Ala Met Ala Lys Arg Phe
305                  310                315               320

Ala Thr Asp Thr Gly Phe Asp Val Ala Asn Lys Ala Leu Gln Leu His
                325              330               335

Gly Gly Tyr Gly Tyr Leu Ala Glu Tyr Gly Ile Glu Lys Ile Val Arg
            340                345               350

Asp Leu Arg Val His Gln Ile Leu Glu Gly Ser Asn Glu Ile Met Arg
        355                360               365

Val Val Ile Ala Arg Ser Val Val Ala Ser Gly Gln Gly Lys Gln Gly
370                  375                380

Ala Ala
385

```
<210> SEQ ID NO 33
<211> LENGTH: 1161
<212> TYPE: DNA
<213> ORGANISM: Rhodococcus erythropolis PR4 RE_Acd1

<400> SEQUENCE: 33
```

| | | |
|---|---|---|
| atgtttactc tgaccgatga cgagcgggcg attcgcgaca ctgcccgcga cttcgcggcc | 60 |
| gagcatctgg cgcccaacgc agtggagtgg atcagacca agcatttccc ggtggacgtc | 120 |
| ctccgtaagg cggcgtccct ggggatgggc ggtatctaca ttcgtgagga cgtgggcggc | 180 |
| agtgagctga ccgcgtcga cgctgcccgg atcttcgaag agctggccaa gggcgatccg | 240 |
| tcgatcgccg cgtacatctc catccacaac atggtcacgt ggatgatcga ccagttcggc | 300 |
| aacgacgaac agcgccacaa gtgggtcccc ggactctgct cgatggatca actgggcagc | 360 |
| tactgcctca ccgaacccgg cgctggctcc gatgctgcgg gcttgagcac caaggccgtt | 420 |
| cgtgacggcg acgactacat cctcaacggc gtcaaacagt tcatttccgg cgcaggcact | 480 |
| tccgacgtgt acgtcgtgat ggcacgcacc ggatctgccg gtgccaaggg gatctcggcg | 540 |
| ttcatcgtgc ccaaggattc gcccggactg tcgttcggtg ccaacgaggt caagatgggc | 600 |
| tggaacgcgc agcccacccg tcaggtgatc ttcgaagacg tgcgagttcc tgccgccaac | 660 |
| atgctcggtg aagagggcag cggcttccgc atcgctatga agggtctcaa cggcggccgg | 720 |
| ctgaacatcg ccgcctgctc ggtcggtggg gcccaggcag cgctggagaa ggcagtcgca | 780 |
| tatctggtgg accgcaaagc tttcggttcg gcactgatcg agtcgcaggc cctgcagttc | 840 |
| cagctcgccg acatgcgtac cgaactcgaa gcggccagga cgttgctgtg gcgcgccgct | 900 |

```
gccgcactcg aagacggagc gtccgacgtc gtggagttgt gtgcgatggc caagcgcttt      960
gccaccgaca ccgggttcga cgtagccaac aaggctctcc agcttcacgg cgggtacggc     1020
tatcttgctg agtacgggat cgagaagatc gtccgcgatc ttcgggttca tcagatcctc     1080
gaaggcagca acgagatcat gagggtggtc atcgcgcgaa gcgtggtcgc atcaggtcag     1140
ggaaagcaag gagcagcatg a                                               1161

<210> SEQ ID NO 34
<211> LENGTH: 1578
<212> TYPE: DNA
<213> ORGANISM: Saccharomyces cerevisiae

<400> SEQUENCE: 34
atgaatgaaa tcgatgagaa aaatcaggcc cccgtgcaac aagaatgcct gaaagagatg       60
attcagaatg gcatgctcg gcgtatggga tctgttgaag atctgtatgt tgctctcaac      120
agacaaaact tatatcgaaa cttctgcaca tatggagaat tgagtgatta ctgtactagg      180
gatcagctca cattagcttt gagggaaatc tgcctgaaaa atccaactct tttacatatt      240
gttctaccaa caagatggcc aaatcatgaa attattatc gcagttccga atactattca      300
cggccacatc cagtgcatga ttatatttca gtattacaag aattgaaact gagtggtgtg      360
gttctcaatg aacaacctga gtacagtgca gtaatgaagc aaatattaga agaattcaaa      420
aatagtaagg gttcctatac tgcaaaaatt tttaaactta ctaccacttt gactattcct      480
tactttggac caacaggacc gagttggcgg ctaatttgtc ttccagaaga gcacacagaa      540
aagtggaaaa aatttatctt tgtatctaat cattgcatgt ctgatggtcg gtcttcgatc      600 cactttttttc atgatttaag agacgaatta aataatatta aactccacc aaaaaaatta      660 gattacattt tcaagtacga ggaggattac caattattga ggaaacttcc agaaccgatc      720
gaaaaggtga tagactttag accaccgtac ttgtttattc cgaagtcact tctttcgggt      780
ttcatctaca atcatttgag attttcttca aaaggtgtct gtatgagaat ggatgatgtg      840
gaaaaaaccg atgatgttgt caccgagatc atcaatattt caccaacaga atttcaagcg      900
attaaagcaa atattaaatc aaatatccaa ggtaagtgta ctatcactcc gtttttacat      960
gtttgttggt ttgtatctct tcataaatgg ggtaaatttt tcaaaccatt gaacttcgaa     1020
tggcttacgg atattttat ccccgcagat tgccgctcac aactaccaga tgatgatgaa      1080
atgagacaga tgtacagata tggcgctaac gttggattta ttgacttcac ccctggata      1140 agcgaatttg acatgaatga taacaaagaa aatttttggc cacttattga gcactaccat     1200
gaagtaattt cggaagcttt aagaaataaa aagcatctcc atggcttagg gttcaatata     1260
caaggcttcg ttcaaaaata tgtgaacatt gacaaggtaa tgtgcgatcg tgccatcggg     1320
aaaagacgcg gaggtacatt gttaagcaat gtaggtctgt taatcagtt agaggagccc      1380 gatgccaaat attctatatg cgatttggca tttggccaat tcaaggatc ctggcaccaa     1440 gcatttttcct tgggtgtttg ttcgactaat gtaaggggga tgaatattgt tgttgcttca    1500
acaaagaatg ttgttggtag tcaagaatct ctcgaagagc tttgctccat ttacaaagct    1560 ctcctttttag gcccttag                                                 1578

<210> SEQ ID NO 35
<211> LENGTH: 525
<212> TYPE: PRT
<213> ORGANISM: Saccharomyces cerevisiae

<400> SEQUENCE: 35
```

-continued

```
Met Asn Glu Ile Asp Glu Lys Asn Gln Ala Pro Val Gln Gln Glu Cys
1               5                   10                  15

Leu Lys Glu Met Ile Gln Asn Gly His Ala Arg Arg Met Gly Ser Val
                20                  25                  30

Glu Asp Leu Tyr Val Ala Leu Asn Arg Gln Asn Leu Tyr Arg Asn Phe
            35                  40                  45

Cys Thr Tyr Gly Glu Leu Ser Asp Tyr Cys Thr Arg Asp Gln Leu Thr
        50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95

Glu Tyr Tyr Ser Arg Pro His Pro Val His Asp Tyr Ile Ser Val Leu
            100                 105                 110

Gln Glu Leu Lys Leu Ser Gly Val Val Leu Asn Glu Gln Pro Glu Tyr
        115                 120                 125

Ser Ala Val Met Lys Gln Ile Leu Glu Glu Phe Lys Asn Ser Lys Gly
    130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
            180                 185                 190

Met Ser Asp Gly Arg Ser Ser Ile His Phe Phe His Asp Leu Arg Asp
        195                 200                 205

Glu Leu Asn Asn Ile Lys Thr Pro Pro Lys Lys Leu Asp Tyr Ile Phe
210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
            260                 265                 270

Val Cys Met Arg Met Asp Asp Val Glu Lys Thr Asp Asp Val Val Thr
        275                 280                 285

Glu Ile Ile Asn Ile Ser Pro Thr Glu Phe Gln Ala Ile Lys Ala Asn
290                 295                 300

Ile Lys Ser Asn Ile Gln Gly Lys Cys Thr Ile Thr Pro Phe Leu His
305                 310                 315                 320

Val Cys Trp Phe Val Ser Leu His Lys Trp Gly Lys Phe Phe Lys Pro
                325                 330                 335

Leu Asn Phe Glu Trp Leu Thr Asp Ile Phe Ile Pro Ala Asp Cys Arg
            340                 345                 350

Ser Gln Leu Pro Asp Asp Asp Glu Met Arg Gln Met Tyr Arg Tyr Gly
        355                 360                 365

Ala Asn Val Gly Phe Ile Asp Phe Thr Pro Trp Ile Ser Glu Phe Asp
370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys Lys His Leu His Gly Leu
                405                 410                 415
```

```
Gly Phe Asn Ile Gln Gly Phe Val Gln Lys Tyr Val Asn Ile Asp Lys
                420                 425                 430
Val Met Cys Asp Arg Ala Ile Gly Lys Arg Arg Gly Gly Thr Leu Leu
            435                 440                 445
Ser Asn Val Gly Leu Phe Asn Gln Leu Glu Glu Pro Asp Ala Lys Tyr
        450                 455                 460
Ser Ile Cys Asp Leu Ala Phe Gly Gln Phe Gln Gly Ser Trp His Gln
465                 470                 475                 480
Ala Phe Ser Leu Gly Val Cys Ser Thr Asn Val Lys Gly Met Asn Ile
                485                 490                 495
Val Val Ala Ser Thr Lys Asn Val Val Gly Ser Gln Glu Ser Leu Glu
            500                 505                 510
Glu Leu Cys Ser Ile Tyr Lys Ala Leu Leu Leu Gly Pro
        515                 520                 525
```

<210> SEQ ID NO 36
<211> LENGTH: 1608
<212> TYPE: DNA
<213> ORGANISM: Saccharomyces cerevisiae

<400> SEQUENCE: 36

```
atggaagata tagaaggata cgaaccacat atcactcaag agttgataga ccgtggccat      60
gcaagacgta tgggccactt ggaaaactac tttgctgttt tgagtaggca gaaaatgtac     120
tcgaatttta ctgtttacgc ggaattgaat aaaggtgtta ataagagaca actaatgctt     180
gtcttgaaag tattacttca aaaatactca actcttgcgc atacaatcat tcctaagcat     240
tatcctcatc atgaagcgta ctactctagc gaagagtacc ttagtaaacc ttttccacag     300
catgatttca taaggtgat ttctcatctt gaattcgatg acttgattat gaataatcaa     360
ccagaataca gagaagtcat ggagaaaatc tcagaacagt tcaaaaagga tgatttcaaa     420
gtcaccaata ggttaatcga attgattagc cctgtaatca tacctctggg taatccgaag     480
aggcctaatt ggagattgat tgtttaccaa ggtaaggata ctgatgggtt tgaaacgtgg     540
aaaaacttcg tttatgtcac taaccactgc ggctccgacg gtgtcagtgg atcgaatttt     600
ttcaaagatt tagctctact ctttgtaaa atcgaagaaa aagggtttga ttatgatgaa     660
gagttcatcg aagatcaagt catcattgac tatgatcgag actacactga aatttctaaa     720
ttgccaaaac cgattacgga tcgtattgac tacaagccag cattgacttc attacccaaa     780
ttcttttaa caaccttcat ttatgaacat tgtaatttta aaacctccag cgaatctaca     840
cttacagcta gatatagccc ctctagtaat gctaatgcta gttacaatta cttgttgcat     900
ttcagtacta agcaagtaga acaaatcaga gctcagatca agaaaaatgt tcacgatggg     960
tgcacccta cacccttcat tcaagcgtgc tttcttgtag ccctgtatag actggataag    1020
ctgttcacaa atctcttct cgagtatggg ttcgatgtgg ctattccaag caacgcaaga    1080
aggttttac caaacgatga agagttaaga gattcttata atacggctc aacgttgga    1140
ggttcgcatt acgcctatct aatctcctca ttcgacattc ccgaaggtga caatgacaag    1200
ttttggagtc ttgtcgaata ctactatgac cgcttttag aatcgtacga caacggtgac    1260
cacttgattg gtctgggggt cctacaactt gattttatc ttgaaaacaa gaatatagac    1320
agccttcttg ccaactctta tttgcaccag caaagaggcg gtgcaatcat cagtaataca    1380
ggacttgtct cgcaagatac gaccaagccg tactacgttc gggattaat cttctcgcag    1440
tctgcaggcg ccttgagatt tgcgttcggc ctaaacgttt gctccacaaa cgtgaatggt    1500
```

```
atgaacatgg acatgagcgt ggttcagggc actctacggg atcgtggcga atgggaatcg    1560
ttctgcaagc tcttctacca aaccatcggc gaatttgcgt cgctttaa                1608
```

<210> SEQ ID NO 37
<211> LENGTH: 535
<212> TYPE: PRT
<213> ORGANISM: Saccharomyces cerevisiae

<400> SEQUENCE: 37

```
Met Glu Asp Ile Glu Gly Tyr Glu Pro His Ile Thr Gln Glu Leu Ile
1               5                   10                  15

Asp Arg Gly His Ala Arg Arg Met Gly His Leu Glu Asn Tyr Phe Ala
            20                  25                  30

Val Leu Ser Arg Gln Lys Met Tyr Ser Asn Phe Thr Val Tyr Ala Glu
        35                  40                  45

Leu Asn Lys Gly Val Asn Lys Arg Gln Leu Met Leu Val Leu Lys Val
    50                  55                  60

Leu Leu Gln Lys Tyr Ser Thr Leu Ala His Thr Ile Ile Pro Lys His
65                  70                  75                  80

Tyr Pro His His Glu Ala Tyr Tyr Ser Ser Glu Glu Tyr Leu Ser Lys
                85                  90                  95

Pro Phe Pro Gln His Asp Phe Ile Lys Val Ile Ser His Leu Glu Phe
            100                 105                 110

Asp Asp Leu Ile Met Asn Asn Gln Pro Glu Tyr Arg Glu Val Met Glu
        115                 120                 125

Lys Ile Ser Glu Gln Phe Lys Lys Asp Phe Lys Val Thr Asn Arg
    130                 135                 140

Leu Ile Glu Leu Ile Ser Pro Val Ile Pro Leu Gly Asn Pro Lys
145                 150                 155                 160

Arg Pro Asn Trp Arg Leu Ile Cys Leu Pro Gly Lys Asp Thr Asp Gly
                165                 170                 175

Phe Glu Thr Trp Lys Asn Phe Val Tyr Val Thr Asn His Cys Gly Ser
            180                 185                 190

Asp Gly Val Ser Gly Ser Asn Phe Phe Lys Asp Leu Ala Leu Leu Phe
        195                 200                 205

Cys Lys Ile Glu Glu Lys Gly Phe Asp Tyr Asp Glu Phe Ile Glu
    210                 215                 220

Asp Gln Val Ile Ile Asp Tyr Asp Arg Asp Tyr Thr Glu Ile Ser Lys
225                 230                 235                 240

Leu Pro Lys Pro Ile Thr Asp Arg Ile Asp Tyr Lys Pro Ala Leu Thr
                245                 250                 255

Ser Leu Pro Lys Phe Phe Leu Thr Thr Phe Ile Tyr Glu His Cys Asn
            260                 265                 270

Phe Lys Thr Ser Ser Glu Ser Thr Leu Thr Ala Arg Tyr Ser Pro Ser
        275                 280                 285

Ser Asn Ala Asn Ala Ser Tyr Asn Tyr Leu Leu His Phe Ser Thr Lys
    290                 295                 300

Gln Val Glu Gln Ile Arg Ala Gln Ile Lys Lys Asn Val His Asp Gly
305                 310                 315                 320

Cys Thr Leu Thr Pro Phe Ile Gln Ala Cys Phe Leu Val Ala Leu Tyr
                325                 330                 335

Arg Leu Asp Lys Leu Phe Thr Lys Ser Leu Leu Glu Tyr Gly Phe Asp
            340                 345                 350

Val Ala Ile Pro Ser Asn Ala Arg Arg Phe Leu Pro Asn Asp Glu Glu
```

```
                    355                 360                 365
Leu Arg Asp Ser Tyr Lys Tyr Gly Ser Asn Val Gly Gly Ser His Tyr
    370                 375                 380

Ala Tyr Leu Ile Ser Ser Phe Asp Ile Pro Glu Gly Asp Asn Asp Lys
385                 390                 395                 400

Phe Trp Ser Leu Val Glu Tyr Tyr Tyr Asp Arg Phe Leu Glu Ser Tyr
                405                 410                 415

Asp Asn Gly Asp His Leu Ile Gly Leu Gly Val Leu Gln Leu Asp Phe
                420                 425                 430

Ile Val Glu Asn Lys Asn Ile Asp Ser Leu Leu Ala Asn Ser Tyr Leu
            435                 440                 445

His Gln Gln Arg Gly Gly Ala Ile Ile Ser Asn Thr Gly Leu Val Ser
        450                 455                 460

Gln Asp Thr Thr Lys Pro Tyr Tyr Val Arg Asp Leu Ile Phe Ser Gln
465                 470                 475                 480

Ser Ala Gly Ala Leu Arg Phe Ala Phe Gly Leu Asn Val Cys Ser Thr
                485                 490                 495

Asn Val Asn Gly Met Asn Met Asp Met Ser Val Val Gln Gly Thr Leu
                500                 505                 510

Arg Asp Arg Gly Glu Trp Glu Ser Phe Cys Lys Leu Phe Tyr Gln Thr
            515                 520                 525

Ile Gly Glu Phe Ala Ser Leu
            530                 535
```

METHOD FOR PRODUCING METHACRYLIC ACID ESTER

TECHNICAL FIELD

The present invention relates to a method for producing methacrylic acid ester using a biocatalyst.

BACKGROUND ART

Methacrylic acid esters are primarily used as raw material in acrylic resins, and there are many demands also as a monomer in fields such as paints, adhesives, and resin modifiers. There are a few methods as industrial manufacturing methods and, for example, the ACH (acetone cyano hydrin) method using acetone and hydrogen cyanide as raw materials, and the direct oxidation method using isobutylene and tert-butyl alcohol as raw materials have been known. These chemical production methods depend on fossil raw materials, and require great deal of energy.

In recent years, technologies for producing various chemicals from biomass as a carbon source substituting conventional fossil raw materials has been given attention from the viewpoints of prevention of global warming and environmental protection. Although the production from biomass raw material is also being expected for methacrylic acid esters, a specific production example from biomass raw materials using a biocatalyst has not been reported.

For example, methods utilizing microorganisms existing in nature to produce 2-hydroxyisobutyric acid and 3-hydroxyisobutyric acid serving precursors of methacrylic acid from a natural source such as sugar have been proposed (refer to Patent Documents 1 and 2, and Non-Patent Document 1). However, in these methods, the processes for dehydrating precursor and forming methacrylic acid still depend on chemical techniques.

In addition, although methods of forming methacrylic acid from glucose using recombinant microorganisms that do not exist in nature and are produced by introducing a plurality of enzyme genes have been proposed, these combine an already known enzyme reaction and a theoretical enzyme reaction analogized from this, and thus have not been proven (refer to Patent Documents 3 to 5). In particular, Patent Document 5 exemplifies various biocatalysts (hydrolase, wax ester synthetase, alcohol acetyltransferase) having general ester formation activity; however, it is unclear whether the exemplified biocatalysts have synthetic activity for methacrylic acid ester.

Furthermore, Patent Document 6 discloses a method for producing acrylic acid ester by causing hydrolase to function under the presence of acrylyl-CoA and alcohol. The same document suggests that production is similarly possible also for methacrylic acid esters. However, when taking account of the diversity and substrate specificity of biocatalysts, it merely illustrates that the production of a part of acrylic acid esters is possible with hydrolase, and it is unclear whether methacrylic acid esters having a different structure are similarly producible by hydrolase. Furthermore, it is completely unclear whether it is possible to produce with other types of biocatalysts having different reaction mechanisms. In addition, in the case of synthesizing esters by the hydrolase described in Patent Document 6, it is assumed that the formed ester will be decomposed by the hydrolysis activity in the first place, and thus is quite unlikely as an effective production method.

On the other hand, alcohol acetyltransferase has been known as a fruity flavor synthetase. Identifying the same enzyme genes contained in specific fruits, Patent Document 7 proposes synthesis methods of various esters that are fruit flavors. However, it has not been reported whether methacrylic acid esters are synthesizable with these enzymes, and has been completely unclear.

As stated above, although a few proposals or studies have been made, there are no examples of actually producing methacrylic acid derivatives by way of microorganisms, and thus the establishment of an effective production method has been desired.

[Patent Document 1] Pamphlet of PCT International Publication No. WO2007/110394
[Patent Document 2] Pamphlet of PCT International Publication No. WO2008/145737
[Patent Document 3] Pamphlet of PCT International Publication No. WO2009/135074
[Patent Document 4] Pamphlet of PCT International Publication No. WO2011/031897
[Patent Document 5] Pamphlet of PCT International Publication No. WO2012/135789
[Patent Document 6] Pamphlet of PCT International Publication No. WO2007/039415
[Patent Document 7] Pamphlet of PCT International Publication No. WO2000/32789
[Patent Document 8] Japanese Unexamined Patent Application, Publication No. 2011-200133
[Patent Document 9] Japanese Unexamined Patent Application, Publication No. H05-64589
[Patent Document 10] Japanese Unexamined Patent Application, Publication No. H10-337185
[Patent Document 11] Japanese Unexamined Patent Application, Publication No. H10-24867
[Non-Patent Document 1] Green Chemistry, 2012, 14, 1942-1948
[Non-Patent Document 2] Methods in Enzymology, 2000, 324, 73-79
[Non-Patent Document 3] Botanical Journal of the Linnean Society, 2009, 161, 105-121
[Non-Patent Document 4] Microbiology, 1999, 145, 2323-2334

DISCLOSURE OF THE INVENTION

Problems to be Solved by the Invention

The present invention has an object of providing a method for producing methacrylic acid ester by way of a biocatalyst.

Means for Solving the Problems

It has been found that alcohol acyltransferase has activity for synthesizing methacrylic acid esters, thereby arriving at completion of the present invention. More specifically, the present invention is as follows.

According to a first aspect of the invention, a method for producing methacrylic acid ester includes a step of synthesizing methacrylic acid ester by causing an alcohol or phenol to act on methacrylyl-CoA under the presence of an alcohol acyltransferase.

According to a second aspect of the invention, in the method for producing methacrylic acid ester as described in the first aspect, the methacrylic acid ester is accumulated in at least 0.001 mM.

According to a third aspect of the invention, the method for producing methacrylic acid ester as described in the first or second aspect further includes a step of producing methacrylyl-CoA from isobutyryl-CoA or 3-hydroxyisobutyryl-CoA.

According to a fourth aspect of the invention, in the method for producing methacrylic acid ester as described in the third aspect, the isobutyryl-CoA is produced from 2-oxoisovaleric acid.

According to a fifth aspect of the invention, in the method for producing methacrylic acid ester as described in any one of the first to fourth aspects, the alcohol acyltransferase is of plant origin.

According to a sixth aspect of the invention, in the method for producing methacrylic acid ester as described in the fifth aspect, the plant belongs to any order selected from the group consisting of Zingiberales, Rosales, Ericales, Cucurbitales, Brassicales and Laurales.

According to a seventh aspect of the invention, in the method for producing methacrylic acid ester as described in the fifth aspect, the plant belongs to any family selected from the group consisting of Musaceae, Rosaceae, Ericaceae, Actinidiaceae, Cucurbitaceae, Caricaceae and Lauraceae.

According to an eighth aspect of the invention, in the method for producing methacrylic acid ester as described in the fifth aspect, the plant belongs to any genus selected from the group consisting of *Musa, Fragaria, Malus, Prunus, Pyrus, Vaccinium, Actinidia, Cucumis, Carica* and *Persea*.

According to a ninth aspect of the invention, in the method for producing methacrylic acid ester as described in the fifth aspect, the plant is any genus selected from *Musa, Malus, Prunus, Pyrus, Vaccinium, Actinidia, Cucumis, Carica* and *Persea*.

According to a tenth aspect of the invention, in the method for producing methacrylic acid ester as described in the fifth aspect, the plant is any genus selected from *Musa, Malus, Pyrus, Actinidia, Cucumis, Carica* and *Persea*.

According to an eleventh aspect of the invention, in the method for producing methacrylic acid ester as described in the fifth aspect, the plant is any one selected from the group consisting of banana, strawberry, apple, *Prunus mume*, *Pyrus communis*, blueberry, kiwi, melon, papaya and avocado.

According to a twelfth aspect of the invention, in the method for producing methacrylic acid ester as described in the fifth aspect, the plant is any one selected from the group consisting of banana, apple, *Prunus mume*, *Pyrus communis*, blueberry, kiwi, melon, papaya and avocado.

According to a thirteenth aspect of the invention, in the method for producing methacrylic acid ester as described in the fifth aspect, the plant is any one selected from the group consisting of banana, apple, *Pyrus communis*, kiwi, melon, papaya and avocado.

According to a fourteenth aspect of the invention, the method for producing methacrylic acid ester as described in any of the first to thirteenth aspects uses a genetically modified microorganism that has been gene transferred so as to express alcohol acyltransferase.

In addition, the present invention is as follows in another aspect.

According to a fifteenth aspect of the invention, a method for producing methacrylic acid ester produces the methacrylic acid ester using a microorganism belonging to *Rhodococcus* genus.

According to a sixteenth aspect of the invention, the method for producing methacrylic acid ester as described in the fifteenth aspect uses a microorganism belonging to the *Rhodococcus* genus having 16SrDNA that includes a nucleotide sequence having at least 95% identity to the nucleotide sequence of 16SrDNA shown in SEQ ID NO. 31.

According to a seventeenth aspect of the invention, in the method for producing methacrylic acid ester as described in the fifteenth or sixteenth aspect, the microorganism belonging to *Rhodococcus* genus is *Rhodococcus erythropolis*.

According to an eighteenth aspect of the invention, the method for producing methacrylic acid ester as described in the fifteenth or sixteenth aspect uses a derivative strain of the microorganism as the microorganism belonging to *Rhodococcus* genus.

According to a nineteenth aspect of the invention, in the method for producing methacrylic acid ester as described in the eighteenth aspect, the microorganism belonging to *Rhodococcus* genus is *Rhodococcus erythropolis* PR-4 strain or a derivative strain thereof.

According to a twentieth aspect of the invention, in the method for producing methacrylic acid ester as described in the eighteenth aspect, the derivative strain is a genetically modified strain having a modification of at least one of (a) or (b) shown below.

(a) Modification by introduction of branched ketoacid dehydrogenase gene and/or acyl-CoA dehydrogenase gene (b) Modification of deleting or inactivating enoyl-CoA hydratase gene, 3-hydroxyisobutyryl-CoA hydratase gene and/or 3-hydroxyisobutyric acid dehydrogenase gene.

According to a twenty-first aspect of the invention, in the method for producing methacrylic acid ester as described in the nineteenth or twentieth aspect, the derivative strain has a plasmid for alcohol acyltransferase and/or acyl-CoA dehydrogenase expression.

Effects of the Invention

By way of the present invention, the production of methacrylic acid ester by way of a biocatalyst becomes possible. By combining the production method of the present invention with in vivo metabolism, fermentative production of methacrylic acid ester can also be achieved. As a result thereof, the energy, resources and load on the environment can be remarkably reduced compared to a conventional chemical production process, and it becomes possible to efficiently produce methacrylic acid ester.

EMBODIMENTS FOR CARRYING OUT THE INVENTION

Figure 1:
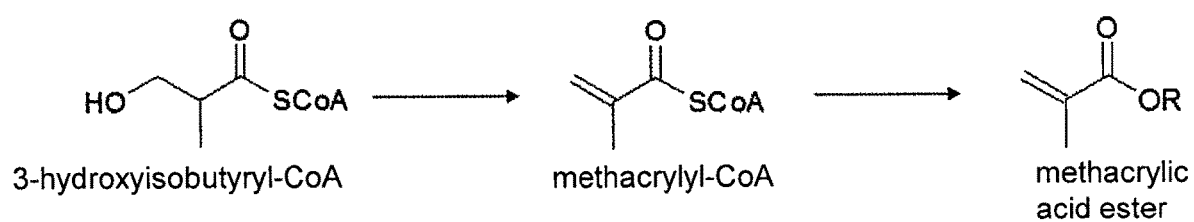
FIG. 1 is a view showing the production steps from 3-hydroxyisobutyryl-CoA to methacrylic acid ester.

Hereinafter, preferred modes for carrying out the present invention will be explained while referencing the drawings. It should be noted that the embodiments explained in the following are arrived at by expressing examples of representative embodiments of the present invention, and the scope of the present invention is not to be narrowly interpreted therefrom.

1. Production Method of Methacrylic Acid Ester from Alcohol Acyltransferase

Methacrylic Acid Ester

In the present invention, methacrylic acid ester is a compound expressed by Formula 1. In Formula 1, R represents a linear or branched C1-20 hydrocarbon group. The hydrocarbon group may be of saturated or unsaturated non-cyclic type, or may be of saturated or unsaturated cyclic type. It is preferably a linear or branched C1-10 unsubstituted alkyl group, aralkyl group or aryl group. It is more preferably a C1-8 alkyl group such as a methyl group, ethyl group, n-propyl group, isopropyl group, n-butyl group, isobutyl group, sec-butyl group, tert-butyl group, n-pentyl group, isopentyl group, tert-pentyl group, n-hexyl group, isohexyl group, 2-hexyl group, dimethylbutyl group, ethylbutyl group, heptyl group, octyl group, 2-ethylhexyl group; a benzyl group or a phenyl group.

$$CH_2=C(CH_3)COO-R \quad \text{(Formula 1)}$$

"Methacrylic acid" (IUPAC name: 2-methyl-2-propenoic acid) indicates a compound having the formula below, and also includes any salts or ionized forms thereof. As salts of methacrylic acid, for example, sodium salts, potassium salts, calcium salts, magnesium salts, etc. can be exemplified.

$$CH_2=C(CH_3)COOH$$

Methacrylyl-CoA

In the present invention, methacrylyl-CoA is a compound expressed by the structural formula below. Methacrylyl-CoA is known as a metabolic intermediate of valine within organisms. The methacrylyl-CoA used in the present invention can be that produced by a known or novel method. As the synthesis method thereof, the method of organochemically synthesizing coenzyme A with methacrylic anhydride (Methods in Enzymology, 324, 73-79 (2000)) or a synthesis method using an enzyme reaction are known.

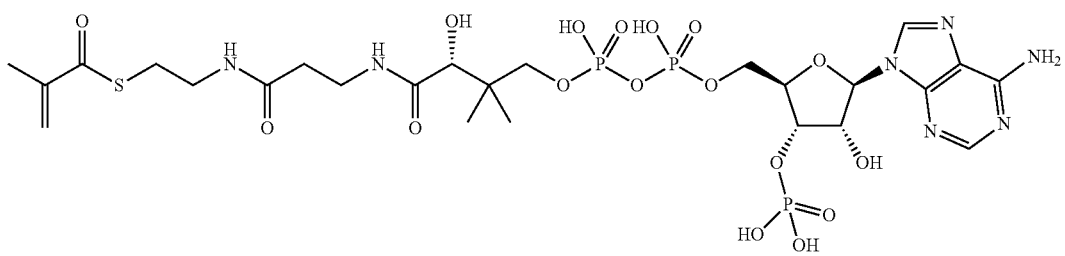

[Chem 1]

In the present invention, among these, methacrylyl-CoA (refer to FIG. 2) transformed by the action of acyl-CoA dehydrogenase (EC 1.3.99.3) (hereinafter referred to as ACD) with isobutyryl-CoA as a raw material or methacrylyl-CoA (refer to FIG. 1) transformed by action of enoyl-CoA hydratase (EC 4.2.1.17) (hereinafter referred to as ECH) from 3-hydroxyisobutyryl-CoA can be favorably used. In other words, the method of the present invention preferably further includes a step of producing methacrylyl-CoA from isobutyryl-CoA or 3-hydroxyisobutyryl-CoA. From the continuous reaction by enzyme, together with being connecting to a yield improvement as well as foreign matter suppression, the direct synthesis of methacrylic acid ester becomes possible without going through methacrylic acid having high toxicity to organisms, or forming byproducts. According to the method, it is possible to achieve production of methacrylic acid ester by an in vivo continuous reaction (metabolic fermentation) with low environmental burden.

Figure 2:
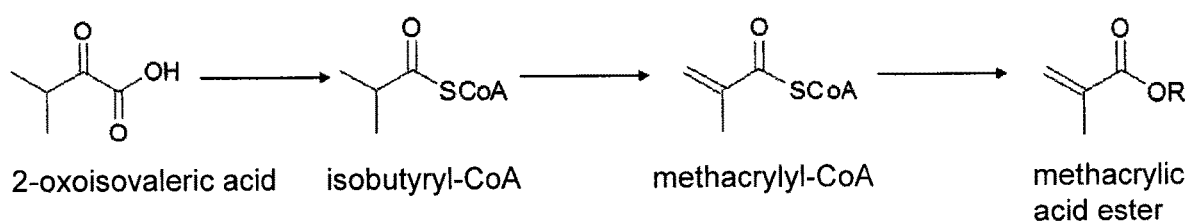
FIG. 2 is a view showing the production steps from 2-oxoisovaleric acid to methacrylic acid ester.

For the isobutyryl-CoA used in the present invention, one produced from 2-oxoisovaleric acid can be used (refer to FIG. 2). In other words, the method of the present invention may further include a step of producing isobutyryl-CoA from 2-oxoisovaleric acid.

Alcohols and Phenols

The alcohols or phenols serving as raw materials in the production of the methacrylic acid ester in the present invention are compounds expressed by formula 2 below. The structure of the alcohol or phenols corresponds to methacrylic acid ester; therefore, the structure thereof is defined the same as R in Formula 1, and represents a linear or branched C1-20 hydrocarbon group. The hydrocarbon group may be of saturated or unsaturated non-cyclic type, or may be of saturated or unsaturated cyclic type. It is preferably a linear or branched C1-10 unsubstituted alcohol, aralkyl alcohol or phenol, and particularly preferably a C1-8 alkyl alcohol such as methanol, ethanol, n-propanol, isopropanol, n-butanol, isobutanol, sec-butanol, tert-butanol, n-pentylalcohol, isopentyl alcohol, tert-pentyl alcohol, n-hexyl alcohol, isohexyl alcohol, 2-hexyl alcohol, dimethylbutyl alcohol, ethylbutyl alcohol, heptyl alcohol, octyl alcohol, 2-ethylhexyl alcohol; a benzyl alcohol or a phenol.

$$R-OH \quad \text{(Formula 2)}$$

Alcohol Acyltransferase

The alcohol acyltransferase of the present invention (hereinafter referred to as AAT) is an enzyme having a catalytic action for synthesizing ester by causing the acyl group of acyl-CoA to transfer to the alcohol or phenol. AAT is considered to participate in the formation of esters in various fruits. AAT is known to be present in plants such as Zingiberales (banana), Rosales (strawberry, apple, pear, peach), Cucurbitales (melon), Ericales (kiwi), Lamiales (olive), Solanales (tomato), and Sapindales (lemon, mango).

The AAT used in the present invention is not particularly limited so long as being a catalyst of biological origin having a capacity to produce methacrylic acid ester with methacrylyl-CoA and alcohol or phenol as raw materials, and the kind and origin thereof are not of concern. One of plant origin is preferable as the enzyme source, and thereamong, one categorized as an angiosperm is preferable.

The AAT suited to the present invention can be easily selected from the plants by the following method. An appropriate part of the tissue is acquired by cutting as necessary. A solution containing methacrylyl-CoA and an alcohol or phenol represented by Formula 2 are added to this cut part, shaken, and allowed to react for a certain time. It is possible to confirm the synthetic activity by confirming the presence of methacrylic acid ester in this reaction solution by GC (gas chromatography). More specifically, for example, the sarcocarp or pericarp is cut, a solution containing 1 to 10 mM methacrylyl-CoA, 0.35 KCl and 5 to 50 times molar quantity of n-butanol is added thereto, and shaken for 1 to 10 hours at 30° C. After reaction completion, an AAT applicable to the present invention can be selected by confirming the presence of methacrylic acid ester by way of GC.

The enzyme source of AAT suited to the present invention, for example, is one belonging to any order selected from the group consisting of Zingiberales, Rosales, Ericales, Cucurbitales, Brassicales, Laurales, Poales, Arecales, Asparagales, Saxifragales, Caryophyllales, Vitales, Malpighiales, Oxalidales, Fabales, Sapindales, Malvales, Myrtales, Ranunculales, Solanales, Lamiales, Gentianales and Asterales. Thereamong, it is preferably one belonging to any order selected from the group consisting of Zingiberales, Rosales, Ericales, Cucurbitales, Brassicales and Laurales.

Plants of Musaceae and Zingiberaceaeare are preferable as those belonging to the order Zingiberales; plants of Rosaceae and Moraceae are preferable as those belonging to the order Rosales; plants of Ericaceae, Actinidiaceae, Ebenaceae and Theaceae are preferable as those belonging to the order Ericales; plants of Cucurbitaceae are preferable as those belonging to the order Cucurbitales; plants of Caricaceae and Brassicaceae are preferable as those belonging to the order Brassicales; plants of Lauraceae are preferable as those belonging to the order Laurales; plants of Bromeliaceae and Poaceae are preferable as those belonging to the order Poales; plants of Arecaceae are preferable as those belonging to the order Arecales; plants of Orchidaceae and Iridaceae are preferable as those belonging to the order Asparagales; plants of Grossulariaceae are preferable as those belonging to the order Saxifragales; plants of Caryophyllaceae are preferable as those belonging to the order Caryophyllales; plants of Vitaceae are preferable as those belonging to the order Vitales; plants of Malpighiaceae, Passifloraceae, Euphorbiaceae and Salicaceae are preferable as those belonging to the order Malpighiales; plants of Oxalidaceae are preferable as those belonging to the order Oxalidales; plants of Fabaceae are preferable as those belonging to the order Fabales; plants of Rutaceae, Sapindaceae and Anacardiaceae are preferable as those belonging to the order Sapindales; plants of Malvaceaeare are preferable as those belonging to the order Malvales; plants of Lythraceae, Onagraceae and Myrtaceae are preferable as those belonging to the order Myrtales; plants of Ranunculaceae and Papaveraceae are preferable as those belonging to the order Ranunculales; plants of Solanaceae are preferable as those belonging to the order Solanales; plants of Oleaceae, Verbenaceae and Lamiaceae are preferable as those belonging to the order Lamiales; plants of Apocynaceae are preferable as those belonging to the order Gentianales; and plants of Asteraceae are preferable as those belonging to the order Asterales. A related species of the above-mentioned plants can also be employed. Thereamong, it is more preferably a plant belonging to Musacea, Rosaceae, Ericeae, Actinidiaceae, Cucurbitaceae, Caricaceae or Lauraceae.

More specifically, plants of *Musa* are preferable as those belonging to the family Musaceae; plants of *Zingiber* are preferable as those belonging to the family Zingiberaceae; plants of *Fragaria, Malus, Prunus, Pyrus, Eriobotrya, Chaenomeles, Rubus* and *Rosa* are preferable as those belonging to the family Rosaceae; plants of *Ficus* are preferable as those belonging to the family Moraceae; plants of *Vaccinium* are preferable as those belonging to the family Ericaceae; plants of *Actinidia* are preferable as those belonging to the family Actinidiaceae; plants of *Diospyros* are preferable as those belonging to the family Ebenaceae; plants of *Camellia* are preferable as those belonging to the family Theaceae; plants of *Cucumis* and *Citrullus* are preferable as those belonging to the family Cucurbitaceae; plants of *Carica* and *Vasconcellea* are preferable as those belonging to the family Caricaceae; plants of *Arabidopsis* are preferable as those belonging to the family Brassicaceae; plants of *Persea* are preferable as those belonging to the family Lauraceae; plants of *Ananas* are preferable as those belonging to the family Bromeliaceae; plants of *Oryza, Triticum, Hordeum, Zea, Sorghum* and *Brachypodium* are preferable as those belonging to the family Poaceae; plants of *Cocus* are preferable as those belonging to the family Arecaceae; plants of *Vanda* are preferable as those belonging to the family Orchidaceae; plants of *Iris* are preferable as those belonging to the family Iridaceae; plants of *Ribes* are preferable as those belonging to the family Grossulariaceae; plants of *Gypsophila* are preferable as those belonging to the family Caryophyllaceae; plants of *Vitis* are preferable as those belonging to the family Vitaceae; plants of *Malpighia* are preferable as those belonging to the family Malpighiaceae; plants of *Passiflora* are preferable as those belonging to the family Passifloraceae; plants of *Ricinus* are preferable as those belonging to the family Euphorbiaceae; plants of *Populusare* preferable as those belonging to the family Salicaceae; plants of *Averrhoaare* preferable as those belonging to the family Oxalidaceae; plants of *Medicago, Lupinus, Glycine* and *Clitoria* are preferable as those belonging to the family Fabaceae; plants of *Citrus* and *Aegle* are preferable as those belonging to the family Rutaceae; plants of *Litchi* are preferable as those belonging to the family Sapindaceae; plants of *Mangifera* are preferable as those belonging to the family Anacardiaceae; plants of *Durioand Theobroma* are preferable as those belonging to the family Malvaceae; plants of *Punica* are preferable as those belonging to the family Lythraceae; plants of *Clarkia* are preferable as those belonging to the family Onagraceae; plants of *Psidium* are preferable as those belonging to the family Myrtaceae; plants of *Actaea* are preferable as those belonging to the family Ranunculaceae; plants of *Papaver* are preferable as those belonging to the family Papaveraceae; plants of *Solanum, Capsicum, Nicotiana* and *Petunia* are preferable as those belonging to the family Solanaceae; plants of *Olea* are preferable as those belonging to the family Oleaceae; plants of *Glandularia* are preferable as those belonging to the family Verbenaceae; plants of *Salvia* are preferable as those belonging to the family Lamiaceae; plants of *Rauvolfia* and *Catharanthus* are preferable as those belonging to the family Apocynaceae; and plants of *Chamaemelum* are preferable as those belonging to the family Asteraceae. Thereamong, plants belonging to *Musa, Fragaria, Malus, PRunus, Pyrus, Vaccinium, Actinidia, Cucumis, Carica* or *Persea* are more preferable. Furthermore, thereamong, plants belonging to *Musa, Malus, Pyrus, Actinidia, Cucumis, Carica* or *Persea* are particularly preferable.

Furthermore, more specifically, plants of *Musaxparadisiaca, Musabasjoo, Musacoccinea* and *Musaacuminata* are particularly preferable as those belonging to the genus *Musa*; plants of *Zingiberofficinale* are particularly preferable as those belonging to the genus *Zingiber*; plants of *Fragariaxananassa, Fragariavirginiana, Fragariachiloensis* and *Fragariavesca* are particularly preferable as those belonging to the genus *Fragaria*; plants of *Maluspumila, Malusdomes-* tica, Malusbaccata, Malushalliana, Malusfloribunda and Malusprunifolia are particularly preferable as those belonging to the genus *Malus*; plants of *Prunusmume, Prunusavium, Prunuspersica, Prunusarmeniaca, Prunusdulcis, Prunussalicina* and *Prunusdomestica* are particularly preferable as those belonging to the genus *Prunus*; plants of *Pyruscommunis, Pyruspyrifolia, Pyruscalleryana* and *Pyruspyraster* are particularly preferable as those belonging to the genus *Pyrus*; plants of *Eriobotryajaponica* are particularly preferable as those belonging to the genus *Eriobotrya*; plants of *Chaenomelessinensis* are particularly preferable as those belonging to the genus *Chaenomeles*; plants of *Rubusidaeus* and *Rubusfruticosus* are particularly preferable as those belonging to the genus *Rubus*; plants of *Rosarugosa* are particularly preferable as those belonging to the genus *Rosa*; plants of *Ficuscarica* are particularly preferable as those belonging to the genus *Ficus*; plants of *Vacciniumcorymbosum, Vacciniumangustifolium, Vacciniummyrtillus, Vacciniumvitis-idaea* and *Vacciniumoxycoccos* are particularly preferable as those belonging to the genus *Vaccinium*; plants of *Actinidiachinensis, Actinidiadeliciosa, Actinidiaarguta, Actinidiarufa* and *Actinidiapolygama* are particularly preferable as those belonging to the genus *Actinidia*; plants of *Diospyroskaki* are particularly preferable as those belonging to the genus *Diospyros*; plants of *Cameliasinensis* are particularly preferable as those belonging to the genus *Camellia*; plants of *Cucumissativus, Cucumismelo, Cucumisanguria* and *Cucumismetulifer* are particularly preferable as those belonging to the genus *Cucumis*; plants of *Citrulluslanatus* are particularly preferable as those belonging to the genus *Citrullus*; plants of *Caricapapaya* are particularly preferable as those belonging to the genus Caricaceae; plants of *Vasconcelleacundinamarcensis* are particularly preferable as those belonging to the genus *Vasconcellea*; plants of *Arabidopsisthaliana* and *Arabidopsislyrata* are particularly preferable as those belonging to the genus *Arabidopsis*; plants of *Perseaamericana* are particularly preferable as those belonging to the genus *Persea*; plants of *Ananascomosus* are particularly preferable as those belonging to the genus *Ananas*; plants of *Oryzasativa* are particularly preferable as those belonging to the genus *Oryza*; plants of *Triticumaestivum* are particularly preferable as those belonging to the genus *Triticum*; plants of *Hordeumvulgare* are particularly preferable as those belonging to the genus *Hordeum*; plants of *Zeamays* are particularly preferable as those belonging to the genus *Zea*; plants of *Sorghumbicolor* are particularly preferable as those belonging to the genus *Sorghum*; plants of *Brachypodiumdistachyon* are particularly preferable as those belonging to the genus *Brachypodium*; plants of *Cocosnucifera* are particularly preferable as those belonging to the genus *Cocos*; plants of *Vandahybridcultivar* are particularly preferable as those belonging to the genus *Vanda*; plants of *Irisxhollandica* are particularly preferable as those belonging to the genus *Iris*; plants of *Ribesnigrum* are particularly preferable as those belonging to the genus *Ribes*; plants of *Gypsophilapaniculata* and *Gypsophilaelegans* are particularly preferable as those belonging to the genus *Gypsophila*; plants of *Vitisvinifera* and *Vitislabrusca* are particularly preferable as those belonging to the genus *Vitis*; plants of *Malpighiaglabra* are particularly preferable as those belonging to the genus *Malpighia*; plants of *Passifloraedulis* are particularly preferable as those belonging to the genus *Passiflora*; plants of *Ricinuscommunis* are particularly preferable as those belonging to the genus *Ricinus*; plants of *Populustrichocarpa* are particularly preferable as those belonging to the genus *Populus*; plants of *Averrhoacarambola* are particularly preferable as those belonging to the genus *Averrhoa*; plants of *Medicagotruncatula* are particularly preferable as those belonging to the genus *Medicago*; plants of *Lupinusalbus* are particularly preferable as those belonging to the genus *Lupinus*; plants of *Glycinemax* are particularly preferable as those belonging to the genus *Glycine*; plants of *Clitoriaternatea* are particularly preferable as those belonging to the genus *Clitoria*; plants of *Citruslimon, Citrussudachi, Citrussphaerocarpa, Citrusxparadisi, Citrusjunos, Citrusaurantifolia, Citrusunshiu* and *Citrussinensis* are particularly preferable as those belonging to the genus *Citrus*; plants of *Aeglemarmelos* are particularly preferable as those belonging to the genus *Aegle*; plants of *Litchichinensi* are particularly preferable as those belonging to the genus *Litchi*; plants of *Mangiferaindica* are particularly preferable as those belonging to the genus *Mangifera*; plants of *Duriozibethinus* are particularly preferable as those belonging to the genus *Durio*; plants of *Theobromacacao* are particularly preferable as those belonging to the genus *Theobroma*; plants of *Punicagranatum* are particularly preferable as those belonging to the genus *Punica*; plants of *Clarkiabreweri* and *Clarkiaconcinna* are particularly preferable as those belonging to the genus *Clarkia*; plants of *Psidiumguajava* are particularly preferable as those belonging to the genus *Psidium*; plants of *Actaearacemosa* are particularly preferable as those belonging to the genus *Actaea*; plants of *Papaversomniferum, Papaverorientale* and *Papaverbracteatum* are particularly preferable as those belonging to the genus *Papaver*; plants of *Solanumlycopersicum* are particularly preferable as those belonging to the genus *Solanum*; plants of *Capsicumannuum* and *Capsicumchinense* are particularly preferable as those belonging to the genus *Capsicum*; plants of *Nicotianatabacum* and *Nicotianaattenuata* are particularly preferable as those belonging to the genus *Nicotiana*; plants of *Petuniaxhybrida* are particularly preferable as those belonging to the genus *Petunia*; plants of *Oleaeuropaea* are particularly preferable as those belonging to the genus *Olea*; plants of *Glandulariaxhybrida* are particularly preferable as those belonging to the genus *Glandularia*; plants of *Salviasplendens* are particularly preferable as those belonging to the genus *Salvia*; plants of *Rauvolfiaserpentina* are particularly preferable as those belonging to the genus *Rauvolfia*; plants of *Catharanthusroseus* are particularly preferable as those belonging to the genus *Catharanthus*; and plants of *Chamaemelumnobile* are particularly preferable as those belonging to the genus *Chamaemelum*. Thereamong, banana, strawberry, apple, Japanese apricot, European pear, blueberry, kiwi, melon, papaya or avocado is more preferable. Furthermore, thereamong, banana, apple, European pear, kiwi, melon, papaya or avocado is particularly preferable.

It should be noted that, in the case of performing the synthetic reaction using a plant as is as the enzyme source, in particular, it is more preferable to use plants belonging to *Malus*, *Carica* and *Persea*, when defining a C1-2 alcohol as the substrate. This is due to having higher generation efficiency than plants belonging to another genus.

In the present invention, the classifications of plant are defined following Botanical Journal of the Linnean Society, 2009, 161, 105121.

In the present invention, upon supplying AAT for reaction, mode of use is not particularly limited so long as exhibiting the above-mentioned catalytic activity, and it is possible to use the biological tissue or processed product thereof as is. As such biological tissue, the entire planta, plant organs (e.g., fruit, leaves, petals, stem, seed, etc.), or plant tissue (e.g., fruit skin, sarcocarp, etc.) can be used. As the processed product thereof, the crude enzyme liquid from extracting AAT from these biological tissues, purified enzyme, or the like can be exemplified.

AAT Activity Expression Recombinant Microorganism

Furthermore, upon supplying AAT for reaction, the gene for the AAT is isolated, for example, introduced to a general host vector system, and the microorganism transformed by this vector system can be used. As the host, as for bacteria, *E. coli, Rhodococcus, Pseudomonas, Corynebacterium, Bacillus, Streptococcus, Streptomyces*, etc. can be exemplified; as for yeast, *Saccharomyces, Candida, Shizosaccharomyces* and *Pichia*; and as for filamentous fungus, *Aspergillus*, etc. can be exemplified. Among these, it is particularly easy to use bacteria, and is also preferable in efficiency.

Several AAT genes have been published (for example, refer to Patent Document 7). A DNA probe is prepared based on this publication, and for example, a primer used in PCR is prepared, and this gene can be isolated by performing PCR. In addition, it is also possible to completely synthesize the nucleotide sequence of AAT gene by a common method. It can be similarly confirmed by the method whether these AAT for which genetic information is known have synthetic activity for methacrylic acid ester. On the other hand, for AAT having unclear genetic information, AAT can be purified, and genetic information can be obtained by a genetic engineering method on the basis of proteins thereof.

As a preferred AAT gene in the present invention, it is not particularly limited so long as the translated product thereof has a capability of producing methacrylic acid ester, and is appropriately selected from among the AAT enzymes sources. Particularly preferably, AAT apple-derived AAT gene (SEQ ID NO: 2), strawberry-derived AAT gene (SEQ ID NO: 4) and strawberry-derived AAT gene (SEQ ID NO: 6) can be exemplified.

It should be noted that genes coding proteins having activity to produce methacrylic acid ester from methacrylyl-CoA and alcohol including an amino acid sequence in which one or a plurality of amino acids have been substituted, deleted or added to a wild-type amino acid sequence are also included in the AAT genes of the present invention.

Herein, the term "plurality" refers to 1 to 40, preferably 1 to 20, and more preferably no more than 10. In order to introduce mutation to the gene, it is possible to use a kit for mutation introduction using a site-directed mutagenesis method, for example, QuikChange™ Site-Directed Mutagenesis Kit (Stratagene), GeneTailor™ Site-Directed Mutagenesis System (Invitrogen), TaKaRa Site-Directed Mutagenesis System (Mutan-K, Mutan-Super Express Km, etc.: Takara Bio), etc., by a known method such as the Kunkel method or Gapped duplex method. Alternatively, the entire gene having a sequence including mutation may be artificially synthesized.

In the present invention, confirmation of the nucleotide sequence of DNA can be performed by sequence determination by a common method. For example, based on Sanger's method, it is possible to confirm the sequence using an appropriate DNA sequencer.

In addition, in the AAT gene of the present invention, genes coding proteins having activity to produce methacrylic acid ester from methacrylyl-CoA and alcohol expressing at least 90% identity with the protein consisting of the wild-type amino acid sequence, preferably 95%, more preferably 99.5%, and even more preferably 99.9%, are also included.

Furthermore, in the AAT gene of the present invention, genes hybridizing under stringent conditions to a polynucleotide having the complementary nucleotide sequence to the wild-type nucleotide sequence, and coding protein having activity to produce methacrylic acid ester from methacrylyl-CoA and alcohol are also included. As the stringent conditions, for example, it is possible to exemplify conditions of perform hybridization by maintaining a nylon membrane fixing the DNA at the same temperature while probing at 65° C. for 20 hours in a solution containing 6×SSC (1×SSC is prepared by dissolving 8.76 g of sodium chloride and 4.41 g of sodium citrate in 1 liter of water), 1% SDS, 100 µg/ml salmon sperm DNA, 0.1% bovine serum albumin, 0.1% polyvinylpyrrolidone and 0.1% ficoll. For one skilled in the art, it is possible to take account of other terms and conditions such as probe concentration, length of probe, and reaction time in addition to such conditions as salt concentration, temperature of buffer, etc. so as to set the conditions of hybridization. As drying conditions after hybridization, for example, "2×SSC, 0.1% SDS, 42° C." and "1×SSC, 0.1% SDS, 37° C.", and as more stringent conditions, for example, conditions such as "1×SSC, 0.1% SDS, 65° C." and "0.5×SSC, 0.1% SDS, 50° C." can be exemplified.

Regarding the detailed sequence of the hybridization method, it is possible to refer to Molecular Cloning, A Laboratory Manual 2nd ed. (Cold Spring Harbor Laboratory Press (1989)), Current Protocols in Molecular Biology (John Wiley & Sons (1987-1997)), or the like.

Furthermore, in the AAT gene of the present invention, when calculating using the wild-type nucleotide sequence, BLAST, etc. (e.g., default, i.e. initial setting, parameters), genes coding protein having activity to produce methacrylic acid ester from methacrylyl-CoA and alcohol consisting of a nucleotide sequence having identity of at least 80%, more preferably at least 90%, and more preferably at least 95% are also included. In addition, the codons of the above-mentioned AAT genes may be changed according to the codon frequency of use in the microorganism host used in genetic transformation.

Herein, "identity" of the sequence, when the case of a nucleotide sequence, is arrived at by aligning both nucleotide sequences so that the bases of the two nucleotide sequences to be compared match as much as possible, and then expressing a value arrived at by subtracting the number of matching bases from the total number of bases as a percentage. Upon the above-mentioned alignment, appropriate gaps are inserted into one or both of the two sequences compared as necessary. Such an alignment of sequences can be performed using a known program such as BLAST, FASTA, and CLUSTAL, for example. In the case of gaps being inserted, the above-mentioned total number of bases becomes the number of bases arrived at by counting one gap as one base. In the case of the total number of bases arrived at by counting in this way differing between the two sequences compared, the identity (%) is calculated by subtracting the matching number of bases from the total number of bases in the longer sequence. This similarly applies also for the identity of amino acid sequences.

In the methacrylic acid ester synthesis reaction, it is possible to use the broth obtained by culturing these recombinant microorganisms as is, or use the bacterial cell obtained by a harvesting operation such as centrifugation from this broth, a processed product thereof, or the like. As the bacterial cell processed product, a bacterial cell treated with acetone, toluene or the like, freeze-dried bacterial cells, disrupted bacterial cells, or noncellular extract from disrupted bacterial cells, crude enzyme extracted from these enzymes or purified enzyme, etc. can be exemplified.

Methacrylic acid ester can also be synthesized with isobutyryl-CoA or 3-hydroxyisobutyryl-CoA as a raw material by simultaneously introducing ACD gene or ECH gene with AAT gene (refer to FIG. 1 and FIG. 2). Furthermore, by combining and introducing 2-oxoisovaleric acid dehydrogenase gene (hereinafter referred to as BCKAD), it is also possible to synthesize methacrylic acid from 2-oxoisovaleric acid.

Although there is no particular limitation in the origins of ACD, ECH and BCKAD in the present invention, the microorganisms listed below can be exemplified.

It is a microorganism belonging to the genus *Magnetospirillum, Rhodospirillum, Azospirillum, Tistrella, Acidiphilium, Rhodobacter, Paracoccus, Ruegeria, Jannaschia, Roseobacter, Dinoroseobacter, Pseudovibrio, Phaeobacter, Octadecabacter, Hyphomonas, Maricaulis, Hirschia, Sphingomonas, Novosphingobium, Sphingopyxis, Sphingobium, Erythrobacter, Brevundimonas, Caulobacter, Phenylobacterium, Asticcacaulis, Agrobacterium, Rhizobium, Sinorhizobium, Xanthobacter, Azorhizobium, Brucella, Ochrobactrum, Mesorhizobium, Chelativorans, Aurantimonas, Bradyrhizobium, Agromonas, Rhodopseudomonas, Nitrobacter, Methylobacterium, Rhodomicrobium, Pelagibacterium, Parvibaculum, Methylocystis, Parvularcula, Burkholderia, Ralstonia, Cupriavidus, Polynucleobacter, Achromobacter, Bordetella, Taylorella, Pusillimonas, Comamonas, Alicycliphilus, Delftia, Ramlibacter, Rhodoferax, Variovorax, Polaromonas, Acidovorax, Vermineph-robacter, Herminiimonas, Herbaspirillum, Collimonas, Chromobacterium, Laribacter, Pseudogulbenkiania, Nitrosomonas, Nitrosospira, Aromatoleum, Azoarcus, Dechloromonas, Thauera, Azospira (Dechlorosoma), Rheinheimera, Nitrosococcus, Halorhodospira, Xanthomonas, Stenotrophomonas, Pseudoxanthomonas, Rhodanobacter, Francisella, Cycloclasticus, Oceanospirillum, Hahella, Halomonas, Alcanivorax, Kangiella, Pseudomonas, Azotobacter, Acinetobacter, Psychrobacter, Alishewanella, Alteromonas, Glaciecola, Marinobacter, Marinobacterium, Saccharophagus, Shewanella, Ferrimonas, Idiomarina, Colwellia, Pseudoalteromonas, Listonella, Vibrio, Photobacterium, Aeromonas, Oceanimonas, Salinisphaera, Legionella, Coxiella, Desulfococcus, Desulfobacterium, Desulfatibacillum, Desulfobulbus, Desulfarculus, Geobacter, Syntrophobacter, Syntrophus, Desulfomonile, Bdellovibrio, Bacteriovorax, Stigmatella, Myxococcus, Anaeromyxobacter, Sorangium, Haliangium, Acidobacterium, Granulicella, Ilumatobacter, Streptosporangium, Nocardiopsis, Thermobifida, Thermomonospora, Pseudonocardia, Amycolatopsis, Saccharomonospora, Saccharopolyspora, Thermobispora, Actinosynnema, Micromonospora, Salinispora, Verrucosispora, Nocardioides, Kribbella, Corynebacterium, Nocardia, Rhodococcus, Gordonia, Dietzia, Mycobacterium, Amycolicicoccus, Tsukamurella, Segniliparus, Microbacterium, Micrococcus, Arthrobacter, Citricoccus, Renibacterium, Kocuria, Kytococcus, Cellulomonas, Intrasporangium, Serinicoccus, Frankia, Acidothermus, Nakamurella, Geodermatophilus, Stackebrandtia, Streptomyces, Catenulispora, Rubrobacter, Conexibacter, Bacillus, Geobacillus, Oceanobacillus, Lysinibacillus, Halobacillus, Alicyclobacillus, Kyrpidia, Paenibacillus, Lactobacillus, Carnobacterium, Clostridium, Alkaliphilus, Syntrophomonas, Syntrophothermus, Eubacterium, Desulfitobacterium, Desulfotomaculum, Pelotomaculum, Butyrivibrio, Roseburia, Oscillibacter, Thermoanaerobacter, Carboxydothermus, Natranaerobius, Sphingobacterium, Pedobacter, Haliscomenobacter, Porphyromonas, Odoribacter, Spirosoma, Runella, Maribacter, Deinococcus, Thermus, Meiothermus, Oceanithermus, Marinithermus, Gemmatimonas, Fusobacterium, Ilyobacter, Roseiflexus, Herpetosiphon, Thermomicrobium, Thermotoga, Thermosipho, Fervidobacterium, Deferribacter, Calditerrivibrio, Flexistipes, Metallosphaera, Aeropyrum, Pyrobaculum, Caldivirga, Vulcanisaeta, Acidilobus, Haloarcula, Haloquadratum, Natronomonas, Halorubrum, Haloterrigena, Natrialba, Halalkalicoccus, Halogeometricum, Thermoplasma, Picrophilus, Ferroplasma, Archaeoglobus, Ferroglobus, Polymorphum, Micavibrio, Simiduia, Leptothrix, Thiomonas, Rubrivivax, Methylibium, Exiguobacterium* and *Anaerococcus.*

Furthermore, *Magnetospirillum magneticum* is particularly preferable as the microorganism classified as *Magnetospirillum; Rhodospirillum rubrum, Rhodospirillum centenum* and *Rhodospirillum photometricum* are particularly preferable as the microorganism classified as *Rhodospirillum; Azospirillum lipoferum* and *Azospirillum brasilense* are particularly preferable as the microorganism classified as *Azospirillum; Tistrella mobilis* is particularly preferable as the microorganism classified as *Tistrella; Acidiphilium cryptum* and *Acidiphilium multivorum* are particularly preferable as the microorganism classified as *Acidiphilium; Rhodobacter sphaeroides* and *Rhodobacter capsulatus* are particularly preferable as the microorganism classified as *Rhodobacter; Paracoccus denitrificans* and *Paracoccus aminophilus* are particularly preferable as the microorganism classified as *Paracoccus; Ruegeria pomeroyi* is particularly preferable as the microorganism classified as *Ruegeria; Roseobacter denitrificans* and *Roseobacter litoralis* are particularly preferable as the microorganism classified as *Roseobacter; Dinoroseobacter shibae* is particularly preferable as the microorganism classified as *Dinoroseobacter; Phaeobacter gallaeciensis* is particularly preferable as the microorganism classified as *Phaeobacter; Octadecabacter antarcticus* and *Octadecabacter arcticus* are particularly preferable as the microorganism classified as *Octadecabacter; Hyphomonas neptunium* is particularly preferable as the microorganism classified as *Hyphomonas; Maricaulis maris* is particularly preferable as the microorganism classified as *Maricaulis; Hirschia baltica* is particularly preferable as the microorganism classified as *Hirschia; Sphingomonas paucimobilis* and *Sphingomonas wittichii* are particularly preferable as the microorganism classified as *Sphingomonas; Novosphingobium aromaticivorans* is particularly preferable as the microorganism classified as *Novosphingobium; Sphingopyxis alaskensis* is particularly preferable as the microorganism classified as *Sphingopyxis; Sphingobium japonicum* and *Sphingobium chlorophenolicum* are particularly preferable as the microorganism classified as *Sphingobium; Erythrobacter litoralis* is particularly preferable as the microorganism classified as *Erythrobacter; Brevundimonas diminuta, Brevundimonas subvibrioides* and *Brevundimonas vesicularis* are particularly preferable as the microorganism classified as *Brevundimonas; Caulobacter crescentus* and *Caulobacter segnis* are particularly preferable as the microorganism classified as *Caulobacter; Phenylobacterium zucineum* is particularly preferable as the microorganism classified as *Phenylobacterium; Asticcacaulis excentricus* is particularly preferable as the microorganism classified as *Asticcacaulis; Agrobacterium tumefaciens, Agrobacterium radiobacter* and *Agrobacterium luteum* are particularly preferable as the microorganism classified as *Agrobacterium; Rhizobium leguminosarum, Rhizobium etli* and *Rhizobium tropici* are particularly preferable as the microorganism classified as *Rhizobium; Sinorhizobium meliloti, Sinorhizobium medicae* and *Sinorhizobium fredii* are particularly preferable as the microorganism classified as *Sinorhizobium; Xanthobacter agilis, Xanthobacter aminoxidans, Xanthobacter autotrophicus, Xanthobacter flavus,*

*Xanthobacter tagetidis* and *Xanthobacter viscosus* are particularly preferable as the microorganism classified as *Xanthobacter*; *Azorhizobium caulinodans* is particularly preferable as the microorganism classified as *Azorhizobium*; *Brucella melitensis*, *Brucella abortus*, *Brucella suis*, *Brucella ovis*, *Brucella canis*, *Brucella microti*, *Brucella pinnipedialis* and *Brucella ceti* are particularly preferable as the microorganism classified as *Brucella*; *Ochrobactrum anthropi*, *Ochrobactrum cytisi*, *Ochrobactrum daejeonense*, *Ochrobactrum gallinifaecis*, *Ochrobactrum grignonense*, *Ochrobactrum haemophilum*, *Ochrobactrum intermedium*, *Ochrobactrum lupini*, *Ochrobactrum oryzae*, *Ochrobactrum pseudintermedium*, *Ochrobactrum pseudogrignonense*, *Ochrobactrum thiophenivorans* and *Ochrobactrum tritici* are particularly preferable as the microorganism classified as *Ochrobactrum*; *Mesorhizobium alhagi*, *Mesorhizobium albiziae*, *Mesorhizobium amorphae*, *Mesorhizobium australicum*, *Mesorhizobium caraganae*, *Mesorhizobium chacoense*, *Mesorhizobium ciceri*, *Mesorhizobium gobiense*, *Mesorhizobium loti*, *Mesorhizobium mediterraneum*, *Mesorhizobium metallidurans*, *Mesorhizobium opportunistum*, *Mesorhizobium plurifarium*, *Mesorhizobium huakuii*, *Mesorhizobium septentrionale*, *Mesorhizobium shangrilense*, *Mesorhizobium tarimense*, *Mesorhizobium temperatum*, *Mesorhizobium thiogangeticum* and *Mesorhizobium tianshanense* are particularly preferable as the microorganism classified as *Mesorhizobium*; *Aurantimonas manganoxydans* is particularly preferable as the microorganism classified as *Aurantimonas*; *Bradyrhizobium japonicum* is particularly preferable as the microorganism classified as *Bradyrhizobium*; *Agromonas oligotrophica* is particularly preferable as the microorganism classified as *Agromonas*; *Rhodopseudomonas palustris* is particularly preferable as the microorganism classified as *Rhodopseudomonas*; *Nitrobacter winogradskyi* and *Nitrobacter hamburgensis* are particularly preferable as the microorganism classified as *Nitrobacter*; *Methylobacterium extorquens*, *Methylobacterium radiotolerans* and *Methylobacterium nodulans* are particularly preferable as the microorganism classified as *Methylobacterium*; *Rhodomicrobium vannielii* is particularly preferable as the microorganism classified as *Rhodomicrobium*; *Pelagibacterium halotolerans* is particularly preferable as the microorganism classified as *Pelagibacterium*; *Parvibaculum lavamentivorans* is particularly preferable as the microorganism classified as *Parvibaculum*; *Parvularcula bermudensis* is particularly preferable as the microorganism classified as *Parvularcula*; *Burkholderia mallei*, *Burkholderia pseudomallei*, *Burkholderia thailandensis*, *Burkholderia vietnamiensis*, *Burkholderia cenocepacia*, *Burkholderia ambifaria*, *Burkholderia multivorans*, *Burkholderia cepacia*, *Burkholderia xenovorans*, *Burkholderia phymatum*, *Burkholderia phytofirmans*, *Burkholderia glumae*, *Burkholderia rhizoxinica*, *Burkholderia gladioli*, *Burkholderia phenoliruptrix* and *Burkholderia oklahomensis* are particularly preferable as the microorganism classified as *Burkholderia*; *Ralstonia solanacearum*, *Ralstonia pickettii* and *Ralstonia eutropha* are particularly preferable as the microorganism classified as *Ralstonia*; *Cupriavidus metallidurans*, *Cupriavidus taiwanensis* and *Cupriavidus necator* are particularly preferable as the microorganism classified as *Cupriavidus*; *Polynucleobacter necessarius* is particularly preferable as the microorganism classified as *Polynucleobacter*; *Achromobacter arsenitoxydans*, *Achromobacter cholinophagum*, *Achromobacter cycloclastes*, *Achromobacter denitrificans*, *Achromobacter fischeri*, *Achromobacter hartlebii*, *Achromobacter immobilis*, *Achromobacter insolitus*, *Achromobacter lactolyticus*, *Achromobacter lyticus*, *Achromobacter methanolophila*, *Achromobacter pestifer*, *Achromobacter piechaudii*, *Achromobacter ruhlandii*, *Achromobacter spanios*, *Achromobacter viscosus*, *Achromobacter xerosis* and *Achromobacter xylosoxidans* are particularly preferable as the microorganism classified as *Achromobacter*; *Bordetella pertussis*, *Bordetella parapertussis*, *Bordetella petrii* and *Bordetella avium* are particularly preferable as the microorganism classified as *Bordetella*; *Taylorella equigenitalis* is particularly preferable as the microorganism classified as *Taylorella*; *Comamonas acidovorans*, *Comamonas aquatica*, *Comamonas badia*, *Comamonas composti*, *Comamonas denitrificans*, *Comamonas granuli*, *Comamonas kerstersii*, *Comamonas koreensis*, *Comamonas nitrativorans*, *Comamonas odontotermites*, *Comamonas terrae*, *Comamonas terrigena*, *Comamonas testosteroni*, *Comamonas thiooxydans* and *Comamonas zonglianii* are particularly preferable as the microorganism classified as *Comamonas*; *Alicycliphilus denitrificans* is particularly preferable as the microorganism classified as *Alicycliphilus*; *Delftia acidovorans* is particularly preferable as the microorganism classified as *Delftia*; *Ramlibacter tataouinensis* is particularly preferable as the microorganism classified as *Ramlibacter*; *Rhodoferax ferrireducens* is particularly preferable as the microorganism classified as *Rhodoferax*; *Variovorax paradoxus* is particularly preferable as the microorganism classified as *Variovorax*; *Polaromonas naphthalenivorans* is particularly preferable as the microorganism classified as *Polaromonas*; *Acidovorax citrulli*, *Acidovorax ebreus* and *Acidovorax avenae* are particularly preferable as the microorganism classified as *Acidovorax*; *Verminephrobacter eiseniae* is particularly preferable as the microorganism classified as *Verminephrobacter*; *Herminiimonas arsenicoxydans* is particularly preferable as the microorganism classified as *Herminiimonas*; *Herbaspirillum seropedicae* is particularly preferable as the microorganism classified as *Herbaspirillum*; *Collimonas fungivorans* is particularly preferable as the microorganism classified as *Collimonas*; *Chromobacterium violaceum* is particularly preferable as the microorganism classified as *Chromobacterium*; *Laribacter hongkongensis* is particularly preferable as the microorganism classified as *Laribacter*; *Pseudogulbenkiania ferrooxidans* is particularly preferable as the microorganism classified as *Pseudogulbenkiania*; *Nitrosomonas europaea* is particularly preferable as the microorganism classified as *Nitrosomonas*; *Nitrosospira multiformis* is particularly preferable as the microorganism classified as *Nitrosospira*; *Aromatoleum aromaticum* is particularly preferable as the microorganism classified as *Aromatoleum*; *Dechloromonas aromatica* is particularly preferable as the microorganism classified as *Dechloromonas*; *Azospira oryzae* (*Dechlorosoma suillum*) is particularly preferable as the microorganism classified as *Azospira* (*Dechlorosoma*); *Rheinheimera nanhaiensis* is particularly preferable as the microorganism classified as *Rheinheimera*; *Nitrosococcus oceani* is particularly preferable as the microorganism classified as *Nitrosococcus*; *Halorhodospira halophila* is particularly preferable as the microorganism classified as *Halorhodospira*; *Xanthomonas campestris*, *Xanthomonas axonopodis*, *Xanthomonas oryzae*, *Xanthomonas albilineans* and *Xanthomonas citri* are particularly preferable as the microorganism classified as *Xanthomonas*; *Stenotrophomonas maltophilia* is particularly preferable as the microorganism classified as *Stenotrophomonas*; *Pseudoxanthomonas suwonensis* and *Pseudoxanthomonas spadix* are particularly preferable as the microorganism classified as *Pseudoxanthomonas*; *Francisella tularensis* and *Francisella novicida* are particularly preferable as the microorganism classified as *Francisella*; *Cycloclasticus zancles* is particularly preferable as the microorganism classified as *Cycloclasticus*; *Hahella chejuensis* is particularly preferable as the microorganism classified as *Hahella*; *Halomonas elongata* is particularly preferable as the microorganism classified as *Halomonas*; *Alcanivorax borkumensis* and *Alcanivorax dieselolei* are particularly preferable as the microorganism classified as *Alcanivorax*; *Kangiella koreensis* is particularly preferable as the microorganism classified as *Kangiella*; *Pseudomonas aeruginosa*, *Pseudomonas putida*, *Pseudomonas fluorescens*, *Pseudomonas agarici*, *Pseudomonas syringae*, *Pseudomonas amygdale* and *Pseudomonas stutzeri*, for example, are particularly preferable as the microorganism classified as *Pseudomonas*; *Azotobacter vinelandii* is particularly preferable as the microorganism classified as *Azotobacter*; *Acinetobacter baumannii*, *Acinetobacter aylyi*, *Acinetobacter calcoaceticus*, *Acinetobacter gyllenbergii*, *Acinetobacter haemolyticus*, *Acinetobacter johnsonii*, *Acinetobacter junii*, *Acinetobacter lwoffii*, *Acinetobacter oleivorans* and *Acinetobacter parvus* are particularly preferable as the microorganism classified as *Acinetobacter*; *Psychrobacter arcticus* and *Psychrobacter cryohalolentis* are particularly preferable as the microorganism classified as *Psychrobacter*; *Alishewanella jeotgali* is particularly preferable as the microorganism classified as *Alishewanella*; *Alteromonas macleodii* is particularly preferable as the microorganism classified as *Alteromonas*; *Glaciecola nitratireducens*, *Glaciecola psychrophila* and *Glaciecola punicea* are particularly preferable as the microorganism classified as *Glaciecola*; *Marinobacter aquaeolei*, *Marinobacter hydrocarbonoclasticus*, *Marinobacter adhaerens*, *Marinobacter algicola* and *Marinobacter manganoxydans* are particularly preferable as the microorganism classified as *Marinobacter*; *Marinobacterium stanieri* is particularly preferable as the microorganism classified as *Marinobacterium*; *Saccharophagus degradans* is particularly preferable as the microorganism classified as *Saccharophagus*; *Shewanella piezotolerans*, *Shewanella abyssi*, *Shewanella affinis*, *Shewanella algae*, *Shewanella algidipiscicola*, *Shewanella amazonensis*, *Shewanella aquimarina*, *Shewanella arctica*, *Shewanella atlantica*, *Shewanella baltica*, *Shewanella basaltis*, *Shewanella benthica*, *Shewanella candadensis*, *Shewanella chilikensis*, *Shewanella colwelliana*, *Shewanella corallii*, *Shewanella decolorationis*, *Shewanella denitrificans*, *Shewanella donghaensis*, *Shewanella fidelis*, *Shewanella fodinae*, *Shewanella frigidimarina*, *Shewanella gaetbuli*, *Shewanella gelidimarina*, *Shewanella glacialipiscicola*, *Shewanella gopherii*, *Shewanella hafniensis*, *Shewanella halifaxensis*, *Shewanella haliotis*, *Shewanella hanedai*, *Shewanella japonica*, *Shewanella kaireitica*, *Shewanella ivingstonensis*, *Shewanella loihica*, *Shewanella marina*, *Shewanella marinintestina*, *Shewanella marisflavi*, *Shewanella morhuae*, *Shewanella olleyana*, *Shewanella oneidensis*, *Shewanella pacifica*, *Shewanella pealeana*, *Shewanella pneumatophori*, *Shewanella profunda*, *Shewanella putrefaciens*, *Shewanella sairae*, *Shewanella schlegeliana*, *Shewanella sediminis*, *Shewanella surugensis*, *Shewanella vesiculosa*, *Shewanella violacea*, *Shewanella waksmanii*, *Shewanella woodyi* and *Shewanella xiamenensis* are particularly preferable as the microorganism classified as *Shewanella*; *Ferrimonas balearica* is particularly preferable as the microorganism classified as *Ferrimonas*; *Idiomarina loihiensis* and *Idiomarina baltica* are particularly preferable as the microorganism classified as *Idiomarina*; *Colwellia psychrerythraea* is particularly preferable as the microorganism classified as *Colwellia*; *Pseudoalteromonas haloplanktis*, *Pseudoalteromonas atlantica* and *Pseudoalteromonas tunicata* are particularly preferable as the microorganism classified as *Pseudoalteromonas*; *Listonella anguillara*, *Listonella anguillarum* and *Listonella pelagia* are particularly preferable as the microorganism classified as *Listonella*; *Vibrio parahaemolyticus*, *Vibrio vulnificus*, *Vibrio harveyi*, *Vibrio furnissii*, *Vibrio tubiashii*, *Vibrio sinaloensis*, *Vibrio rotiferianus*, *Vibrio orientalis*, *Vibrio harveyi*, *Vibrio coralliilyticus*, *Vibrio caribbenthicus*, *Vibrio brasiliensis* and *Vibrio alginolyticus* are particularly preferable as the microorganism classified as *Vibrio*; *Photobacterium profundum* is particularly preferable as the microorganism classified as *Photobacterium*; *Aeromonas hydrophila*, *Aeromonas salmonicida* and *Aeromonas veronii* are particularly preferable as the microorganism classified as *Aeromonas*; *Salinisphaera shabanensis* is particularly preferable as the microorganism classified as *Salinisphaera*; *Legionella pneumophila* and *Legionella longbeachae* are particularly preferable as the microorganism classified as *Legionella*; *Coxiella burnetii* is particularly preferable as the microorganism classified as *Coxiella*; *Desulfococcus oleovorans* is particularly preferable as the microorganism classified as *Desulfococcus*; *Desulfobacterium autotrophicum* is particularly preferable as the microorganism classified as *Desulfobacterium*; *Desulfatibacillum alkenivorans* is particularly preferable as the microorganism classified as *Desulfatibacillum*; *Desulfobulbus propionicus* is particularly preferable as the microorganism classified as *Desulfobulbus*; *Desulfarculus baarsii* is particularly preferable as the microorganism classified as *Desulfarculus*; *Geobacter metallireducens*, *Geobacter uraniireducens* and *Geobacter bemidjiensis* are particularly preferable as the microorganism classified as *Geobacter*; *Syntrophobacter fumaroxidans* is particularly preferable as the microorganism classified as *Syntrophobacter*; *Syntrophus aciditrophicus* is particularly preferable as the microorganism classified as *Syntrophus*; *Desulfomonile tiedjei* is particularly preferable as the microorganism classified as *Desulfomonile*; *Bdellovibrio bacteriovorus* and *Bdellovibrio exovorus* are particularly preferable as the microorganism classified as *Bdellovibrio*; *Bacteriovorax marinus* is particularly preferable as the microorganism classified as *Bacteriovorax*; *Stigmatella aurantiaca* is particularly preferable as the microorganism classified as *Stigmatella*; *Myxococcus xanthus* and *Myxococcus fulvus* are particularly preferable as the microorganism classified as *Myxococcus*; *Anaeromyxobacter dehalogenans* is particularly preferable as the microorganism classified as *Anaeromyxobacter*; *Sorangium cellulosum* is particularly preferable as the microorganism classified as *Sorangium*; *Haliangium ochraceum* is particularly preferable as the microorganism classified as *Haliangium*; *Acidobacterium capsulatum* is particularly preferable as the microorganism classified as *Acidobacterium*; *Granulicella tundricola* is particularly preferable as the microorganism classified as *Granulicella*; *Ilumatobacter coccineum* is particularly preferable as the microorganism classified as *Ilumatobacter*; *Streptosporangium roseum* is particularly preferable as the microorganism classified as *Streptosporangium*; *Nocardiopsis dassonvillei* is particularly preferable as the microorganism classified as *Nocardiopsis*; *Thermobifida fusca* is particularly preferable as the microorganism classified as *Thermobifida*; *Thermomonospora curvata* is particularly preferable as the microorganism classified as *Thermomonospora*; *Pseudonocardia dioxanivorans* is particularly preferable as the microorganism classified as *Pseudonocardia*; *Amycolatopsis mediterranei* is particularly preferable as the microorganism classified as *Amycolatopsis*; *Saccharomonospora viridis* and *Saccharomonospora xinjiangensis* are particularly preferable as the microorganism classified as *Saccharomonospora*; *Saccharopolyspora erythraea* and *Saccharopolyspora spinosa* are particularly preferable as the microorganism classified as *Saccharopolyspora*; *Thermobispora bispora* is particularly preferable as the microorganism classified as *Thermobispora*; *Actinosynnema mirum* is particularly preferable as the microorganism classified as *Actinosynnema*; *Micromonospora aurantiaca* is particularly preferable as the microorganism classified as *Micromonospora*; *Salinispora tropica* and *Salinispora arenicola* are particularly preferable as the microorganism classified as *Salinispora*; *Verrucosispora maris* is particularly preferable as the microorganism classified as *Verrucosispora*; *Kribbella flavida* is particularly preferable as the microorganism classified as *Kribbella*; *Corynebacterium jeikeium*, *Corynebacterium urealyticum* and *Corynebacterium kroppenstedtii* are particularly preferable as the microorganism classified as *Corynebacterium*; *Nocardia farcinica*, *Nocardia brasiliensis* and *Nocardia cyriacigeorgica* are particularly preferable as the microorganism classified as *Nocardia*; *Rhodococcus rhodochrous*, *Rhodococcus erythropolis*, *Rhodococcus equi*, *Rhodococcus rhodnii*, *Rhodococcus corallinus*, *Rhodococcus rubropertinctus*, *Rhodococcus coprophilus*, *Rhodococcus globerulus*, *Rhodococcus chlorophenolicus*, *Rhodococcus luteus*, *Rhodococcus aichiensis*, *Rhodococcus chubuensis*, *Rhodococcus maris* and *Rhodococcus fascines* are particularly preferable as the microorganism classified as *Rhodococcus*; *Gordonia bronchialis*, *Gordonia neofelifaecis* and *Gordonia terrae* are particularly preferable as the microorganism classified as *Gordonia*; *Dietzia cinnamea* is particularly preferable as the microorganism classified as *Dietzia*; *Mycobacterium tuberculosis*, *Mycobacterium bovis*, *Mycobacterium leprae*, *Mycobacterium avium*, *Mycobacterium smegmatis*, *Mycobacterium ulcerans*, *Mycobacterium vanbaalenii*, *Mycobacterium gilvum*, *Mycobacterium abscessus*, *Mycobacterium marinu*, *Mycobacterium massiliense*, *Mycobacterium phlei*, *Mycobacterium thermoresistibile*, *Mycobacterium tusciae*, *Mycobacterium xenopi* and *Mycobacterium rhodesiae* are particularly preferable as the microorganism classified as *Mycobacterium*; *Amycolicicoccus subflavus* is particularly preferable as the microorganism classified as *Amycolicicoccus*; *Tsukamurella paurometabola* is particularly preferable as the microorganism classified as *Tsukamurella*; *Segniliparus rotundus* is particularly preferable as the microorganism classified as *Segniliparus*; *Microbacterium testaceum* is particularly preferable as the microorganism classified as *Microbacterium*; *Micrococcus luteus* is particularly preferable as the microorganism classified as *Micrococcus*; *Arthrobacter arilaitensis*, *Arthrobacter chlorophenolicus*, *Arthrobacter globiformis* and *Arthrobacter phenanthrenivorans* are particularly preferable as the microorganism classified as *Arthrobacter*; *Renibacterium salmoninarum* is particularly preferable as the microorganism classified as *Renibacterium*; *Kocuria rhizophila* is particularly preferable as the microorganism classified as *Kocuria*; *Kytococcus sedentarius* is particularly preferable as the microorganism classified as *Kytococcus*; *Cellulomonas fimi* is particularly preferable as the microorganism classified as *Cellulomonas*; *Intrasporangium calvum* is particularly preferable as the microorganism classified as *Intrasporangium*; *Serinicoccus profundi* is particularly preferable as the microorganism classified as *Serinicoccus*; *Frankia alni* is particularly preferable as the microorganism classified as *Frankia*; *Acidothermus cellulolyticus* is particularly preferable as the microorganism classified as *Acidothermus*; *Nakamurella multipartita* is particularly preferable as the microorganism classified as *Nakamurella*; *Geodermatophilus obscurus* is particularly preferable as the microorganism classified as *Geodermatophilus*; *Stackebrandtia nassauensis* is particularly preferable as the microorganism classified as *Stackebrandtia*; *Streptomyces albus*, *Streptomyces avermitilis*, *Streptomyces bingchenggensis*, *Streptomyces chartreusis*, *Streptomyces clavuligerus*, *Streptomyces coelicoflavus*, *Streptomyces coelicolor*, *Streptomyces ghanaensis*, *Streptomyces griseus*, *Streptomyces hygroscopicus*, *Streptomyces lividans*, *Streptomyces roseosporus*, *Streptomyces scabiei*, *Streptomyces sviceus*, *Streptomyces venezuelae*, *Streptomyces violaceusniger* and *Streptomyces viridochromogenes* are particularly preferable as the microorganism classified as *Streptomyces*; *Catenulispora acidiphila* is particularly preferable as the microorganism classified as *Catenulispora*; *Rubrobacter xylanophilus* is particularly preferable as the microorganism classified as *Rubrobacter*; *Conexibacter woesei* is particularly preferable as the microorganism classified as *Conexibacter*; *Bacillus thuringiensis*, *Bacillus megaterium*, *Bacillus pseudofirmus*, *Bacillus clausii*, *Bacillus cereus*, *Bacillus subtilis* and *Bacillus thuringiensis* are particularly preferable as the microorganism classified as *Bacillus*; *Geobacillus caldoproteolyticus*, *Geobacillus caldoxylosilyticus*, *Geobacillus debilis*, *Geobacillus galactosidasius*, *Geobacillus gargensis*, *Geobacillus jurassicus*, *Geobacillus kaustophilus*, *Geobacillus lituanicus*, *Geobacillus pallidus*, *Geobacillus stearothermophilus*, *Geobacillus stromboliensis*, *Geobacillus subterraneus*, *Geobacillus tepidamans*, *Geobacillus thermocatenulatus*, *Geobacillus thermodenitrificans*, *Geobacillus thermoglucosidasius*, *Geobacillus thermoleovorans*, *Geobacillus toebii*, *Geobacillus uzensis*, *Geobacillus vulcani* and *Geobacillus zalihae* are particularly preferable as the microorganism classified as *Geobacillus*; *Oceanobacillus iheyensis* is particularly preferable as the microorganism classified as *Oceanobacillus*; *Lysinibacillus sphaericus* is particularly preferable as the microorganism classified as *Lysinibacillus*; *Halobacillus halophilus* is particularly preferable as the microorganism classified as *Halobacillus*; *Alicyclobacillus acidocaldarius* is particularly preferable as the microorganism classified as *Alicyclobacillus*; *Kyrpidia tusci* is particularly preferable as the microorganism classified as *Kyrpidia*; *Paenibacillus polymyxa*, *Paenibacillus mucilaginosus* and *Paenibacillus terrae* are particularly preferable as the microorganism classified as *Paenibacillus*; *Lactobacillus buchneri* is particularly preferable as the microorganism classified as *Lactobacillus*; *Clostridium acetobutylicum*, *Clostridium perfringens*, *Clostridium kluyveri*, *Clostridium cellulovorans*, *Clostridium difficile* and *Clostridium sticklandii* are particularly preferable as the microorganism classified as *Clostridium*; *Alkaliphilus metalliredigens* and *Alkaliphilus oremlandii* are particularly preferable as the microorganism classified as *Alkaliphilus*; *Syntrophomonas wolfei* is particularly preferable as the microorganism classified as *Syntrophomonas*; *Syntrophothermus lipocalidus* is particularly preferable as the microorganism classified as *Syntrophothermus*; *Eubacterium rectale* and *Eubacterium limosum* are particularly preferable as the microorganism classified as *Eubacterium*; *Desulfitobacterium hafniense* is particularly preferable as the microorganism classified as *Desulfitobacterium*; *Desulfotomaculum reducens* is particularly preferable as the microorganism classified as *Desulfotomaculum*; *Pelotomaculum thermopropionicum* is particularly preferable as the microorganism classified as *Pelotomaculum*; *Butyrivibrio proteoclasticus* is particularly preferable as the microorganism classified as *Butyrivibrio*; *Roseburia homi-*

*nis* is particularly preferable as the microorganism classified as *Roseburia*; *Oscillibacter valericigenes* is particularly preferable as the microorganism classified as *Oscillibacter*; *Thermoanaerobacter tengcongensis* is particularly preferable as the microorganism classified as *Thermoanaerobacter*; *Carboxydothermus hydrogenoformans* is particularly preferable as the microorganism classified as *Carboxydothermus*; *Natranaerobius thermophilus* is particularly preferable as the microorganism classified as *Natranaerobius*; *Sphingobacterium multivorum, Sphingobacterium spiritivorum, Sphingobacterium alimentarium, Sphingobacterium anhuiense, Sphingobacterium antarcticum, Sphingobacterium bambusae, Sphingobacterium canadense, Sphingobacterium composti, Sphingobacterium daejeonense, Sphingobacterium faecium, Sphingobacterium heparinum, Sphingobacterium kitahiroshimense, Sphingobacterium lactis, Sphingobacterium mizutaii, Sphingobacterium nematocida, Sphingobacterium piscium, Sphingobacterium shayense, Sphingobacterium siyangense, Sphingobacterium thalpophilum* and *Sphingobacterium wenxiniae* are particularly preferable as the microorganism classified as *Sphingobacterium*; *Pedobacter steynii, Pedobacter duraquae, Pedobacter metabolipauper, Pedobacter hartonius, Pedobacter heparinus Pedobacter africanus, Pedobacter agri, Pedobacter alluvius* and *Pedobacter saltans* are particularly preferable as the microorganism classified as *Pedobacter*; *Haliscomenobacter hydrossis* is particularly preferable as the microorganism classified as *Haliscomenobacter*; *Porphyromonas gingivalis* and *Porphyromonas asaccharolytica* are particularly preferable as the microorganism classified as *Porphyromonas*; *Odoribacter splanchnicus* is particularly preferable as the microorganism classified as *Odoribacter*; *Spirosoma linguale* is particularly preferable as the microorganism classified as *Spirosoma*; *Runella slithyformis* is particularly preferable as the microorganism classified as *Runella*; *Deinococcus radiodurans, Deinococcus geothermalis, Deinococcus deserti, Deinococcus maricopensis, Deinococcus proteolyticus* and *Deinococcus gobiensis* are particularly preferable as the microorganism classified as *Deinococcus*; *Thermus thermophilus* and *Thermus scotoductus* is particularly preferable as the microorganism classified as *Thermus*; *Meiothermus ruber* and *Meiothermus silvanus* are particularly preferable as the microorganism classified as *Meiothermus*; *Oceanithermus profundus* is particularly preferable as the microorganism classified as *Oceanithermus*; *Marinithermus hydrothermalis* is particularly preferable as the microorganism classified as *Marinithermus*; *Gemmatimonas aurantiaca* is particularly preferable as the microorganism classified as *Gemmatimonas*; *Fusobacterium nucleatum* is particularly preferable as the microorganism classified as *Fusobacterium*; *Ilyobacter polytropus* is particularly preferable as the microorganism classified as *Ilyobacter*; *Roseiflexus castenholzii* is particularly preferable as the microorganism classified as *Roseiflexus*; *Herpetosiphon aurantiacus* is particularly preferable as the microorganism classified as *Herpetosiphon*; *Thermomicrobium roseum* is particularly preferable as the microorganism classified as *Thermomicrobium*; *Thermotoga lettingae* is particularly preferable as the microorganism classified as *Thermotoga*; *Thermosipho melanesiensis* and *Thermosipho africanus* are particularly preferable as the microorganism classified as *Thermosipho*; *Fervidobacterium nodosum* is particularly preferable as the microorganism classified as *Fervidobacterium*; *Deferribacter desulfuricans* is particularly preferable as the microorganism classified as *Deferribacter*; *Calditerrivibrio nitroreducens* is particularly preferable as the microorganism classified as *Calditerrivibrio*; *Flexistipes sinusarabici* is particularly preferable as the microorganism classified as *Flexistipes*; *Metallosphaera sedula* is particularly preferable as the microorganism classified as *Metallosphaera*; *Aeropyrum pernix* is particularly preferable as the microorganism classified as *Aeropyrum*; *Pyrobaculum aerophilum, Pyrobaculum islandicum, Pyrobaculum calidifontis* and *Pyrobaculum neutrophilum* are particularly preferable as the microorganism classified as *Pyrobaculum*; *Caldivirga maquilingensis* is particularly preferable as the microorganism classified as *Caldivirga*; *Vulcanisaeta distributa* is particularly preferable as the microorganism classified as *Vulcanisaeta*; *Acidilobus saccharovorans* is particularly preferable as the microorganism classified as *Acidilobus*; *Haloarcula marismortui* is particularly preferable as the microorganism classified as *Haloarcula*; *Haloquadratum walsbyi* is particularly preferable as the microorganism classified as *Haloquadratum*; *Natronomonas pharaonis* is particularly preferable as the microorganism classified as *Natronomonas*; *Halorubrum lacusprofundi* is particularly preferable as the microorganism classified as *Halorubrum*; *Haloterrigena turkmenica* is particularly preferable as the microorganism classified as *Haloterrigena*; *Natrialba magadii* is particularly preferable as the microorganism classified as *Natrialba*; *Halalkalicoccus jeotgali* is particularly preferable as the microorganism classified as *Halalkalicoccus*; *Halogeometricum borinquense* is particularly preferable as the microorganism classified as *Halogeometricum*; *Thermoplasma acidophilum* and *Thermoplasma volcanium* are particularly preferable as the microorganism classified as *Thermoplasma*; *Picrophilus torridus* is particularly preferable as the microorganism classified as *Picrophilus*; *Ferroplasma acidarmanus* is particularly preferable as the microorganism classified as *Ferroplasma*; *Archaeoglobus fulgidus* and *Archaeoglobus veneficus* are particularly preferable as the microorganism classified as *Archaeoglobus*; *Ferroglobus placidus* is particularly preferable as the microorganism classified as *Ferroglobus*; *Polymorphum gilvum* is particularly preferable as the microorganism classified as *Polymorphum*; *Micavibrio aeruginosavorus* is particularly preferable as the microorganism classified as *Micavibrio*; *Simiduia agarivorans* is particularly preferable as the microorganism classified as *Simiduia*; *Leptothrix cholodnii* is particularly preferable as the microorganism classified as *Leptothrix*; *Thiomonas intermedia* is particularly preferable as the microorganism classified as *Thiomonas*; *Rubrivivax gelatinosus* is particularly preferable as the microorganism classified as *Rubrivivax*; *Methylibium petroleiphilum* is particularly preferable as the microorganism classified as *Methylibium*; and *Anaerococcus prevotii* is particularly preferable as the microorganism classified as *Anaerococcus*.

The microorganisms exemplified herein are obtainable from the American Type Culture Collection (ATCC), National Institute of Technology and Evaluation, Biotechnology Division, Biological Resource Center (NBRC), National Institute of Advanced Industrial Science and Technology, Patent Organism Depository (FERM), or the like.

Synthesis Process of Methacrylic Acid Ester

The production of methacrylic acid ester can be performed by the following method. A solution was prepared by adding alcohol or phenol represented by Formula 2 and methacrylyl-CoA to a solvent, and then allowing to dissolve or suspend. Then, AAT is brought into contact with this solution or suspension, and methacrylyl-CoA and the alcohol or phenol is allowed to react while controlling conditions such as temperature. By way of the reaction, a methacrylic group of methacrylyl-CoA is transferred to the alcohol or phenol of Formula 2, thereby causing methacrylic acid ester to be formed.

The solution containing the methacrylyl-CoA and alcohol or phenol represented by Formula 2 is normally prepared in an aqueous medium such as a buffer solution. Herein, in order to cause the reaction to progress smoothly, it is possible to control the osmolar concentration and/or ion strength by way of an osmotic pressure regulator or the like. As the osmotic pressure regulator, it is sufficient if a water-soluble substance added with the object of adjusting the osmotic pressure of the solution such as the inside of the cell so as to make isotonic or hypertonic, and for example, is a salt or saccharide, and preferably a salt. The salt is preferably a metallic salt, more preferably an alkali metal salt, even more preferably an alkali metal halide, and for example, sodium chloride and potassium chloride can be exemplified. The saccharide is preferably a monosaccharide or oligosaccharide, more preferably a monosaccharide or disaccharide, and for example, glucose, sucrose, mannitol and the like can be exemplified. The osmotic pressure regulator is preferably added at a concentration of at least 1 mM, and it is particularly preferable to regulate so as to make isotonic or hypertonic compared to a solution inside the biological cell used.

In addition, with the object of separating the methacrylic acid ester thus formed, an organic solvent can be added in advance to make react in a two-phase system. As the organic solvent, for example, a linear, branched or cyclic, saturated or unsaturated aliphatic hydrocarbon, saturated or unsaturated aromatic hydrocarbon, or the like can be used individually or by mixing two or more types. More specifically, for example, hydrocarbon solvents (e.g., pentane, hexane, cyclohexane, benzene, toluene, xylene, etc.), halogenated hydrocarbon solvents (e.g., methylene chloride, chloroform, etc.), ether solvents (e.g., diethyl ether, dipropyl ether, dibutyl ether, tert-butylmethyl ether, dimethoxyethane, etc.), ester solvents (e.g., methyl formate, methyl acetate, ethyl acetate, butyl acetate, methyl propionate), and the like can be exemplified. By adding these organic solvents, the methacrylic acid ester formed will migrate to the organic phase, and the reaction may progress efficiently.

The molar ratios and concentrations of methacrylyl-CoA and the alcohol or phenol represented by Formula 2 in the reaction solution are arbitrary, and not particularly limited. In addition, the amount of AAT used or reaction conditions are determined as appropriate according to the raw materials used. Usually, the concentration of each raw material is set to the range of 0.0000001 to 10% by mass in the case of methacrylyl-CoA, and the alcohol or phenol is added at a concentration of 0.1 to 1000 times by moles, preferably 0.5 to 50 times by moles, relative to the methacrylyl-CoA used.

Various other conditions such as the reaction temperature or reaction time are determined as appropriate according to the raw materials used, activity of enzyme, etc., and are not particularly limited; however, it is sufficient normally if allowed to react at 5 to 80° C. for 1 hour to 1 week. At 10 to 70° C., it is preferably for 1 to 120 hours, more preferably at least 3 hours, and 4 or more hours is even more preferable. It is preferable to select conditions by which the reaction completes at such conditions. The pH of the reaction solution is not particularly limited so long as the reaction efficiently progresses; however, for example, it is a range of pH 4 to 10, and preferably pH 5.5 to 8.5.

As ideal conditions for causing methacrylic acid ester to collect in at least 0.001 mM, preparing so that the concentration of methacrylyl-CoA under the condition of pH 5.5 to 7.5 is in the range of 0.000001 to 1% by mass directly or indirectly, and the alcohol or phenol is adjusted to a concentration so as to be 1 to 50 times by moles relative to the methacrylyl-CoA used. Then, the temperature is adjusted to the range of 20 to 40° C., and reaction is allowed for at least 3 hours. It is also possible to continuously supply these raw materials (substrate) so as to be in the aforementioned ranges, and the accumulation concentration of product can be raised by doing so.

Conducting the present reaction under reduced pressure or aeration conditions is also effective. It is because, under these conditions, the methacrylic acid ester thus formed can be continuously separated, a result of which the reaction may progress efficiently.

In the case of producing methacrylic acid ester using methacrylyl-CoA transformed by action of ACD with isobutyryl-CoA as the raw material or methacrylyl-CoA transformed by action of ECH from 3-hydroxyisobutyryl-CoA, it is preferable to implement by adjusting so as to be in the range of these conditions. It should be noted that the methacrylyl-CoA synthesis reaction from ACD or ECH can be conducted by a known method (for example, as reaction conditions for ACD, the conditions described in Microbiology (1999), 145, pp. 2323-2334). By combining with yet another biological reaction, continuous reaction (fermentative production) within an organism for methacrylic acid ester becomes possible.

The methacrylic acid ester formed by the method of the present invention can be qualitatively or quantitatively analyzed by way of gas chromatography (GC), high performance liquid chromatography (HPLC), or the like as necessary.

Isolation of methacrylic acid ester from the reaction solution can be performed by an individual or combination of known purification methods such as distillation, thin-film distillation, solvent extraction and column separation. In addition, the obtained methacrylic acid ester can polymerize by a typical method, and used without inferiority in conventional uses.

The methacrylic acid ester obtained in this way or polymer thereof can remarkably reduce the energy, resources and load on the environment, and has an extremely great social value as a low-environmental load material compared to conventional chemicals with petroleum products as starting materials.

2. Method for Producing Methacrylic Acid Ester from Precursor by Genetically Modified Microorganism Recombinant Microorganism Having Methacrylic Acid Ester Formability from Precursor As mentioned in the foregoing, with the present invention, it is also possible to synthesize methacrylic acid ester from a precursor such as isobutyryl-CoA, 3-hydroxyisobutyryl-CoA or 2-isovaleric acid, by introducing ACD gene, ECH gene, BCKAD gene or the like as necessary to a microorganism to which AAT gene has been introduced.

"Precursor" indicates a compound that is inducible to methacrylyl-CoA, and indicates isobutyryl-CoA or 3-hydroxyisobutyryl-CoA, and further, the matter of a substance inducible to these two compounds. As the substance inducible to two compounds, for example, acids such as 2-oxoisovaleric acid, isobutyric acid, 3-hydroxy isobutyric acid, acetic acid, pyruvic acid, lactic acid, acetoacetic acid, butyric acid, propionic acid, malic acid, fumaric acid, citric acid and succinic acid; amino acids such as valine, alanine, leucine, lysine and glutamic acid; and saccharides such as glucose, fructose and xylose can be exemplified.

To cause methacrylic acid ester to form from these precursors, it is also possible to utilize various metabolic pathways naturally possessed by the host microorganism. Genes can be introduced or made deficient as necessary.

(1) Host Microorganism

As the host microorganism, it is not particularly limited so long as being a host having enzymes for forming methacrylyl-CoA from the precursor and expression capability of AAT; however, as for bacterium, *Rhodococcus, Pseudomonas, Corynebacterium, Bacillus, Streptococcus, Streptomyces*, etc. can be exemplified, as for yeast, *Saccharomyces, Candida, Shizosaccharomyces* and *Pichia*, and as for filamentous fungus, *Aspergillus*, etc. can be exemplified.

A microorganism of *Rhodococcus* genus is preferable as the host. The reason thereof is because of the knowledge arrived at by experimentally confirming in the course of the present invention that a microorganism of *Rhodococcus* genus has valine assimilativity, and finding that, by utilizing this function, it is possible to apply to methacrylic acid ester formation by the route shown in FIG. 2.

For example, one type selected from the following microorganisms can be used individually, or by combining two or more types. As microorganisms classified as *Rhodococcus* sp., for example, *Rhodococcus rhodochrous, Rhodococcus erythropolis, Rhodococcus equi, Rhodococcus rhodnii, Rhodococcus corallinus, Rhodococcus rubropertinctus, Rhodococcus coprophilus, Rhodococcus globerulus, Rhodococcus chlorophenolicus, Rhodococcus luteus, Rhodococcus aichiensis, Rhodococcus chubuensis, Rhodococcus maris, Rhodococcus fascines* and the like can be exemplified.

As a preferred example, *Rhodococcus erythropolis* can be exemplified. As more preferred strains, *Rhodococcus erythropolis* strain PR-4, *Rhodococcus erythropolis* strain KA2-5-1, *Rhodococcus erythropolis* strain IGTS8, *Rhodococcus erythropolis* strain D-1, *Rhodococcus erythropolis* strain H-2, *Rhodococcus erythropolis* strain N1-36, *Rhodococcus erythropolis* strain 1-19, *Rhodococcus erythropolis* strain ECRD-1, *Rhodococcus erythropolis* strain B1, *Rhodococcus erythropolis* strain SY-1, *Rhodococcus erythropolis* strain UM3, *Rhodococcus erythropolis* strain UM9, *Rhodococcus equi* strain T09, or the like can be exemplified, and particularly preferably, *Rhodococcus erythropolis* strain PR-4 can be exemplified. Furthermore, derivatives of these strains are included.

As derivatives, variant strains obtained by inducing gene mutation in a microorganism having methacrylyl-CoA formability by way of a change in culture conditions (e.g., medium composition, temperature, etc.), chemical or physical treatment (e.g., γ radiation, etc.), genetically modified strains for which activity has been enhanced in the following way, or activity has been made deficient or reduced are included.

Activity enhancement indicates the expression level of enzyme gene (irrespective of origin) increasing in the microorganism based on the gene introduced from outside the bacterial cell to the microorganism, and in addition to introducing genes encoding enzymes from outside the bacterial cell of the microorganism to inside the bacterial cell, includes enhancing the enzyme activity as a result of causing the enzyme gene to be highly expressed by enhancing the promoter activity of the enzyme gene retained on the genome by the microorganism, or substituting with another promoter, or alternatively, reducing or inactivating the repressor activity of the enzyme gene.

The genetically modified strain may be a modified strain arrived at by performing genetic modification causing the activity of enzyme inhibiting the methacrylyl-CoA synthesis reaction to be knocked out or decreased. Activity "deficient" or "decrease" indicates the expression of the enzyme gene being entirely lost or reduced in this microorganism, and in addition to substitution, deletion or insertion occurring for this enzyme gene, includes decreasing the enzyme activity as a result of suppressing the expression of enzyme gene by decreasing the promoter activity of an enzyme gene retained on the genome by the microorganism or substituting with another promoter, or alternatively enhancing or activating the repressor activity of this enzyme gene. It should be noted that these genetic modifications may be performed following a conventional method.

As a preferred modified strain in the case of conducting methacrylic acid ester production by the route shown in FIG. 2, a modified strain having at least one characteristic of (a) or (b) shown below can be exemplified.

(a) Methacrylyl-CoA formation activity is being enhanced by BCKAD gene and/or ACD gene being introduced.

(b) Methacrylyl-CoA formation activity is being enhanced by knock out or inactivation of ECH gene, 3-hydroxy isobutyryl-CoA hydrolase gene and/or 3-hydroxy isobutyric acid dehydrogenase gene. Knock out or deactivation is performed by substituting, deleting or inserting an entirety of the gene or part of the nucleotide sequence.

(2) Inserted Gene

It becomes necessary to introduce respective genes of enzymes for forming methacrylyl-CoA from the precursor and AAT gene as necessary to the host. Various enzymes naturally possessed by the host microorganism can be utilized as is. Alternatively, it is also possible to enhance activity by way of gene introduction as necessary.

According to the host and synthesis route, the enzyme for forming methacrylyl-CoA from the precursor is selected as appropriate or optimized, and is not particularly limited; however, hereinafter, the necessary enzyme genes for methacrylic acid ester formation by the route shown in FIG. 2 will be described in detail using a microorganism of *Rhodococcus* genus as the host.

(2-1) Alcohol Acyltransferase (AAT)

The AAT used in the present invention is not particularly limited so long as having ability to produce methacrylic acid ester with methacrylyl-CoA and alcohol or phenol as raw materials, and the kind and origin thereof are not of concern. One of plant origin is preferable as the enzyme source, and as representative sources thereof, those originating from any order selected from the group consisting of the aforementioned Zingiberales, Rosales, Ericales, Cucurbitales, Brassicales and Laurales can be exemplified.

(2-2) Acyl-CoA Dehydrogenase (ACD)

The ACD used in the present invention is not particularly limited so long as having an ability to form methacrylyl-CoA from acyl-CoA, and the source and type thereof are not of concern. Those derived from microorganism are preferable, and representative ones are as shown before.

More preferably, it is derived from *Rhodococcus erythropolis*, and as preferred strains, *Rhodococcus erythropolis* strain PR-4, *Rhodococcus erythropolis* strain KA2-5-1, *Rhodococcus erythropolis* strain IGTS8, *Rhodococcus erythropolis* strain D-1, *Rhodococcus erythropolis* strain H-2, *Rhodococcus erythropolis* strain N1-36, *Rhodococcus erythropolis* strain 1-19, *Rhodococcus erythropolis* strain ECRD-1, *Rhodococcus erythropolis* strain B1, *Rhodococcus erythropolis* strain SY-1, *Rhodococcus erythropolis* strain UM3, *Rhodococcus erythropolis* strain UM9, *Rhodococcus*

*equi* strain T09, or the like can be exemplified, and particularly preferably, *Rhodococcus erythropolis* strain PR-4 can be exemplified.

The nucleotide sequence of ACD gene derived from *Rhodococcus erythropolis* strain PR-4 is shown in SEQ ID NO. 33, and the amino acid sequence coded by this nucleotide sequence is shown in SEQ ID NO. 32. It should be noted that amino acid sequences in which one or a plurality of amino acids in the amino acid sequence shown in SEQ ID NO. 32 have been substituted, deleted or added are included, and genes coding proteins having activity to form methacrylyl-CoA from acyl-CoA are also included in the ACD gene of the present invention. In addition, in the ACD gene of the present invention, genes coding protein having activity to produce methacrylic acid ester from acyl-CoA expressing at least 90% identity with the protein consisting of the amino acid sequence shown by SEQ ID NO. 32, preferably at least 95%, more preferably at least 99.5%, and even more preferably at least 99.9% are also included.

Furthermore, in the ACD gene of the present invention, genes hybridizing under stringent conditions to a polynucleotide having the complementary nucleotide sequence to the nucleotide sequence shown by SEQ ID NO. 33, and coding proteins having activity to form methacrylic acid ester from acyl-CoA are also included. Furthermore, in the ACD gene of the present invention, when calculating using the nucleotide sequence shown in SEQ ID NO. 33, BLAST, etc. (e.g., default, i.e. initial setting, parameters), genes coding proteins having activity to form methacrylic acid ester from acyl-CoA and alcohol consisting of a nucleotide sequence having identity of at least 80%, more preferably at least 90%, and most preferably at least 95% are also included. In addition, the codons of the above-mentioned ACD gene may be changed according to the codon frequency of use in the microorganism used in transformation.

DNA coding the above-mentioned AAT gene and/or ACD gene is introduced to a microorganism belonging to *Rhodococcus* sp., and used to cause transcription/translation to proteins in this microorganism. The DNA introduced to this microorganism is preferably in the form incorporated in a vector.

(3) Preparation of Recombinant Microorganism

DNA coding the above-mentioned AAT gene and/or ACD gene is introduced to the host microorganism, and used to cause transcription/translation to proteins in this microorganism. The DNA introduced to this microorganism is preferably in the form incorporated in a vector. In other words, each gene is incorporated into an expression vector that can be expressed by the host cell, and this is introduced to the host cell.

The vector is not particularly limited so long as being autonomously replicable in the host cell, and retaining the AAT gene and/or ACD gene, and it is possible to use vectors suited to the respective microorganisms. As the vector for introducing DNA to microorganism belonging to *Rhodococcus* sp., for example, it is possible to use well-known vectors such as pK1, pK2, pK3 and pK4, as well as pSJ034 (refer to Japanese Unexamined Patent Application, Publication No. H10-337185), pSJ023 and pSJ002 (refer to Japanese Unexamined Patent Application, Publication No. H10-24867), and pSJ201 and pLK005 (not limited to these). pSJ023 is deposited in the National Institute of Advanced Industrial Science and Technology, Patent Organism Depository as transformant *Rhodococcus rhodochrous* ATCC12674/pSJ023 (FERMBP-6232).

The insertion of the above-mentioned AAT gene and/or ACD gene to the vector can be carried out using gene recombination technology known to those skilled in the art. For example, it is possible to utilize a method using restriction enzyme cleavage and ligation, a method using topoisomerase, an In Fusion kit (Takara Bio), and the like. The gene inserted into the vector is inserted successively downstream of a promotor capable of regulating transcription/translation of proteins encoded by the respective genes in the host organism. In addition, if necessary, an appropriate linker may be added upon insertion. In addition, as necessary, a terminator sequence, enhancer sequence, splicing signal sequence, polyA addition signal sequence, ribosome-binding sequence such as the SD sequence or Kozak sequence, selection marker gene, etc. usable in the host organism into which genes are trying to be introduced can be linked. As an example of the selection marker gene, in addition to drug resistant genes such as ampicillin-resistant gene, tetracycline-resistant gene, neomycin-resistant gene, kanamycin-resistant gene and chloramphenicol-resistant gene, genes imparting intracellular biosynthesis of nutrients such as amino acids and nucleic acids, or genes coding fluorescent proteins such as luciferase can be exemplified. Accompanying insertion, a part of the amino acid sequence coded by the DNA may be substituted.

From the above point, it is particularly preferable to use pLK005 acquired by performing variation treatment on pK4 as the vector. The AAT gene or ACD gene is linked/inserted so as to be disposed downstream of 3' of the promoter of pLK005, and an expression plasmid vector that expresses AAT gene and/or ACD gene can be constructed by the promoter.

In the vector, any gene selected from the AAT gene cluster or ACD gene cluster may be inserted, and a plurality of genes may be inserted. In the case of a gene inserted in a vector being used, "plurality" can be inserting 2 to 5, 2 to 4, and preferably 2 or 3 genes. In addition, in the case of a plurality of genes being inserted into one vector, these genes preferably form an operon. Herein, "operon" is a nucleic acid sequence unit constituted from one or more genes transcribed under the control of the same promoter.

The above-mentioned genes, and preferably genes in the form of a vector, are inserted to the host microorganism by a method known to those skilled in the art. The introduction method of the recombinant vector to the host organism is not particularly limited so long as being a method suited to the host microorganism and, for example, the electroporation method, spheroplast method, lithium acetate method, calcium phosphate method, lipofection method, conjugational transfer method and the like can be exemplified.

Method for Producing Methacrylic Acid Ester

The recombinant microorganism to which the required genes such as AAT gene and/or ACD gene are introduced is brought into contact with the precursor to produce methacrylic acid ester. Herein, "contact" indicates exposure treating for a fixed time the microorganism and a substance (precursor). More specifically, the microorganism is cultured in an aqueous medium containing precursor (raw material), etc., or a culture of the microorganism is added to the aqueous medium containing raw material, and suspended/mixed, to obtain methacrylic acid ester in the aqueous medium and/or gas phase. Upon doing so, it is of no concern if there is proliferation of microorganism. In this process, a mixture containing recombinant microorganism, and methacrylic acid ester is obtained.

"Aqueous medium" indicates water or an aqueous solution with water as a principle component, and also includes those in which undissolved liquid/solid are dispersed. "Gas phase" refers to a portion occupied by gas, steam, etc.

excluding a portion occupied by liquid (culture medium, etc.) in the culture tank (vessel culturing microorganism) or reactor (vessel carrying out reaction). "Culture" indicates that obtained by way of a culturing of bacterial cells, broth, noncellular extract, cellular membrane, or the like.

(1) Production of Methacrylic Acid Ester from Culturing

In the present invention, production of methacrylic acid ester is performed by causing methacrylic acid ester to be form and accumulate in culture bacterial cells or the culture by culturing gene recombinant microorganism to which AAT gene has been introduced in an aqueous medium containing the precursor, and recovering the methacrylic acid ester from the culture bacterial cell, culture or culture vessel gas phase.

The culture medium used in the culturing of microorganism is a solid medium or liquid medium enabling sufficient proliferation that contains nutrients at least including various carbon sources. In the case of precursor being usable as the carbon source, it can be used as the carbon source.

The concentration of carbon source or precursor in the culture medium is not particularly limited so long as enabling the production of methacrylic acid ester. The concentration, for example, is set to 0.05 to 20 (w/v) %, preferably 0.1 to 15 (w/v) %, and more preferably 0.2 to 10 (w/v) %. At least 0.2 (w/v) % is used because the methacrylic acid productivity of microorganisms increases, and it is set to no more than 10 (w/v) % because a dramatic improvement in effect is not recognized even if increasing to more than this.

In the production of methacrylic acid ester by culturing, alcohol or phenol is added depending on the target methacrylic acid ester. The alcohol or phenol used is preferably one shown by Formula 2.

The concentration of alcohol or phenol in the culture medium is not particularly limited so long as enabling methacrylic acid ester to be produced. The concentration, for example, is set to 0.01 to 20 (w/v) %, preferably 0.05 to 10 (w/v) %, and more preferably 0.1 to 5 (w/v) %. In addition, these can also be added to the culture medium in advance, or can be added continuously or intermittently by dividing into two or more occurrences, while performing culturing.

In the culture medium, inorganic nitrogen sources, inorganic metal salts or the like may be added. As inorganic nitrogen sources, for example, inorganic acids or organic acids of ammonium salts such as ammonium chloride, ammonium sulfate, ammonium acetate and ammonium phosphate, and the like can be used.

The concentration of nitrogen source in the culture medium is not particularly limited so long as enabling methacrylic acid ester to be produced. The concentration, for example, is set to 0.01 to 10 (w/v) %, preferably 0.05 to 8 (w/v) %, and more preferably 0.1 to 4 (w/v) %.

As inorganic metal salts, for example, potassium dihydrogen phosphate, potassium monophosphate, magnesium phosphate, magnesium sulfate, sodium chloride, ferrous sulfate, manganese sulfate, copper sulfate, calcium carbonate, etc. can be used.

The concentration of inorganic salts in the culture medium is not particularly limited so long as enabling methacrylic acid ester to be produced. The concentration, for example, is set to 0.001 to 1.6 (w/v) %, preferably 0.005 to 1.3 (w/v) %, and more preferably 0.01 to 1 (w/v) %. At least 0.1 (w/v) % is used because the methacrylic acid productivity of microorganisms increases, and it is set to no more than 1 (w/v) % because a dramatic improvement in effect is not recognized even if adding more than this.

Additionally, trace metals, vitamins, etc. are added as necessary to the culture medium. In addition, various organic substances, inorganic substances, surfactant, commonly used defoaming agent, etc. necessary in the breeding of the microorganism can be additionally added to the culture medium as necessary.

Seeding of the genetically modified microorganism to the culture medium may be carried out by a conventional, known technique. The culture method also is not particularly limited, and it is possible to use a known technique such as shaking culture, aerated and agitated culture, and static culture.

The culturing conditions are not particularly limited so long as the genetically modified organism breeds and forms methacrylic acid ester. Culturing may be carried out under aerobic conditions or may be carried out under anaerobic conditions.

The pH, temperature and culturing time are not particularly limited so long as conditions allowing the genetically modified microorganism to breed and form methacrylic acid ester. The pH is preferably set to 3 to 10, more preferably 4 to 9, and even more preferably 5 to 8. The temperature is preferably set to 10 to 45° C., more preferably 15 to 40° C., and even more preferably 20 to 35° C. The culturing time is preferably 10 to 1000 hours, more preferably 15 to 480 hours, and even more preferably 20 to 240 hours.

These culturing conditions are appropriately selected or optimized for every strain so as to maximize the ratio of yield of methacrylic acid ester relative to the utilized amount of carbon source or precursor. It should be noted that the yield of methacrylic acid ester can be adjusted by appropriately adjusting the amount of carbon source and culturing conditions.

As ideal conditions for causing methacrylic acid ester to accumulate in at least 0.001 mM, under a pH condition of 5.5 to 7.5, the concentration of carbon source or precursor in the culture medium is directly or indirectly maintained to at least 0.1%, the concentration of alcohol or phenols is directly or indirectly maintained to at least 0.1%, the temperature is adjusted to the range of 20 to 40° C., and allowed to react for at least 3 hours. Furthermore, it is preferable in order to obtain efficient productivity to maintain a state in which the concentration of microorganism in the culture solution is high in a range in which the environment of the culture solution does not become inappropriate for proliferation of the microorganism or cultured cells and the ratio of cells dying does not rise and, for example, by maintaining in at least 2 g/L as a dry weight, favorable production efficiency is obtained, and the accumulation concentration of production can be raised.

(2) Production of Methacrylic Acid Ester from Resting Microorganism Reaction

With the method for producing methacrylic acid ester according to the present invention, the following method can be employed in addition to the method by culturing genetically modified microorganism as described above. The genetically modified microorganism does not need to have reproductive activity, and a precultured culture can be brought into contact with an aqueous medium containing precursor to produce methacrylic acid ester by resting microorganism reaction unaccompanied by substantial proliferation.

The concentration of the precursor used in resting microorganism reaction may be the same as the above-mentioned case of production of methacrylic acid ester from culturing. The alcohol or phenol used in resting microorganism reaction and the concentration thereof may be the same as the above-mentioned case of production of methacrylic acid ester by culturing.

Inorganic metal salts, etc. may be added to the reaction solution. As inorganic metal salts, for example, potassium dihydrogen phosphate, potassium monophosphate, magnesium phosphate, magnesium sulfate, sodium chloride, ferrous sulfate, manganese sulfate, copper sulfate, calcium carbonate, etc. can be used.

The concentration of inorganic salts in the reaction solution is not particularly limited so long as enabling methacrylic acid ester to be produced. The concentration, for example, is set to 0.0001 to 2 (w/v) %, preferably 0.0003 to 1.3 (w/v) %, and more preferably 0.001 to 1 (w/v) %.

Additionally, trace metals, vitamins, etc. are added as necessary to the reaction solution. In addition, various organic substances, inorganic substances, surfactant, commonly used defoaming agent, etc. necessary in the reaction can be additionally added to the reaction solution as necessary.

In resting microorganism reaction, the culture solution of precultured genetically modified microorganism is used as is, or bacterial cells recovered by filtering, centrifuging or the like are used. The recovered culture is resuspended in an appropriate buffer solution or the like, and can be used by establishing in any bacteria concentration. For the buffer solution or the like, a normal saline solution, potassium phosphate buffer solution, tris-hydrochloric acid buffer solution, glycine-sodium hydroxide buffer solution, boric acid-sodium hydroxide buffer solution, or the like is used.

In addition, in the resting microorganism reaction, the processed product of the recovered culture (e.g., homogenate, crude enzyme, purified enzyme, etc.) can also be used. Furthermore, it may be fixed to an appropriate carrier by a known method, and this fixation product may be used in reaction.

The reaction conditions are not particularly limited so long as forming methacrylic acid ester. The reaction may be carried out under aerobic conditions or may be carried out under anaerobic conditions. The reaction method is also not particularly limited, and a well-known technique such as shaking reaction, aerated and agitated reaction, and static reaction can be used.

The pH, temperature and reaction time are not particularly limited so long as conditions that can form methacrylic acid ester. The pH is preferably set to 3 to 10, more preferably 4 to 9, and even more preferably 5 to 8. The temperature is preferably set to 10 to 45° C., more preferably 15 to 40° C., and even more preferably 20 to 35° C. The reaction time is preferably 5 to 180 hours, more preferably 10 to 150 hours, and even more preferably 15 to 120 hours.

These reaction conditions are appropriately selected or optimized for every strain so as to maximize the ratio of yield of methacrylic acid ester. It should be noted that the yield of methacrylic acid ester can be adjusted by appropriately adjusting the reaction conditions.

As ideal conditions for causing methacrylic acid ester to accumulate in 0.001 mM, under a pH condition of 5.5 to 7.5, the concentration of carbon source or precursor in the culture medium is directly or indirectly maintained to at least 0.1%, the concentration of alcohol or phenols is directly or indirectly maintained to at least 0.1%, the temperature is adjusted to the range of 20 to 40° C., and allowed to react for at least 3 hours. Furthermore, maintaining a state in which the concentration of microorganism in the reaction solution is high is preferable to obtain efficient productivity, and for example, by maintaining in at least 2 g/L as a dry weight, favorable production efficiency is obtained, and the accumulation concentration of product can be improved.

In the method for producing methacrylic acid ester according to the present invention, the aforementioned production of methacrylic acid ester from culturing and the production of methacrylic acid ester from resting microorganism reaction may be carried out by combining as appropriate. By combining the two methods, the more efficient production of methacrylic acid ester becomes possible.

(3) Recovery of Methacrylic Acid Ester

The methacrylic acid ester formed in the culture medium or reaction solution and the formed amount thereof can be detected and measured using a common method such as of high-performance liquid chromatography and LC-MS. In addition, the methacrylic acid ester volatilized in the gas phase of the culture container or reaction container (head space part) and formed amount thereof can be detected and measured using a common method such as gas chromatography.

The methacrylic acid ester can be separated and purified from the culture medium or reaction solution using an appropriate combination, as necessary, of well-known operations such as filtration, centrifugation, vacuum concentration, ion exchange or adsorption chromatography, solvent extraction, distillation and crystallization.

EXAMPLES

Hereinafter, although the present invention will be specifically explained by way of Examples; however, the scope of the present invention is not to be limited to the scope of these examples.

Example 1: Synthesis of Isobutyl Methacrylate

The skin of a banana was removed, the sarcocarp was sliced to about 1 millimeter thickness with a cutter, and this was further divided into four. Two grams of sliced banana, 2 ml of a solution containing 2.3 mM methacrylyl-CoA and 0.35 M of KCl and 5 µl of isobutyl alcohol were added in order to a 100 ml flask. It was sealed and allowed to react at 30° C. The reaction mixture containing Isobutyl methacrylate formed after 1, 2 or 3 hours was collected in a 100 ml flask with 150 µl of head space, and analysis was performed with the GC conditions below. The results thereof are shown in Table 1.

TABLE 1

Generated amount of isobutyl methacrylate

| Time | Generated amount of isobutyl methacrylate (mM) |
|---|---|
| 1 | 0.19 |
| 2 | 0.38 |
| 3 | 0.45 |

GC Analysis Conditions
 column: DB-WAX, 30 m×0.32 mm
 column temperature: 50° C.·5 min→5° C./min→100° C. (15 min total)
 carrier gas: He
 inject: 200° C. splitless (sampling time 1 min)
 detect: 250° C. FID
 injection volume: 150 µl It should be noted that the concentration of methacrylic acid ester was calculated by adjusting an aqueous solution of a known initial concentration, placing 2 ml of the same aqueous solution in a 100 ml flask, and after incubating for 30 min at 30° C., collecting the head space by the same method, subjecting to GC analysis, and preparing a calibration curve.

Example 2: Synthesis of Butyl Methacrylate

Except for using n-butyl alcohol in place of isobutyl alcohol, it was conducted similarly to Example 1. The results thereof are shown in Table 2.

TABLE 2

Generated amount of butyl methacrylate

| Time | Generated amount of butyl methacrylate (mM) |
|---|---|
| 2 | 0.20 |
| 5.5 | 0.30 |

Example 3: Synthesis 2 of Butyl Methacrylate

Two grams of a plant piece shown in Table 3, 2 ml of a solution containing 2.3 mM of methacrylyl-CoA and 0.35 M KCl and 10 µl of n-butyl alcohol were added in order to a 100 ml flask. It was sealed and allowed to react at 30° C. Analysis of the methacrylic acid ester was conducted similarly to Example 1. The results thereof are shown in Table 3.

TABLE 3

Generated amount of butyl methacrylate

| Plant | Part used | Reaction time | Generated amount of butyl methacrylate (mM) |
|---|---|---|---|
| Strawberry | Sliced sacrocarp to about 1 mil thickness | 3 | 0.010 |
| Kiwi | Sliced sacrocarp to about 1 mil thickness | 5 | 0.012 |
| Apple | Sliced pericarp to about 1 mil thickness | 5 | 0.016 |
| Melon | Sliced sacrocarp to about 1 mil thickness | 6 | 0.015 |
| Pear | Sliced pericarp to about 1 mil thickness | 4 | 0.013 |
| Papaya | Sliced pericarp to about 1 mil thickness | 4 | 0.027 |
| Avocado | Sliced pericarp to about 1 mil thickness | 6 | 0.035 |
| Blueberry | Sliced pericarp to about 1 mil thickness | 6 | 0.009 |
| *Prunus mume* | Sliced pericarp to about 1 mil thickness | 4 | 0.002 |

Example 4: Synthesis of Ethyl Methacrylate

Two grams of plant piece shown in Table 4, 2 ml of a solution containing 2.3 mM of methacrylyl-CoA and 0.35 M KCl and 6.4 µl of ethyl alcohol were added in order to 100 ml flask. It was sealed and allowed to react at 30° C. Analysis of the methacrylic acid ester was conducted similarly to Example 1. The results thereof are shown in Table 4.

TABLE 4

Generated amount of ethyl methacrylate

| Plant | Part used | Reaction time | Generated amount of ethyl methacrylate (mM) |
|---|---|---|---|
| Apple | Sliced pericarp to about 1 mil thickness | 5 | 0.110 |
| Papaya | Sliced pericarp to about 1 mil thickness | 6 | 0.003 |
| Avocado | Sliced pericarp to about 1 mil 6 thickness | 6 | 0.006 |

Example 5: Synthesis of Ethyl Methacrylate

Two grams of a plant piece shown in Table 5, 2 ml of a solution containing 2.3 mM of methacrylyl-CoA and 0.35 M KCl and 4.4 µl of methyl alcohol were added in order to a 100 ml flask. It was sealed and allowed to react at 30° C. Analysis of the methacrylic acid ester was conducted similarly to Example 1. The results thereof are shown in Table 5.

TABLE 5

Generated amount of methyl methacrylate

| Plant | Part used | Reaction time | Generated amount of ethyl methacrylate (mM) |
|---|---|---|---|
| Apple | Sliced pericarp to about 1 mil thickness | 5 | 0.043 |
| Papaya | Sliced pericarp to about 1 mil thickness | 6 | 0.004 |
| Avocado | Sliced pericarp to about 1 mil 6 thickness | 6 | 0.007 |

Reference Example 1: Preparation of Competent Cell

*E. coli* JM109 was innoculated in 1 mL of LB medium (1% Bacto tryptone, 0.5% Bacto yeast extract, 0.5% NaCl), precultured aerobically at 37° C. for 5 hours, 0.4 mL of the culture was added to 40 mL of SOB medium (2% Bacto tryptone, 0.5% Bacto yeast extract, 10 mM NaCl, 2.5 mM KCl, 1 mM MgSO$_4$, 1 mM MgCl$_2$), and was cultured at 18° C. for 20 hours. After harvesting this culture by centrifugation, 13 mL of a chilled TF solution (20 mM PIPES-KOH (pH 6.0), 200 mM KCl, 10 mM CaCl$_2$, 40 mM MnCl$_2$) was added, and left to stand for 10 minutes at 0° C. Subsequently, after re-centrifuging to remove supernatant, the precipitated *E. coli* was suspended in 3.2 mL of cold TF solution, 0.22 mL of dimethylsulfoxide was added thereto, and left to stand for 10 minute at 0° C. to prepare a competent cell.

Example 6: Preparation of Plant-Derived AAT Gene-Introduced Recombinant *E. coli*

The plant-derived AAT genes shown in SEQ ID NOS: 2, 4 and 6 were entrusted for synthesis by Takara Bio Inc. Apple AAT
(MpAAT1): amino acid sequence (SEQ ID NO: 1), nucleotide sequence (SEQ ID NO: 2)
Strawberry AAT (SAAT): amino acid sequence (SEQ ID NO: 3), nucleotide sequence (SEQ ID NO: 4)

Strawberry AAT (VAAT): amino acid sequence (SEQ ID NO: 5), nucleotide sequence (SEQ ID NO: 6)

These synthesized gene segments were inserted in vector pMD19, and respectively named pAAT001 to 003. (Table 6) With these pAAT001 to 003 as templates, DNA fragments coding AAT gene were prepared by way of the PCR method, designing an oligonucleotide so as to be a form in which a restriction endonuclease recognition site enabling easy introduction to an expression vector was added.

Oligonucleotide Primer

```
                                         (SEQ ID NO. 11)
MMA-044:  5'-GTTTGCACGCCTGCCGTTCGACG-3'

(SEQ ID NO. 12)
MMA-045:  5'-CGGTACGCGCGGATCTTCCAGAG-3'
```

Reaction Solution Composition
Sterilized water 22 µL
2× PrimeSTAR (manufactured by Takara Bio) 25 µL
Forward primer 1 µL
Reverse primer 1 µL
Genomic DNA 1 µL
Total amount 50 µL
Temperature Cycle
30 cycles of reaction at 98° C. 10 seconds, 55° C. 15 seconds and 72° C. 150 seconds A band of obtained amplification product was purified by a QIAquick Gel Extraction Kit (QIAGEN). The respective purified DNA was digested with restriction enzyme PagI (cleavage recognition site included in Forward Primer) and Sse8387I (cleavage recognition site included in Reverse Primer). Separation was performed by agarose gel electrophoresis, the target band was excised from the gel, and purification was performed. In purification, using a Gel/PCR Purification Kit (manufactured by FAVORGEN), it was eluted to 30 µL of sterile water.

The purified DNA (5 µL), vector pTrc99A digested with NcoI and Sse8387I (1 µL), distilled water (4 µL) and solution I (DNA Ligation Kit ver. 2 (Takara Bio)) (10 µL) were mixed, and the vector was ligated with PCR amplification product by incubating for 12 hours at 16° C.

To 200 µL of the compenent cell prepared by the method of Reference Example 1, 10 µL of the above-mentioned ligation solution was added and left to stand at 0° C. for 30 minutes, followed by imparting heat shock at 42° C. for 30 seconds and cooling to 0° C. for 2 minutes, after which 1 mL of SOC culture medium (20 mM glucose, 2% Bacto tryptone, 0.5% Bacto yeast extract, 10 mM NaCl, 2.5 mM KCl, 1 mM MgSO$_4$, 1 mM MgCl$_2$) was added and shaking cultured at 37° C. for 1 hour.

After culturing, 100 µL of culture media was inoculated to LBAmp nutrient agar (LB culture medium containing 100 mg/L ampicillin, 1.5% agar), and further cultured at 37° C. A plurality of transformant colonies grown on nutrient agar was cultured overnight at 37° C. in 1.5 mL of LBAmp culture medium (LB culture medium containing 100 mg/L ampicillin), and after harvesting, plasmid DNA was prepared using a QIAprep Spin Miniprep kit (QIAGEN).

For the obtained recombinant respective plasmid DNA, the nucleotide sequence thereof was confirmed using a CEQ DTCS Quick Start Kit and fluorescent sequencer CEQ 2000XL DNA Analyzer (both Beckman Coulter, USA), and were named plasmid pAAT101 to pAAT103 (Table 6).

For the pET16b vectors, AAT gene was introduced by similar operations, and the obtained plasmids were named pAAT201 to pAAT203 (Table 6). However, since there is no Sse8387I site in pET16b, that in which a linker including the Sse8387I cleavage sequence had been inserted at the BamHI site of pET16b was prepared in advance, and this was used as a vector.

The plasmids pAAT101 to pAAT103 were introduced to JM109 strain to obtain recombinant JM109/pAAT101 to pAAT103. The plasmids pAAT201 to pAAT203 were introduced to the BL21(DE3) strain to obtain recombinant BL21(DE3)/pAAT201 to pAAT203.

TABLE 6

| Plasmid for plant-derived AAT gene expression | | | |
|---|---|---|---|
| Plant origin | Template | Expression plasmid | |
| SEQ ID NO (gene name) | plasmid | pTrc99A | pET16b |
| 2  Apple (MpAAT1) | pAAT001 | pAAT101 | pAAT201 |
| 4  Strawberry (SAAT) | pAAT002 | pAAT102 | pAAT202 |
| 6  Strawberry (VAAT) | pAAT003 | pAAT103 | pAAT203 |

Example 7: Preparation of Cell-Free Extract from Recombinant E. coli Expressing AAT Gene (1) Culturing of Recombinant E. coli Using pTrc99A as Vector The Recombinant E. colis JM109/pAAT101 to pAAT103 obtained in Example 6 were inoculated into 1 ml of an LB culture medium containing 100 µg/ml of ampicillin, and preculturing was performed at 37° C. for 7 hours. The broth was taken in 0.1 ml, added to 100 ml of the same culture medium (100 µg/ml ampicillin, 1 m MIPTG contained), and shaking cultured at 37° C. for 15 hours. The bacterial cell was recovered by way of centrifugation (3,700×g, 10 min, 4° C.) from the obtained broth, and after washing with a 10 mM sodium phosphate buffer solution (pH 7.0), was suspended in the same buffer solution. JM109/pTrc99A was used as a reference strain.

(2) Culturing of Recombinant E. coli Using pET16b as Vector

The recombinant E. colis BL21(DE3)/pAAT201 to pAAT203 obtained in Example 6 were inoculated into 1 ml of an LB culture medium containing 100 µg/ml of ampicillin, and preculturing was performed at 37° C. for 14 hours. The broth was taken in 0.1 ml, added to 100 ml of the same culture medium (100 µg/ml ampicillin), and after shaking cultured at 37° C. until the OD became 0.3, IPTG was added so that the final concentration became 1 mM and was further shaking cultured for several hours. The bacterial cell was recovered by way of centrifugation (3,700×g, 10 min, 4° C.) from the obtained broth, and after washing with a 10 mM sodium phosphate buffer solution (pH 7.0), was suspended so as to be OD=6 (630 nm) in the same buffer solution. BL21(DE3)/pET16b was used as a reference strain.

(3) Preparation of Cell-Free Extract

Cell-free extract was prepared from the obtained bacterial cell suspension. Using an ultrasonic homogenizer VP-15S (Taitec, Japan), homogenizing was performed for 1 minute while keeping the bacterial cell suspension on ice at conditions of output control 4, DUTY CYCLE 40%, PULS, TIMER=B mode 10 s. Next, centrifugation was performed (10,000×g, 5 minutes, 4° C.), and 1 ml of the obtained supernatant (cell-free extract) was collected.

Example 8: Synthesis of Butyl Methacrylate Using AAT Gene Recombinant Cell-Free Extract The following reaction was performed using cell-free extract prepared by the method described in Example 7. The reaction was initiated by adding 0.2 ml of cell-free extract to a 10 ml-sample bottle with a septum (for GC) into which 0.8 ml of a solution of methacrylyl-CoA and alcohol was placed so that the final concentration of the reaction solution was 7 mM methacrylyl-CoA and 40.5 mM n-butanol. The sample bottle with a septum was incubated at 30° C. for 1 to 5 hours to cause reaction.

The gas in the head space of the sample bottle with a septum was analyzed similarly to Example 1. The results are shown in Table 7.

TABLE 7

Formation of butyl methacrylate using AAT gene recombinant

| Recombinant | Generated amount (mM) | | |
|---|---|---|---|
| | 1 hour | 3 hours | 5 hours |
| JM109/pAAT102 | 0.001 | 0.003 | 0.004 |
| JM109/pAAT103 | 0 | 0.001 | 0.002 |
| BL21(DE3)/pAAT201 | 0.003 | 0.014 | 0.026 |
| BL21(DE3)/pET6b | 0 | 0 | 0 |

Example 9A: Synthesis of Methacrylic Acid Ester Using AAT Gene Recombinant Cell-Free Extract The reaction was carried out similarly to Example 8 using methanol, ethanol or n-butanol as the alcohol, and using that derived from BL21(DE3)/pAAT201 (apple) in the cell-free extract. The analysis results of the product after 5 hours are shown in Table 8.

TABLE 8

Generation of methacrylic acid ester using AAT gene recombinant

| Recombinant | Generated amount after 5 hours (mM) | | |
|---|---|---|---|
| | Methyl methacrylate | Ethyl methacrylate | Butyl methacrylate |
| BL21(DE3)/pAAT201 | 0.021 | 0.045 | 0.091 |

Example 9B: Synthesis 2 of Methacrylic Acid Ester Using AAT Gene Recombinant Cell-Free Extract Using isobutanol, butanol, benzyl alcohol or 2-ethylhexyl alcohol, the following reaction was carried out with the cell-free extract of BL21(DE3)/pAAT201 (apple) obtained in Example 7.

The reaction was initiated by adding 0.2 ml of cell-free extract to a 10 ml-sample bottle with a septum (for GC) into which 0.8 ml of a solution containing methacrylyl-CoA and alcohol was placed so that the final concentration of the reaction solution was 1 mM methacrylyl-CoA and 40 mM n-butanol.

The sample bottle with a septum was incubated at 30° C. for 1 to 5 hours to cause reaction. After reaction completion, 1 mL of acetonitrile was added and mixed to the reaction solution in the sample bottle with a septum. Subsequently, after filtration using a syringe filter DISMIC/pore size 0.45 μm (manufactured by ADVANTEC), it was provided for HPLC analysis. The analysis results of the product after 5 hours are shown in Table 9.

Synthesis of Methacrylic Acid Esters (Isobutyl Methacrylate, Phenyl Methacrylate, Benzyl Methacrylate, 2-Ethylhexyl Methacrylate) Using AAT Gene Recombinant

TABLE 9

| Recombinant | Generated amount after 5 hours (mM) | | | |
|---|---|---|---|---|
| | Isobutyl methacrylate | Phenyl methacrylate | Benzyl methacrylate | 2-ethylhexyl methacrylate |
| BL21(DE3)/pAAT201 | 0.009 | 0.001 | 0.17 | 0.31 |

HPLC Analysis Conditions
  Device: Waters 2695
  Column: Shiseido CAPCELL PAK C18 UG120 5 μm
  Mobile phase: 65% MeOH, 0.2% phosphoric acid
  Flow rate: 0.25 ml/min
  Column temperature: 35° C.
  Detection: UV 210 nm
  Injection volume: 10 μL Example 10: Preparation of Recombinant *E. coli* Introduced with ACD Gene Preparation of High-Expression Recombinant with Cloning of ACD Homolog Gene from *Pseudomonas aeruginosa* PAO1
(1) Preparation of Genomic DNA from *Pseudomonas aeruginosa* PAO1

*Pseudomonas aeruginosa* PAO1 strain (NBRC106052) grown on LB nutrient agar (1% Bacto tryptone, 0.5% Bacto yeast extract, 0.5% NaCl, 1.5% agar) was inoculated to 10 ml of LB liquid culture medium (1% Bacto tryptone, 0.5% Bacto yeast extract, 0.5% NaCl), and shaking culturing was performed at 37° C. for 15 hours. After culturing completion, the bacterial cell was recovered by way of centrifuge from 2 ml of the broth, and 100 μl of genomic DNA was prepared using a Wizard Genomic DNA Purification Kit (Promega KK).

(2) Cloning of Expression Vector

The obtained genomic DNA was made a template, and a DNA fragment including a gene assumed to code ACD was prepared by way of the PCR method so as to be a form in which a restriction endonuclease recognition site enabling easy introduction to an expression vector was added.

Oligonucleotide Primer (SEQ ID NO. 13)
MMA-003: 5'-GACCCATGGATTTCGACCTCACCGAAGAAC-3'

(SEQ ID NO. 14)
MMA-004: 5'-GCCCTGCAGGATGCGATGGTTCGCGGCGTTC-3'

Reaction Solution Composition
  Sterilized water 22 μl
  2× PrimeSTAR (manufactured by Takara Bio) 25 μl
  MMA-003 (SEQ ID NO. 13) 1 μl
  MMA-004 (SEQ ID NO. 14) 1 μl
  Genomic DNA 1 μl
  Total amount 50 μl
Temperature Cycle
  30 cycles of reaction at 98° C. 10 seconds, 55° C. 15 seconds and 72° C. 150 seconds A band of about 1.2 kb of the obtained amplification product was purified by a QIAquick Gel Extraction Kit (QIAGEN). The purified DNA was digested with digested with restriction enzyme NcoI (cleavage recognition site included in oligonucleotide MMA-003) and Sse8387I (cleavage recognition site included in oligonucleotide MMA-004), and purified by way of phenol extraction/ chloroform extraction/ethanol precipitation. The purified DNA (5 μL), vector pTrc99A digested with NcoI and Sse8387I (1 μL), distilled water (4 μL) and solution I (DNA ligation Kit ver. 2 (Takara Bio)) (10 μL) were mixed, and the vector was ligated with PCR amplification product by incubating for 12 hours at 16° C.

To 200 μL of the competent cell prepared by the method of Reference Example 1, 10 μL of the above-mentioned ligation solution was added and left to stand at 0° C. for 30 minutes, followed by imparting heat shock at 42° C. for 30 seconds and cooling to 0° C. for 2 minutes, after which 1 mL of SOC culture medium (20 mM glucose, 2% Bacto tryptone, 0.5% Bacto yeast extract, 10 mM NaCl, 2.5 mM KCl, 1 mM $MgSO_4$, 1 mM $MgCl_2$) was added and shaking cultured at 37° C. for 1 hour.

After culturing, 200 μl of culture media was inoculated to LBAmp nutrient agar (LB culture medium containing 100 mg/L ampicillin, 1.5% agar), and further cultured at 37° C. A plurality of transgenic organism colonies cultured on nutrient agar was cultured overnight at 37° C. in 1.5 mL of LBAmp culture medium (LB culture medium containing 100 mg/L ampicillin), and after harvesting, plasmid DNA was recovered using a Flexi Prep (manufactured by Amersham Biosciences).

(3) Transformation

For the obtained recombinant plasmid DNA, the nucleotide sequence thereof was confirmed using a CEQ DTCS Quick Start Kit and fluorescent sequencer CEQ 2000XL DNA Analyzer (both Beckman Coulter, USA), and was named plasmid pMMA002. The *E. coli* JM109 strain was transformed using the plasmid pMMA002 to prepare a recombinant to which the ACD gene (SEQ ID NO. 8) had been introduced. The amino acid sequence is shown by SEQ ID NO. 7.

Example 11: Preparation of Cell-Free Extract from Recombinant *E. coli* Expressing ACD Gene Recombinant *E. coli* JM109/pMMA002 to which the ACD gene (SEQ ID NO. 8) obtained in Example 10 had been introduced was inoculated to 1 ml of an LB culture medium containing 100 μg/ml ampicillin, and preculturing was performed at 37° C. for 7 hours. The broth was taken in 0.1 ml, added to 100 ml of the same culture medium (100 μg/ml ampicillin, 1 m MIPTG contained), and shaking cultured at 37° C. for 15 hours. The bacterial cell was recovered by way of centrifugation (3,700×g, 10 min, 4° C.) from the obtained broth, and after washing with a 10 mM sodium phosphate buffer solution (pH 7.0), was suspended so as to be OD=6 (630 nm) in the same buffer solution. JM109/pTrc99A was used as a reference strain.

From the obtained bacterial cell suspension, 1 ml of cell-free extract was prepared as follows. Using an ultrasonic homogenizer VP-15S (Taitec, Japan), homogenizing was performed for 1 minute while keeping on ice at conditions of output control 4, DUTY CYCLE 40%, PULS TIMER=B mode 10 s. Next, centrifugation was performed (10,000×g, 5 minutes, 4° C.), and the obtained supernatant was collected as cell-free extract.

Example 12: Preparation of Butyl Methacrylate from Isobutyryl-CoA Using Plant Fragment and ACD Genetically Modified Recombinant Cell-Free Extract (1) Methacrylyl-CoA Synthesis Reaction with Isbutyryl-CoA as Substrate by ACD Genetically Modified Recombinant Cell-Free Extract To 1.84 ml of a solution containing 6 mM 1-methoxy-5-methyl phenazinium metilsulfate, 0.4 mM flavin adenine dinucleotide and 1 mM isobutyryl-CoA in a 100 mM sodium phosphate buffer solution (pH 8.0), 0.16 ml of cell-free extract having ACD activity obtained in Example 10 was added to prepare 2 ml of reaction solution. It was allowed to react at 37° C. for 30 minutes, and analysis was performed at the HPLC conditions shown below. As a result thereof, the peak of isobutyryl-CoA disappeared, thereby confirming the formation of methacrylyl-CoA.

HPLC Analysis Conditions

Column: Inertsil ODS-3V, 4.6 mm×250 mm
Mobile phase: 30% MeOH, 50 mM $H_3PO_4$, pH 5.7
Flow rate: 1.0 ml/min
Column temperature: 35° C.
Detection: UV 254 nm
Injection volume: 10 μl
Reaction solution diluted 10 times with mobile phase and measured.

(2) Synthesis of Butyl Methacrylate by Addition of n-Butyl Alcohol and Plant Fragment to Methacrylyl-CoA Synthesis Reaction Solution The skin of a banana was removed, the sarcrocarp was sliced with a cutter to a thickness of about 1 millimeter, and this was further divided into four. To a 50-ml flask, 1 g of the sliced banana, 0.9 ml of the methacrylyl-CoA synthesis reaction solution, 0.1 ml of 3.5 M KCl solution and 5 μl of n-butyl alcohol were added, sealed, and then allowed to react at 30° C. for 2 hours. Upon conducting analysis of methacrylic acid ester similarly to Example 1, 0.015 mM of butyl methacrylate formed.

Example 13: Preparation of Recombinant *E. coli* Introduced with ECH Gene (1) Preparation of Genomic DNA from *Rhodococcus* Bacterium

*Rhodococcus erythropolis* PR4 strain (NBRC100887) grown on LB nutrient agar culture medium was inoculated to 10 mL of LB liquid culture medium, and shaking culturing was performed at 30° C. for 36 hours. After culturing completion, the bacterial cell was recovered by way of centrifuge from 2 ml of the broth, and 100 μl of genomic DNA was acquired similarly to Example 10.

(2) Cloning of Expression Vector

The obtained genomic DNA was made a template, and a DNA fragment including a nucleotide sequence assumed to encode ECH gene was prepared by way of the PCR method so as to be a form in which a restriction endonuclease recognition site enabling easy introduction to an expression vector is added.

Oligonucleotide Primer:

```
                                              (SEQ ID NO. 15)
MMA-031: 5'-GGTCATGACCGACTTCAACACCATCATCCTC-3'

(SEQ ID NO. 16)
MMA-032: 5'-GGCCTGCAGGTTCAGCTGTTCGAAAGTTCAGCGC-3'
```

PCR was performed similarly to Example 10, and the obtained DNA was digested with restriction enzyme BspHI (cleavage recognition site included in oligonucleotide MMA-031) and Sse8387I (cleavage recognition site included in oligonucleotide MMA-032). After cleavage, the same operations as Example 6 were performed to acquire the target plasmid DNA to which ECH gene (SEQ ID NO. 10) was incorporated, and then named plasmid pMMA011. The amino acid sequence is shown by SEQ ID NO. 9.

(3) Transformation

*E. coli* JM109 strain was transformed using plasmid pMMA011 to prepare ECH gene expression Recombinant *E. coli*.

Example 14: Synthesis of Butyl Methacrylate from 3-Hydroxyisobutyryl-CoA Using ECH Gene Expression Recombinant *E. coli* Cell-Free Extract and AAT Gene Recombinant Cell-Free Extract (1) Preparation of Cell-Disrupted Liquid Having ECH Activity The Recombinant *E. coli* JM109/pMA011 to which the ECH gene obtained in Example 13 had been introduced was inoculated in an LB culture medium containing 2 ml of 100 μg/ml ampicillin, and preculturing was performed at 37° C. for 24 hours. The broth was taken in 0.1 ml, added to 100 ml of the same culture medium (100 μg/ml ampicillin, 1 m MIPTG contained), and shaking cultured at 37° C. for 15 hours. The bacterial cell was recovered by way of centrifugation (3,700×g, 10 min, 4° C.) from the obtained broth, and after washing twice with a 10 mM sodium phosphate buffer solution (pH 7.0), was diluted so as to be O=D6 (630 nm) in the same buffer solution.

From the obtained bacterial cell suspension, 1 ml of cell-disrupted liquid was prepared in the following way. Using an ultrasonic homogenizer Sonifier 250D (Branson, USA), it was homogenized for 5 minutes while keeping on ice at conditions of amplitude: 15%/On: 1 sec, off: 1 sec.

(2) Methacrylyl-CoA Synthesis Reaction Using ECH Gene Expression Recombinant *E. coli* Cell-Disrupted Liquid To the mixture prepared by mixing 0.2 ml of 0.5 M tris-HCl buffer solution (pH 7.4), 0.4 ml of 1.2 mM 3-hydroxyisobutyryl-CoA aqueous solution and 1.2 ml of water, 0.2 ml of cell-disrupted liquid having enoyl-CoA hydratase activity obtained in the above way was added to prepare 2 ml of reaction solution. It was allowed to react at 37° C. for 30 minutes, and analysis was performed at the HPLC conditions shown in Example 12. As a result thereof, the formation of methacrylyl-CoA was confirmed.

(3) Synthesis of Butyl Methacrylate Using AAT Gene Recombinant Cell-Free Extract To a 10-ml sample bottle, 0.4 ml of the methacrylyl-CoA synthesis reaction solution, 0.1 ml of 10 mM sodium phosphate buffer solution (pH 7.5) and 0.2 ml of water were added, 0.1 ml of 0.4 M n-butanol solution and 0.2 ml of apple AAT (MpAAT) cell-disrupted liquid prepared similarly to Example 7 were further added, sealed, and then allowed to react at 30° C. for 3 hours. Upon conducting analysis of methacrylic acid ester similarly to Example 1, 0.001 mM of Butyl methacrylate formed.

Example 15: Preparation of High-Expression Recombinant with Cloning of BCKAD Gene, Preparation of Cell-Free Extract, and Protein Expression Analysis The preparation of expression plasmid with gene cloning and preparation of recombinant were performed similarly to Example 10. Genomic DNA of *Pseudomonas aeruginosa* PAO1 strain was made a template, and a DNA fragment including the entire gene operon coding BCKAD complex gene was prepared by way of the PCR method using the primer shown below. The obtained fragment was digested by restriction enzyme BspHI and Sse8387I, and inserted into vector pTrc99A similarly to Example 10 to obtain the recombinant plasmid (pWA108).

Oligonucleotide Primers:

```
                                    (SEQ ID NO. 17)
MAA-15: 5'-GGCCTGTCATGAGTGATTACGAGCCG-3'

(SEQ ID NO. 18)
MAA-16: 5'-CGGCCCTGCAGGTTCGCGGGAATCAGATGTGC-3'
```

The Recombinant *E. coli* JM109/pWA108 obtained in the above way was cultured similarly to Example 10. However, in the case of the present recombinant, since high expression of protein was recognized even without performing addition of IPTG based on the preliminary results, it was conducted without the addition of IPTG. The preparation of cell-free extract was conducted similarly to Example 11.

Example 16: Activity Measurement of Cell-Free Extract of BCKAD Gene High-Expression Recombinant The BCKAD activity was measured from the generation of isobutyryl-CoA with 2-oxoisovaleric acid as the substrate in the following way.

To 0.7 ml of a solution containing final concentrations of 1 mM $MgCl_2$, 0.2 mM thiamin pyrophosphate, 1 mM CoA-Sh and 2 mM DDT in a 100 mM sodium phosphate buffer solution (pH 7.0), 0.2 ml of the cell-free extract obtained in Example 15 was added to make up 0.9 mL. After adding 0.1 mL (4 mM final concentration) of 2-oxoisovaleric acid calcium salt to this and reacting at 37° C. for 30 minutes, ultrafiltration was performed using a Centricut Super Mini W-10 (Kurabo Industries Ltd.). The reaction was stopped by performing deproteinization, and analysis was performed by HPLC at the following conditions. As a result thereof, the formation of 0.83 mM isobutyryl-CoA was recognized with JM109/pWA108.

HPLC Analysis Conditions

Column: Inertsil ODS-3V, 4.6 mm×250 mm
Mobile phase: 35 MeOH, 50 mM $H_3PO_4$, pH 5.7
Flow rate: 1.0 ml/min
Column temperature: 35° C.
Detection: UV254 nm (210 nm)
Injection volume: 10 μl (reaction solution diluted 10 times with mobile phase and measured)

Example 17: Synthesis of Methacrylyl-CoA (FIG. 1) from 2-Oxoisovaleric Acid by Cell-Free Extract Mixture from BCKAD Gene High-Expression Recombinant and Recombinant Expressing ACD Gene To 0.6 ml of a solution containing final concentrations of 1 mM $MgCl_2$, 0.2 mM thiamin pyrophosphate, 1 mM CoA-SH, 2 mM DDT, 2 mM nicotinamide adenine dinucleotide (NAD), 0.04 mM flavin adenine dinucleotide (FAD) and 2 mM valine in a 100 mM sodium phosphate buffer solution (pH 7.0), 0.1 ml of each of the cell-free extracts (JM109/pMMA002 and JM109/pWA108) obtained by the methods of Example 11 and Example 15 was respectively added to make up 0.8 mL. After adding 0.1 mL of 2-oxoisovaleric acid calcium salt (4 mM final concentration) to this and reacting at 37° C. for 30 minutes, the formation of isobutyryl-CoA was confirmed by HPLC, and 0.1 mL of 1-methoxy-5-methyl phenazinium metilsulfate (6 mM final concentration) was added and allowed to further react for 3 hours. After reaction, ultrafiltration was performed using a Centricut Super Mini W-10 (Kurabo Industries Ltd.). The reaction was stopped by performing deproteinization, and analysis was performed by HPLC. As a result thereof, the formation of 0.2 mM methacrylyl-CoA was recognized.

Reference Example 2: Preparation of Conjugational Transfer Recipient PR4KS

*Rhodococcus erthropolis* PR4 (NITE Biological Resource Center; deposit number: NBRC 100887) was modified by the method described in Japanese Unexamined Patent Application, Publication No. 2011-200133 to prepare a derivative exhibiting resistance to 120 mg/L chloramphenicol and lacking kanamycin-resistant gene, and was named as PR4KS strain.

More specifically, in order to enhance chloramphenicol resistance, the concentration of chloramphenicol in an MYK culture medium (0.5% polypeptone, 0.3% bact-yeast extract, 0.3% malt extract, 0.2% $KH_2PO_4$, 0.2% $K_2HPO_4$) was gradually raised step-wise starting from 10 mg/mL until 120 mg/mL, while inducing spontaneous mutation by subculturing PR4 strain, thereby obtaining derivative RhCmSR-09 strain having resistance to 120 mg/mL of chloramphenicol.

Next, the above-mentioned RhCmSR-09 strain was mixed at a 1:1 ratio with *E. coli* retaining the plasmid pKM043 for the kanamycin-resistant gene deficiency variation introduction described in Japanese Unexamined Patent Application, Publication No. 2011-200133, then cultured, and after introducing pKM043 into the RhCmSR-09 strain by conjugational transfer, was cultured in MYK nutrient agar containing 200 mg/L kanamycin sulfate and 50 mg/L chloramphenicol (0.5% polypeptone, 0.3% bact yeast extract, 0.3% malt extract, 0.2% $KH_2PO_4$, 0.2% $K_2HPO_4$, 1.5% agar), thereby obtaining a homologous recombinant strain in which pKM043 had been introduced into the RhCmSR-09 strain genome. The homologous recombinant strain was cultured in 10% sucrose-containing MYK nutrient agar, whereby a derivative strain emerging as a kanamycin-sensitive strain from among the obtained colonies, i.e. kanamycin-resistant gene deficiency variation derivative strain PR4KS, was obtained.

Reference Example 3: Preparation of Plasmid for Gene Deficiency with Cloning of LigD Homolog Gene The LigD homolog gene (accession No: YP_002767969) of the PR4KS strain was established as the target gene. After amplification of about 5.4 kb of DNA including the LigD homolog gene surrounding sequence by way of PCR, it was cloned to plasmid vector pK19mobsacB1 to which the sacB gene had been introduced downstream and in the same orientation of the kanamycin-resistant gene, described in Japanese Unexamined Patent Application, Publication No. 2011-200133, thereby obtaining plasmid pTJ001. The PCR conditions were as follows.
Primers (SEQ ID NO. 19)
GB-138: 5'-GGCCTGCAGGTACCGATCATCACCATCGGTGTC-3'

(SEQ ID NO. 20)
GB-139: 5'-GGTCTAGACTGAGCAGTGTTCCAATGCG-3'

Figure 3:
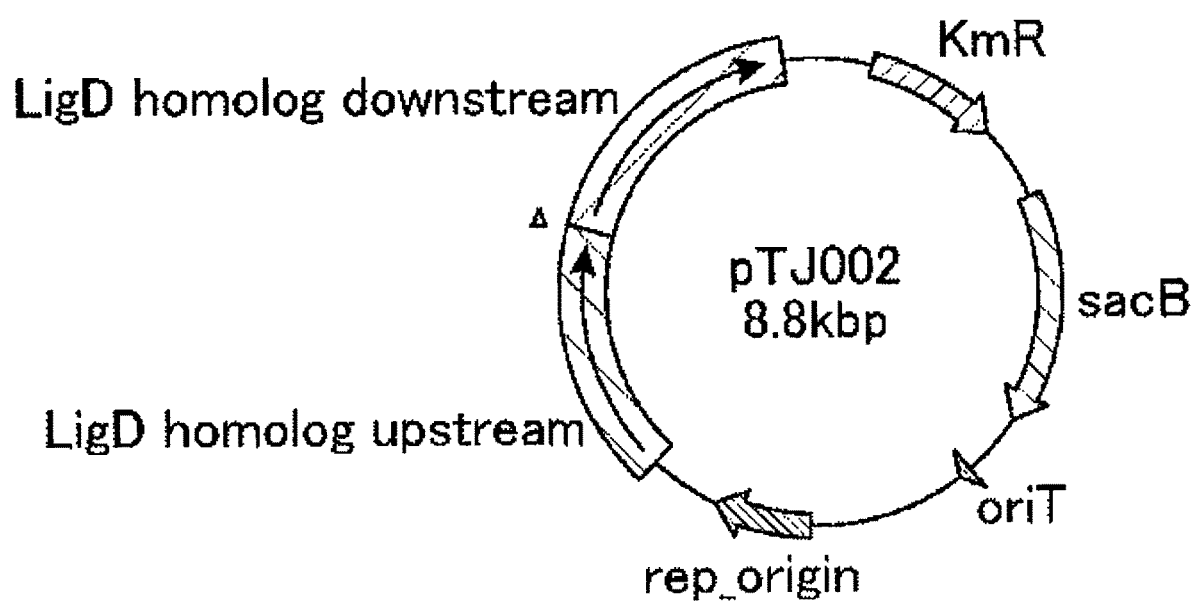
FIG. 3 is a view showing the structure of a plasmid for LigD homolog gene deletion.

Reaction Solution Composition
Sterilized water 22 µl
2× PrimeSTAR (manufactured by Takara Bio) 25 µl
GB-138 (SEQ ID NO. 19) 1 µl
GB-139 (SEQ ID NO. 20) 1 µl
PR4KS genome (50 ng/µL) 1 µl
Total amount 50 µl
Temperature Cycle
35 cycles of reaction at 98° C. 10 seconds, 55° C. 15 seconds and 72° C. 120 seconds The plasmid for LigD homolog gene deficiency pTJ002 was prepared in which the entire length of the LigD homolog sequence inside pTJ001 (about 2.3 kb) was deleted and only the upstream and downstream sequences of the LigD homolog gene were allowed to remain (refer to FIG. 3). The sequence within pTJ001 was amplified using primers GB-140 and GB-141, which include the surrounding sequence of the start codon and the surrounding sequence of the stop codon of the targeted LigD homolog gene, respectively, and which were designed so as to extend in the upstream direction from the start codon and in the downstream direction of the stop codon, respectively, in order to obtain PCR product that does not include the LigD homolog gene. *E. coli* JM109 strain was transformed by the obtained PCR product to make circular DNA as pTJ002. The PCR conditions are as follows.
Primers (SEQ ID NO. 21)
GB-140: GAGGAAATGGTCACAGGGCGAGAATAGGTTG (SEQ ID NO. 22)
GB-141: GCCCTGTGACCATTTCCTCATTGTGCTGG Reaction Solution Composition
Sterilized water 22 µl
2× PrimeSTAR (manufactured by Takara Bio) 25 µl
GB-140 (SEQ ID NO. 21) 1 µl
GB-141 (SEQ ID NO. 22) 1 µl
pTJ001 1 µl
Total amount 50 µl
Temperature Cycle
30 cycles of reaction at 98° C. 10 seconds, 50° C. 10 seconds and 72° C. 180 seconds After PCR completion, upon performing confirmation of the fragment by 0.7% agarose gel electrophoresis using 1 µl of sample, amplification of the fragment was recognized. In the above-mentioned plasmid pTJ002 production procedure, a Wizard Genomic DNA Purification Kit (manufactured by Promega) was used in the genome extraction from PR4 strain, a Gel/PCR Purification Kit (manufactured by FAVORGEN) was used in the purification of DNA fragment digested with the restriction enzyme and the PCR product, a DNA Ligation Kit <Mighty Mix> (manufactured by Takara Bio) was used in the joining of DNA, and a QIAprep miniprep kit (manufactured by QIAGEN) was used in the extraction of plasmid.

Reference Example 4: Preparation of LigD Homolog Gene Deficient Derivative Strain of PR4KS With the product by transforming *E. coli* (*Escherichia coli*) S17-1λpir by way of pTJ002 as the donor, and the PR4KS obtained by the method of Reference Example 2 as the recipient, conjugal transfer was performed similarly to the method described in Japanese Unexamined Patent Application, Publication No. 2011-200133 to obtain 13 strains of the LigD homolog gene deficient derivative strain produced by homologous recombination. One strain was selected from the deficient derivative strains, and named PR4KSΔligD.

Reference Example 5: Preparation of Plasmid pLK005 for *Rhodococcus* Bacterium and Nitrile Hydratase Expression Plasmid pSJ201 Using this (1) Acquisition and Analysis of pLK005

Using pK4 (refer to Japanese Unexamined Patent Application, Publication No. H5-64589), *Rhodococcus* sp N775 (National Institute of Advanced Industrial Science and Technology, Patent Organism Depository, deposit number FERM BP-961) was transformed by the above-mentioned electroporation method. The obtained transformant was inoculated to 10 ml of MYK culture medium, and cultured at 30° C. for 1 day. Variation treatment was performed by exposing this to ultraviolet light inside a clean bench. The culture liquid in which variation treatment was performed was applied to MYK nutrient agar containing 50 to 400 μg/ml kanamycin, and cultured at 30° C. for 3 days.

The plurality of colonies appearing on the nutrient agar was respectively cultured in MYK culture medium, and plasmids were recovered from the transformants. Using the recovered plasmid, *Rhodococcus* sp N775 was transformed again, and it was investigated whether the kanamycin resistance of the transformant improves. As a result thereof, a number of strains of transformant for which the kanamycin resistance clearly improved were recognized.

Upon investigating the nucleotide sequences of plasmids for which kanamycin resistance was recognized as improving, it was recognized that a change occurs in the sequence in the upstream region of the kanamycin-resistant gene of pK4 (overlap of 8-nucleotide sequence GTTGTAGG). This plasmid for which this kanamycin resistance was recognized as improving was named pLK005.

(2) Preparation of pSJ040

The plasmid pSJ034 is a plasmid prepared from the plasmid pSJ023 by the method described in Japanese Unexamined Patent Application, Publication No. H10-337185. In pSJ034, although three EcoRI restriction enzymes sites are present, the plasmid pSJ040 was prepared in which one of these was transformed to a SpeI site. Specifically, pSJ034 was partially decomposed using restriction enzyme EcoRI. The cleavaged site was converted into blunt end using Takara Blunting kit and then ligation reaction was performed under the presence of SpeI linker. *E. coli* JM109 strain was transformed using the reaction solution. After culturing the transformant, plasmid was extracted, and the plasmid to which SpeI linker had been inserted was separated. Plasmid in which SpeI linker was inserted at, among the three EcoRI sites of pSJ034, the EcoRI site present downstream of the kanamycin-resistant gene was named pSJ040.

(3) Assembly of pSJ201 pLK005 was digested with HindIII to prepare a fragment of about 2.1 kb. On the other hand, pSJ040 was digested with HindIII to prepare a fragment of about 9.8 kb. Using these two fragments, the ligation reaction was performed, and *E. coli* JM109 strain was transformed using the reaction solution. After culturing the transformant, the plasmid was extracted and the nucleotide sequence thereof was confirmed, a result of which a plasmid keeping the mutated sequence (duplication of GTTGTAGG) derived from pLK005, and otherwise having the same sequence as pSJ040 was named pSJ201.

Figure 4:
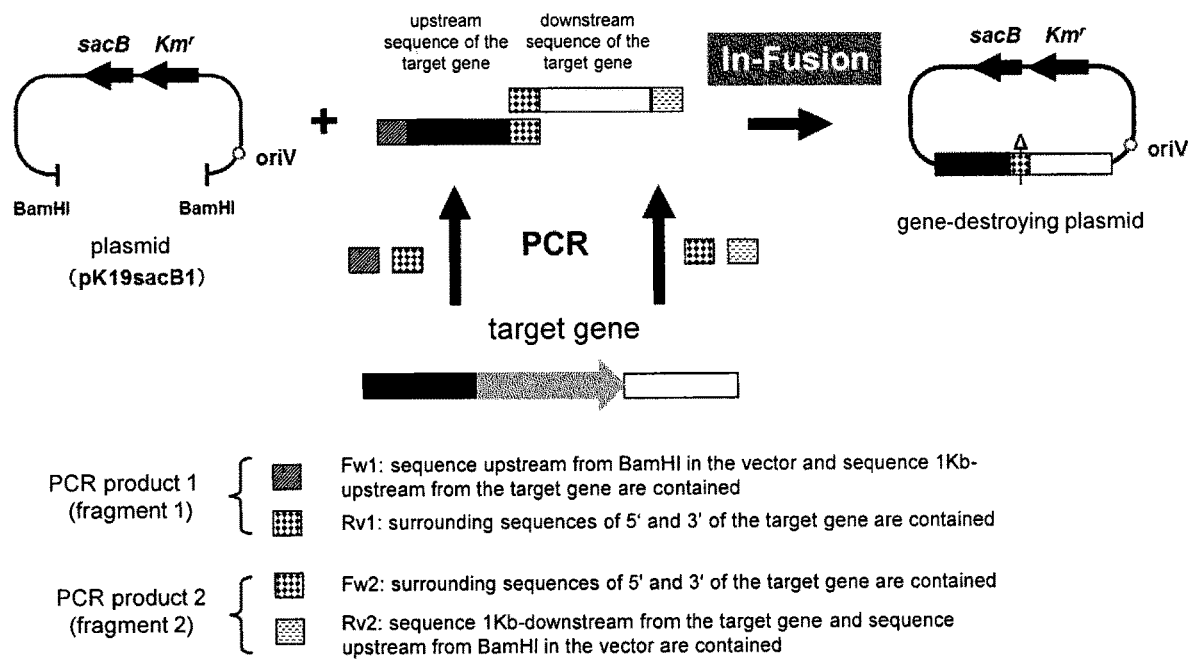
FIG. 4 is a view illustrating a preparation method for plasmid for gene deletion using the In Fusion method.

Reference Example 6: Preparation of RE_Acd1/RE_echA/RE_hchA/RE_mmsB Gene Deficient Derivative Strain of PR4KSΔligD Derivative Strain (1) Preparation of Plasmid for Gene Deficiency Using in Fusion Method The preparation of a plasmid for gene deficiency was performed by way of an In-Fusion HD Cloning kit (manufactured by Takara Bio) in which the RE_acd1/RE_echA/RE_hchA/RE_mmsB gene of PR4KS strain was the target gene (refer to FIG. 4).

The DNA of the upstream and downstream sequences of the target gene was amplified by PCR. The PCR conditions were as follows.

Primers for Fragment 1

```
                                    (SEQ ID NO. 23)
MMA-061: CGACTCTAGAGGATCGCTCAGTACATCTACGAGAC (SEQ ID NO. 24)
MMA-062: AGTGTGAGGAAAGTGTTCCGATCAGTTCAT
```

Primers for Fragment 2

```
                                    (SEQ ID NO. 25)
MMA-063: CACTTTCCTCACACTCGTCGAGAGTATGAG (SEQ ID NO. 26)
MMA-064: CGGTACCCGGGGATCAGCGCGACGAACAACGAGAC
```

Reaction Solution Composition
  Template (PR4 wild type genomic DNA) 1 μL
  2× PrimeSTAR Max Premix (manufactured by Takara Bio) 25 μL
  Fw primer (20 μM) 1 μL
  Rv primer (20 μM) 1 μL
  D. W. 22 μL
  Total amount 50 μl
Temperature Cycle
  30 cycles of reaction at 98° C. 10 seconds, 60° C. 10 seconds and 72° C. 120 seconds After PCR completion, upon performing confirmation of the fragment by 0.7% agarose gel electrophoresis using 1 μl of sample, amplification of the fragment was recognized. Using a Gel/PCR Purification Kit (manufactured by FAVORGEN), buffer substitution was performed on the PCR product (fragment 1 and fragment 2), and used in the reaction by the In-Fusion HD Cloning Kit shown below.

(2) Linkage of Target Fragment with Vector by in-Fusion HD Cloning Kit and Transformation The linkage of the above-mentioned fragment and vector was performed using the In-Fusion HD Cloning Kit. The reaction conditions were as follows.

Reaction Solution Composition
  5× In-Fusion HD Enzyme Premix 2 μL
  Vector fragment 1.5 μL
  DNA fragment 1 1 μL
  DNA fragment 2 2 μL
  D. W. 3.5 μL
  Total amount 10 μL After incubating the above-mentioned reaction solution at 50° C. for 15 minutes, it was cooled on ice, and used in the transformation of *E. coli* JM109 strain. The selection of *E. coli* transformant was performed with LB nutrient agar containing 50 mg/L kanamycin sulfate (hereinafter, LB Km 50 nutrient agar). Plasmid was prepared from the obtained transformant using a Mini prep Kit (QIAGEN) to obtain the target plasmid. Confirmation of the plasmid was performed by investigating the fragment size after XbaI restriction enzyme treatment, and the sequence of the linkage region of the insert fragment and vector. The target plasmid was named pMMA302.

(3) Preparation of Homologous Recombinant Derivative Strain of PR4KSΔligD Derivative Strain and Gene Deficient Derivative Strain To 20 µl of PR4KSΔligD strain competent cell, 1 µl of pMMA302 was added, and incubated on ice for 10 minutes. The entire amount of the above-mentioned incubated solution was moved to an ice-cooled electroporation cuvet (0.1 cm), high voltage of 1.5 kV (200Ω) was applied, 600 µl of LB liquid culture medium was immediately added, and left to stand at 30° C. for 6 hours. On the LB nutrient agar containing 10 mg/L kanamycin sulfate (hereinafter, LB Km10 nutrient agar), 200 µl was spread and cultured at 30° C. for 4 days. The grown colony was streaked on the LB Km10 nutrient agar, and after culturing for 4 days, colony PCR was performed according to the conditions shown below and confirmation of the homologous recombinant derivative strain was performed.

Primers

```
                                        (SEQ ID NO. 27)
    MMA-069:  GCGCATCTACAAGGAAGAGATC (SEQ ID NO. 28)
    MMA-070:  GCGACGCTCATCGAGATCTC
```

Reaction Solution Composition
Template 4.0 µl
2× Mighty Amp Buffer (manufactured by Takara) 5.0 µl
Fw Primer (20 µm) 0.25 µl
Rv Primer (20 µm) 0.25 µl
D. W. 0.3 µl
Mighty Amp DNA Polymerase (manufactured by Takara) 0.2 µl
Total 10.0 µl Temperature Cycle
30 cycles of reaction at 98° C. 10 seconds, and 68° C. 180 seconds The colony recognized as being a homologous recombinant derivative strain was suspended in 200 µl of LB culture medium, 100 µl was spreadon LB+10% sucrose nutrient agar, and cultured for 3 days. From the grown colonies, those that came to be kanamycin sensitive were selected, and the target gene deficiency was confirmed for these by colony PCR. As a result thereof, a strain in which the four genes of RE_acd1, RE_echA, RE_hchA and RE_mmsB had been deleted from the PR4KSΔligD derivative strain was obtained, and named DMA008 strain.

Example 18: Preparation of Plasmid for ACD and AAT Co-Expression in Microorganism Belonging to *Rhodococcus* Genus Plasmid for expressing ACD and/or AAT in microorganisms belonging to *Rhodococcus* genus was prepared.

A "nitrilase promoter+MpAAT1 gene" fragment obtained by PCR reaction with plasmid pAAT301 for MpAAT1 gene expression as the template was inserted downstream of the RE_acd1 gene of plasmid pMMA401 for RE_acd1 gene expression.

Amplification of the "nitrilase promoter+MpAAT1 gene" fragment was performed as follows.

Primers

```
MMA-133(Sse-ProFw):
                                        (SEQ ID NO. 29)
TGACCTGCAGGTGCACTCCGCTGCGACATGTATCGA

MMA-131(Sse-001Rv):
                                        (SEQ ID NO. 30)
ACTCTAGCCTGCAGGTCATTGACTAGTTGATCTAAGGTTGTTACA
```

PCR Reaction Composition
Template (pAAT301) 1 µl
2× PrimeSTAR Max Premix (manufactured by Takara) 10 µl
Fw Primer (10 µM) 0.6 µl
Rv Primer (10 µM) 0.6 µl
D. W. 7.8 µl
Total 20 µl Temperature Cycle
30 cycles of reaction at 98° C. 5 seconds, 60° C. 5 seconds and 72° C. 45 seconds The "nitrilase promoter+MpAAT1 gene" fragment obtained in this way was treated with restriction enzyme Sse8387I. On the other hand, after treatment with Sse8387I, SAP treatment was performed also on pMMA401. These DNA fragments were purified using a Gel/PCR Purification Kit (manufactured by FAVORGEN) after performing 0.7% agarose gel electrophoresis. The restriction enzyme treatment reaction conditions and ligation reaction conditions were as follows.

Restriction Enzyme Treatment Reaction Composition (AAT Fragment)
PCR amplified fragment 40 µl
10×M buffer 5 µl
0.1% BSA 4 µl
Sse8387I (manufactured by Takara) 1 µl
Total 50 µl Restriction Enzyme Treatment Reaction Composition (Vector Fragment)
pMMA401 (vector) 3 µl
10×M buffer 4 µl
0.1% BSA 4 µl
AP 1 µl
Sse8387I (manufactured by Promega) 1 µl
D. W. 27 µl
Total 40 µl Ligation Reaction Composition
pMMA401 1 µl
Insert fragment 2 µl
Ligation Mix (manufactured by Takara) 3 µl
Total 6 µl Transformation of *E. coli* JM109 strain was performed using a ligation reaction solution mixed in the above-mentioned composition. Plasmid was extracted from the obtained transformant. After restriction enzyme Sse8387I treatment, agarose electrophoresis was performed, and it was confirmed that a fragment of the target size is being inserted. It was confirmed as being the target plasmid from the nucleotide sequence analysis of the linkage region of the insert fragment of the obtained plasmid, and the present plasmid was named pACDAAT1.

Figure 5:
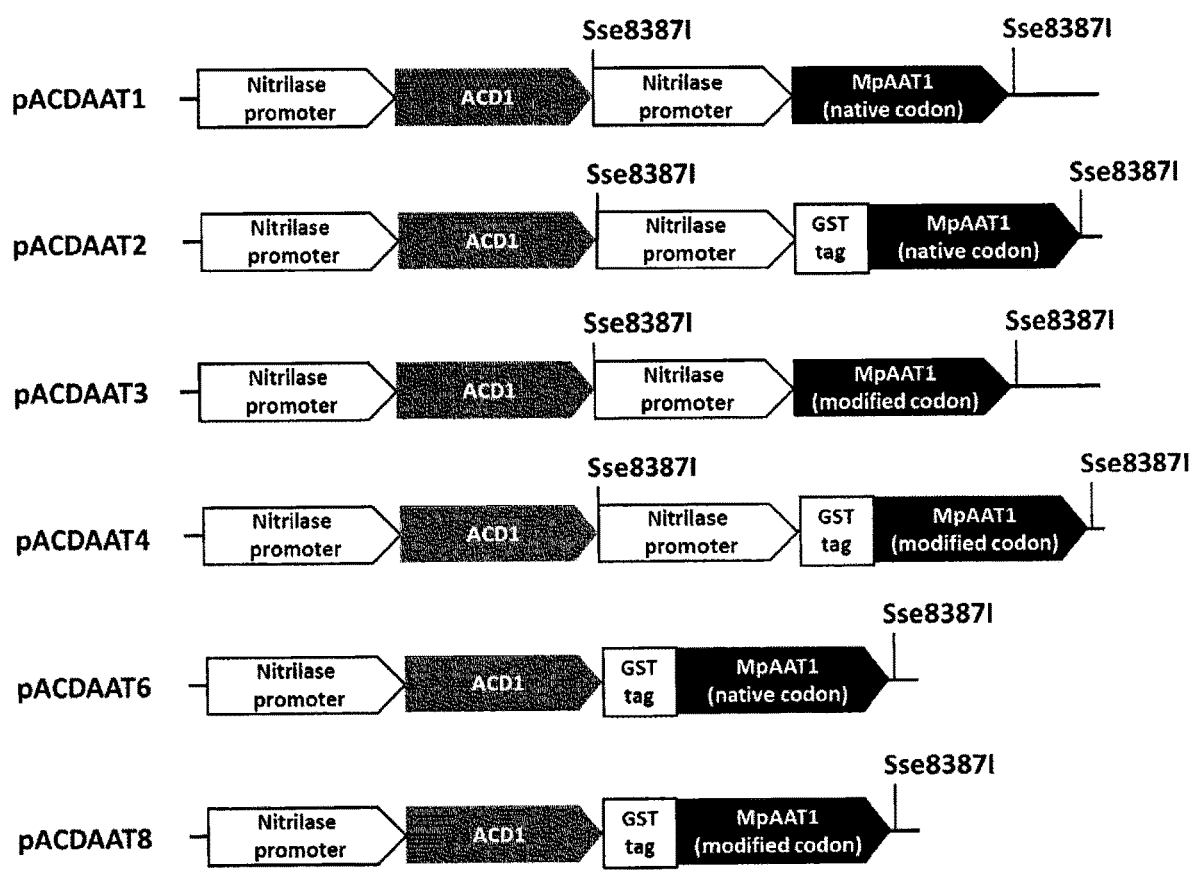
FIG. 5 is a view showing the structures of plasmids for ACD-AAT co-expression.

A total of six plasmids for ACD and AAT co-expression of different sequences (pACDAAT2, pACDAAT3, pACDAAT4, pACDAAT6 and pACDAAT8) were prepared using the same technique as the above-mentioned technique (refer to FIG. 5).

Example 19: Production of Butyl Methacrylate from ACD and AAT Co-Expressing Recombinant DMA008 strain obtained in (3) of Reference Example 6 was transformed by plasmids pACDAAT1, pACDAAT2, pACDAAT3, pACDAAT4, pACDAAT6 and pACDAAT8, respectively. Using the obtained recombinants (DMA008/pACDAAT1, DMA008/pACDAAT2, DMA008/pACDAAT3, DMA008/pACDAAT4, DMA008/pACDAAT6 and DMA008/pACDAAT8), the production of methacrylic acid ester was performed by the resting microorganism reaction. In addition, DMA008/pLK005 was used as a control.

To 2 ml of LB Km 10 liquid culture medium (Wassermann test tube), 1 inoculating loop was inoculated, and was cultured for 2 days at 30° C. with a rotary shaker (180 rpm) under aerobic conditions (preculture). To 100 mL of LB Km 10 (culture medium 100 mL/500 mL three-neck flask), 1 ml of prebroth was inoculated, and culturing was performed for 3 days at 30° C. in a rotary shaker (230 rpm) under aerobic conditions (main culture).

After main culturing, 40 mL of the main broth was transferred to a 50 mL conical tube, and centrifuged (12,000 rpm, 10 min), to obtain the bacterial cell. Using this bacterial cell, the below reaction was performed. To a 10-ml glass sample bottle, 1 ml of reaction solution was added to carry out reaction for 18 hours at 30° C. in a rotary shaker (180 rpm) under aerobic conditions.

Reaction Solution Composition
OD630=10 bacterial cell (final concentration)
5.0 g/l 2-oxoisovaleric acid (final concentration)
40 mM alcohol (final concentration)
50 mM sodium phosphate buffer/pH 7.5 (final concentration)
n-butanol was used as the alcohol.

After reaction, 1 mL of acetonitrile was added to the reaction solution and well mixed, followed by filtering using a syringe filter DISMIC/pore size 0.45 μm (manufactured by ADVANTEC), and then analyzed with the HPLC analysis described in Example 9B. The analysis results of the product after 18 hours are shown in Table 10.

Formation of Butyl Methacrylate from ACD and AAT Co-Expressing Recombinant

TABLE 10

| Recombinant | Generated amount of butyl methacrylate (μM) |
| --- | --- |
| DMA008/pLK005 | 0 |
| DMA008/pACDAAT1 | 7.51 |
| DMA008/pACDAAT2 | 2.06 |
| DMA008/pACDAAT3 | 4.34 |
| DMA008/pACDAAT4 | 0.46 |
| DMA008/pACDAAT6 | 2.18 |
| DMA008/pACDAAT8 | 0.52 |

Example 20: Production of Methacrylic Acid Ester from ACD and AAT Co-Expressing Recombinant The DMA008 strain obtained in (3) of Reference Example 6 was transformed by plasmid pACDAAT1, respectively. Using the obtained recombinant (DMA008/pACDAAT1), the production of methacrylic acid ester was performed by the resting microorganism reaction. In addition, DMA008/pLK005 was used as a control. Using the method described in Example 19, culturing of recombinant was carried out to obtain the bacterial cell.

Reaction Solution Composition
OD630=10 bacterial cell (final concentration)
5.0 g/l 2-oxoisovaleric acid (final concentration)
40 mM alcohol (final concentration)
50 mM sodium phosphate buffer/pH 7.5 (final concentration)
n-butanol, isobutanol and 2-ethylhexyl alcohol were used as the alcohol.

After reaction, 1 mL of acetonitrile was added to the reaction solution and well mixed, followed by filtering using a syringe filter DISMIC/pore size 0.45 μm (manufactured by ADVANTEC), and then analyzed with the HPLC analysis described in Example 9B. The analysis results of the product after 18 hours are shown in Table 11.

Formation of Methacrylic Acid Ester from ACD and AAT Co-Expressing Recombinant

TABLE 11

| | Generated amount (mM) | | |
| --- | --- | --- | --- |
| Recombinant | Butyl methacrylate | Isobutyl methacrylate | 2-ethylhexyl methacrylate |
| DMA008/pLK005 | 0 | 0 | 0 |
| DMA008/pACDAAT1 | 0.01 | 0.006 | 0.02 |

Comparative Example 1

Synthesis Reaction of Methacrylic Acid Ester from Yeast-Derived AAT Gene Recombinant Cell-Free Extract Yeast-derived AAT gene expressing plasmids were prepared similarly to Example 6 (Table 12), and E. coli was transformed using these to obtain AAT expressing recombinant.

Yeast-Derived AAT Gene Expression Plasmid

TABLE 12

| | | | Expression plasmid | |
| --- | --- | --- | --- | --- |
| SEQ ID NO | Gene name | Template plasmid | pTrc99A | pET16b |
| 34 | ATF1 | pAAT005 | pAAT105 | pAAT205 |
| 36 | ATF2 | pAAT006 | pAAT106 | pAAT206 |

Cell-free extract was prepared similarly to Example 7, and the synthesis reaction of butyl methacrylate was performed with methacrylyl-CoA and n-butanol as substrate similarly to Example 8. As a result thereof, the formation of butyl methacrylate was not recognized. On the other hand, in the case of establishing acetyl-CoA and n-butanol as substrate, the formation of butyl acetate was recognized.

Formation of Ester Using Yeast-Derived AAT Gene Recombinant

TABLE 13

| | Generated amount (mM) | | | | | |
| --- | --- | --- | --- | --- | --- | --- |
| | Butyl methacrylate | | | Butyl acetate | | |
| Recombinant | 1 hour | 3 hours | 5 hours | 30 min | 1 hour | 3 hours |
| JM109/pAAT105 | 0 | 0 | 0 | 0.089 | 0.145 | 0.170 |
| JM109/pAAT106 | 0 | 0 | 0 | 0.104 | 0.189 | 0.290 |
| JM109/pTrc99A | 0 | 0 | 0 | 0 | 0 | 0 |

SEQ ID NO. 11: MMA-044
SEQ ID NO. 12: MMA-045
SEQ ID NO. 13: MMA-003
SEQ ID NO. 14: MMA-004
SEQ ID NO. 15: MMA-031
SEQ ID NO. 16: MMA-032
SEQ ID NO. 17: MAA-15
SEQ ID NO. 18: MAA-16
SEQ ID NO. 19: GB-138
SEQ ID NO. 20: GB-139

SEQ ID NO. 21: GB-140
SEQ ID NO. 22: GB-141
SEQ ID NO. 23: MMA-061
SEQ ID NO. 24: MMA-062
SEQ ID NO. 25: MMA-063
SEQ ID NO. 26: MMA-064
SEQ ID NO. 27: MMA-069
SEQ ID NO. 28: MMA-070
SEQ ID NO. 29: MMA-133
SEQ ID NO. 30: MMA-131

The invention claimed is:

1. A method for producing methacrylic acid ester, the method comprising:
   transforming isobutyryl-CoA or 3-hydroxyisobutyryl-CoA to form methacrylyl-CoA, and
   contacting methacrylyl-CoA with an alcohol or a phenol in the presence of an alcohol acyltransferase, wherein the methacrylic acid ester accumulated has a concentration of at least 0.001 mM, and wherein the alcohol acyltransferase is of plant origin and wherein the plant belongs to a genus of *Malus*.

2. The method for producing a methacrylic acid ester according to claim 1, comprising transforming isobutyryl-CoA to form the methacrylyl-CoA, wherein the isobutyryl-CoA is produced from 2-oxoisovaleric acid.

3. The method for producing a methacrylic acid ester according to claim 1, wherein said alcohol or phenol is a linear or branched C1-10 unsubstituted alcohol, aralkyl alcohol or phenol.

4. The method for producing a methacrylic acid ester according to claim 3, wherein the methacrylic acid ester accumulated has a concentration of at least 0.010 mM.

5. The method for producing a methacrylic acid ester according to claim 1, wherein the methacrylic acid ester accumulated has a concentration of at least 0.010 mM.

6. The method for producing a methacrylic acid ester according to claim 1, wherein said alcohol or phenol is selected from the group consisting of methanol, ethanol, n-propanol, isopropanol, n-butanol, isobutanol, sec-butanol, tert-butanol, n-pentylalcohol, isopentyl alcohol, tert-pentyl alcohol, n-hexyl alcohol, isohexyl alcohol, 2-hexyl alcohol, dimethylbutyl alcohol, ethylbutyl alcohol, heptyl alcohol, octyl alcohol, 2-ethylhexyl alcohol, benzyl alcohol and phenol.

7. The method for producing a methacrylic acid ester according to claim 1, wherein the methacrylic acid ester accumulated has a concentration of at least 0.010 mM.

8. The method for producing methacrylic acid ester according to claim 1, wherein the alcohol acyltransferase is expressed by a genetically modified microorganism that has been transformed to express the alcohol acyltransferase.

9. The method for producing methacrylic acid ester according to claim 8, wherein the genetically modified microorganism belongs to the *Rhodococcus* genus.

10. A method for producing a methacrylic acid ester, the method comprising:
    transforming isobutyryl-CoA or 3-hydroxyisobutyryl-CoA to form methacrylyl-CoA, and
    contacting methacrylyl-CoA with an alcohol or a phenol in the presence of an alcohol acyltransferase, wherein the methacrylic acid ester accumulated has a concentration of at least 0.001 mM, and wherein the alcohol acyltransferase is of plant origin and wherein said plant is selected from the group consisting of *Malus pumila*, *Malus domestica*, *Malus baccata*, *Malus halliana*, *Malus floribunda*, and *Malus prunifolia*.

* * * * *